United States Patent
Li et al.

(10) Patent No.: US 11,484,600 B2
(45) Date of Patent: Nov. 1, 2022

(54) INTERMEDIATE DRUG WITH SYNERGISTIC ANTICANCER ACTIVITY AND POLYETHYLENE GLYCOL-COUPLED SYNERGISTIC ANTICANCER DRUG, AND PREPARATION METHOD THEREFOR AND USE THEREOF

(71) Applicant: CHONGQING UPGRA BIOTECHNOLOGY CO., LTD., Chongqing (CN)

(72) Inventors: Gaoquan Li, Chongqing (CN); Bin Wang, Chongqing (CN); Dajun Li, Chongqing (CN); Qian Zhang, Chongqing (CN); Lei Huang, Chongqing (CN); Maofen Chen, Chongqing (CN); Xiaodan Wu, Chongqing (CN); Liangyan Peng, Chongqing (CN); Tingting He, Chongqing (CN); Yanyan Zhang, Chongqing (CN); Yun Tang, Chongqing (CN); Huan Liu, Chongqing (CN); Jvyuan Shui, Chongqing (CN); Cuifang Zhang, Chongqing (CN); Jianhuan Li, Chongqing (CN)

(73) Assignee: Chongqing Upgra Biotechnology Co., Ltd., Chongqing (CN)

( * ) Notice: Subject to any disclaimer, the term of this patent is extended or adjusted under 35 U.S.C. 154(b) by 0 days.

(21) Appl. No.: 16/643,245

(22) PCT Filed: Jan. 22, 2018

(86) PCT No.: PCT/CN2018/073662
§ 371 (c)(1),
(2) Date: Feb. 28, 2020

(87) PCT Pub. No.: WO2019/041733
PCT Pub. Date: Mar. 7, 2019

(65) Prior Publication Data
US 2020/0261588 A1 Aug. 20, 2020

(30) Foreign Application Priority Data
Aug. 30, 2017 (CN) .......................... 201710761572.5

(51) Int. Cl.
| | | |
|---|---|---|
| A61K 47/64 | (2017.01) | |
| A61K 47/54 | (2017.01) | |
| A61K 47/60 | (2017.01) | |
| A61P 35/00 | (2006.01) | |
| A61K 31/4184 | (2006.01) | |
| A61K 31/517 | (2006.01) | |
| A61K 31/519 | (2006.01) | |
| A61K 31/5377 | (2006.01) | |
| A61K 38/05 | (2006.01) | |
| A61K 38/06 | (2006.01) | |
| A61K 38/07 | (2006.01) | |
| A61K 45/06 | (2006.01) | |
| A61K 47/12 | (2006.01) | |

(52) U.S. Cl.
CPC .......... *A61K 47/64* (2017.08); *A61K 31/4184* (2013.01); *A61K 31/517* (2013.01); *A61K 31/519* (2013.01); *A61K 31/5377* (2013.01); *A61K 38/05* (2013.01); *A61K 38/06* (2013.01); *A61K 38/07* (2013.01); *A61K 45/06* (2013.01); *A61K 47/12* (2013.01); *A61K 47/542* (2017.08); *A61K 47/60* (2017.08); *A61P 35/00* (2018.01)

(58) Field of Classification Search
None
See application file for complete search history.

(56) References Cited

U.S. PATENT DOCUMENTS

| | | | | |
|---|---|---|---|---|
| 8,664,181 B2 * | 3/2014 | Kratz | ..................... | A61K 47/65 |
| | | | | 514/19.2 |
| 2015/0031644 A1 | 1/2015 | Yan et al. | | |

FOREIGN PATENT DOCUMENTS

| | | |
|---|---|---|
| CN | 1876187 A | 12/2006 |
| CN | 101461946 A | 6/2009 |
| CN | 104105508 A | 10/2014 |
| CN | 104987504 A * | 10/2015 |
| CN | 107670050 B | 2/2018 |

(Continued)

OTHER PUBLICATIONS

Kang et al. "Inference of synergy/antagonism between anticancer drugs from the pooled analysis of clinical trials" BMC Medical Research Methodology 2013, 13:77, p. 1-8 (Year: 2013).*

(Continued)

*Primary Examiner* — Christina Bradley
(74) *Attorney, Agent, or Firm* — Sterne, Kessler, Goldstein & Fox P.L.L.C.

(57) ABSTRACT

Disclosed are an intermediate drug having synergistic anticancer activity and a polyethylene glycol-coupled synergistic anticancer drug, and a method preparing therefor and use thereof. The intermediate drug has the general structural formula of (I), and the polyethylene glycol-coupled synergistic anticancer drug has the general structural formula of (II). The drugs achieve the combined medication of various anticancer drugs and avoid the toxic reaction caused by the interaction among the drugs or by the pharmacokinetics of the drugs when taking various anticancer drugs, facilitate overcoming the multidrug resistance of cancers, have a synergistic effect, and can be used for preparing anticancer medicaments and for treating cancers.

17 Claims, 4 Drawing Sheets
Specification includes a Sequence Listing.

(56) References Cited

FOREIGN PATENT DOCUMENTS

| WO | WO 2012/131399 A1 | 10/2012 |
|---|---|---|
| WO | WO 2013/079964 A1 | 6/2013 |
| WO | WO 2013/096388 A1 | 6/2013 |
| WO | WO 2015/057876 A1 | 4/2015 |
| WO | WO 2015/187540 A1 | 12/2015 |
| WO | WO 2016/193955 A1 | 12/2016 |
| WO | WO 2017/123603 A1 | 7/2017 |
| WO | WO 2017/132518 A1 | 8/2017 |

OTHER PUBLICATIONS

Narayan et al. "A cancer drug atlas enables synergistic targeting of independent drug vulnerabilities," Nat Commun 11, 2935 (2020), p. 1-14 (Year: 2020).*

Tenth et al. "Searching Synergistic Dose Combinations for Anticancer Drugs," Front. Pharmacol., May 22, 2018, p. 1-7 (Year: 2018).*

Office action for Japanese Patent Application No. 2020-533331, dated May 11, 2021, The Japan Patent Office, Tokyo, Japan.

Hou, J., et al., "RGD peptide conjugation results in enhanced antitumor activity of PD0325901 against glioblastoma by both tumor-targeting delivery and combination therapy." International Journal of Pharmaceutics, 505:329-340 (May 2016).

Gilad, Y., et al., "Dual-Drug RGD Conjugates Provide Enhanced Cytotoxicity to Melanoma and Non-Small Lung Cancer Cells." PeptideScience, 106(2):160-171 (Dec. 2015).

Zhao, H., et al., "Novel Prodrugs of SN38 Using Multiarm Poly-(ethylene glycol) Linkers." Bioconjugate Chem. 19:849-859 (2008).

Aina, O.H., et al., "From Combinatorial Chemistry to Cancer-Targeting Peptides." Molecular Pharmaceutics, 4(5):631-651 (2007).

Moral, E.G. and Siahaan, T.J., "Conjugates of Cell Adhesion Peptides for Therapeutics and Diagnostics Against Cancer and Autoimmune Diseases." Curr. Top. Med. Chem. 17(32):3425-3443 (Feb. 2018).

Extended European Search Report including supplementary European Search Report and European Search Opinion for counterpart EP Appl. No. 18851929.2; dated Apr. 15, 2021 from European Patent Office, Munich, Germany.

International Search Report (ISR) for PCT/CN2018/073662; I.A. fd dated Jan. 22, 2018, dated May 30, 2018 from the State Intellectual Property Office of the P.R. China, Beijing, China.

English Translation of International Search Report (ISR) for PCT/CN2018/073662; I.A. fd dated Jan. 22, 2018, dated May 30, 2018 from the State Intellectual Property Office of the P.R. China, Beijing, China.

International Preliminary Report on Patentability (IPRP), Chapter I of the Patent Cooperation Treaty, including the Written Opinion for PCT/CN2018/073662; I.A. fd dated Jan. 22, 2018, dated Mar. 3, 2020, by the International Bureau of WIPO, Geneva, Switzerland.

* cited by examiner

INTERMEDIATE DRUG WITH SYNERGISTIC ANTICANCER ACTIVITY AND POLYETHYLENE GLYCOL-COUPLED SYNERGISTIC ANTICANCER DRUG, AND PREPARATION METHOD THEREFOR AND USE THEREOF

The present application claims the priority of the Chinese Patent Application No. CN201710761572.5, filed on Aug. 30, 2017 to the Chinese Patent Office, with the title of "Intermediate drug with synergistic anticancer activity and polyethylene glycol-coupled synergistic anticancer drug, and preparation method and use thereof", the entire disclosure of which is incorporated herein by reference.

SEQUENCE LISTING

The instant application contains a Sequence Listing which has been submitted electronically in ASCII format and is hereby incorporated by referenced in its entirety. Said ASCII copy, created on Jan. 27, 2021, is named 4583-0010001_ST25.txt and is 518 bytes in size.

FIELD OF THE INVENTION

The present invention relates to the field of cancer treatment, and in particular, to an intermediate drug having synergistic anticancer activity and a polyethylene glycol-coupled synergistic anticancer drug, a method for preparing the same, use thereof and a method for treating cancer using the same.

BACKGROUND OF THE INVENTION

Cancer is a very complex and fatal disease and a huge health crisis that the developed and developing countries are currently experiencing. In 2012, there were more than 14 million new cancer cases worldwide. By 2020, there will be more than 15 million new cancer patients worldwide, which will bring serious influences to any country in the social, economic and medical aspect.

The clinical results of cancer treatment are generally disappointing, largely due to the heterogeneity and complexity of the devastating diseases. Traditional surgery and radiotherapy are only used for the treatment of localized diseases, while hormone therapy, chemotherapy, immunotherapy and targeted therapy are used alone or in combination with other treatments. Single and combination therapies, including chemotherapy, have evolved into effective treatments for many years. The clinical effects of combination therapy are not as good as expected, usually have higher toxicity, and are limited by the fact that the drug components cannot reach the desired spatial and temporal distribution in free molecular form, that is, the drug components cannot be delivered to the correct location at the appropriate time. Unless an effective drug carrier is used, inherent differences in the physicochemical and pharmacokinetic properties between the drug components will prevent the drug components from reaching the desired spatial and temporal distribution. At present, the emergence of tumor chemotherapy resistance or multidrug resistance has become a major challenge for cancer chemotherapy researchers.

SUMMARY OF THE INVENTION

The first aspect of the present invention provides an intermediate drug having synergistic anticancer activity or a derivative or a pharmaceutically acceptable salt thereof as shown by Formula I, a method for preparing the same, use thereof and a method for treating cancer using the same.

The second aspect of the present invention provides a polyethylene glycol-coupled synergistic anticancer drug or a derivative or pharmaceutically acceptable salt thereof as shown by Formula II, a method for preparing the same, use thereof and a method for treating cancer using the same.

In order to achieve the above objects of the present invention, the following technical solutions are adopted:

An intermediate drug having synergistic anticancer activity, or a derivative or pharmaceutical acceptable salt thereof as shown by formula I;

$$Z\text{-}[\text{-}N\text{-}AC]_i \quad (I)$$

wherein, i=2, 3, 4 or 5; Z is selected from dicarboxylic acid or polycarboxylic acid having amino group or corresponding acyl substituent thereof; N is selected from amino acid, dipeptide or polypeptide; AC is selected from anticancer drug having amino group, hydroxyl, carboxyl or acyl.

A polyethylene glycol-coupled synergistic anticancer drug, or a derivative or pharmaceutical acceptable salt thereof as shown by formula II;

$$PEG\text{-}[\text{-}X\text{-}(Y)_m\text{-}Z\text{-}[\text{-}N\text{-}AC]_i\}_j \quad (II)$$

wherein, PEG is selected from single-arm or multi-arm polyethylene glycol or polyethylene glycol derivative; X is selected from

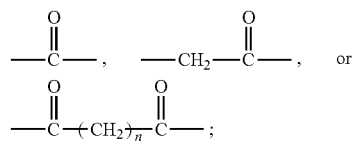

Y is selected from carboxylic acid having amino group or corresponding acyl substituent thereof; $Z\text{-}[\text{-}N\text{-}AC]_i$ is the intermediate drug having synergistic anticancer activity, or a derivative or pharmaceutical acceptable salt thereof as shown by formula I of any one of claims 1-3;

m=0, 1 or 2; n=1~5; j=arm number of PEG.

A method for preparing the intermediate drug having synergistic anticancer activity, or a derivative or pharmaceutical acceptable salt thereof as shown by formula I, wherein the method includes the following steps:

performing amidation reactions of at least two anticancer drugs having synergistic effect respectively with amino acid, peptide or a derivative thereof, resulting in first intermediates having a structure unit of N-AC in the formula I;

performing an amidation reaction of any one of the first intermediates with dicarboxylic acid, polycarboxylic acid having amino group or a corresponding acyl substituent thereof, resulting in a second intermediate having a structure unit of Z—N-AC in the formula I; and performing an amidation reaction of the second intermediate with the remaining first intermediate, resulting in the intermediate drug $Z\text{-}[\text{-}N\text{-}AC]_i$ as shown by formula I.

A method for preparing the polyethylene glycol-coupled synergistic anticancer drug, or a derivative or pharmaceutical acceptable salt thereof as shown by formula II, including the following steps:

performing amidation reaction of the intermediate drug as shown by formula I with carboxylic acid having amino group or a corresponding acyl substituent thereof, resulting in a fourth intermediate having structure unit $(Y)_m\text{-}Z\text{-}[\text{-}N\text{-}$ AC]$_i$ in formula II; and coupling the fourth intermediate with polyethylene glycol or a derivative thereof by amide bond, resulting in a product having a structure as shown by formula II.

Use of the intermediate drug having synergistic anticancer activity, or a derivative or pharmaceutical acceptable salt thereof as shown by formula I for preparing an anticancer medicament.

Use of the intermediate drug having synergistic anticancer activity, or a derivative or pharmaceutical acceptable salt thereof as shown by formula I for treating cancer.

An anticancer medicament, which includes the intermediate drug having synergistic anticancer activity, or a derivative or pharmaceutical acceptable salt thereof as shown by formula I.

Use of the polyethylene glycol-coupled synergistic anticancer drug, or a derivative or pharmaceutical acceptable salt thereof as shown by formula II for preparing an anticancer medicament.

Use of the polyethylene glycol-coupled synergistic anticancer drug, or a derivative or pharmaceutical acceptable salt thereof as shown by formula II for treating cancer.

An anticancer medicament, which includes the polyethylene glycol-coupled synergistic anticancer drug, or a derivative or pharmaceutical acceptable salt thereof as shown by formula II.

A cancer treatment method, which employs the anticancer drug provided by the invention.

Compared with the prior art, the present invention has the beneficial effects including, for example:

The invention uses a dicarboxylic acid or a polycarboxylic acid having an amino group and an amino acid or a polypeptide as a linker, and combines at least two anticancer drugs having synergistic effects to obtain an anticancer dual-drug or an anticancer multi-drug, thereby obtaining a combination administration among multiple anticancer drugs, avoiding toxic reactions due to drug interactions and pharmacokinetics when taking multiple anticancer drugs. Such intermediate drugs are useful in the preparation of anticancer medicaments, such as the achievement of multi-target payloads in a single nano-drug.

On the basis of the above, the present invention uses polyethylene glycol as carrier. Since the end of the polyethylene glycol polymer chain has only one grafting site, it is difficult to graft multiple anticancer drugs simultaneously. The combination of dual or multiple drugs is necessary to solve the multidrug resistance of tumors. After years of research, the inventors solved the problem of "how to graft multiple anticancer drugs at the end of the polyethylene glycol polymer chain" by multi-step organic synthesis means, which makes it easier to synthesize polyethylene glycol-coupled anticancer dual-drug or even polyethylene glycol-coupled anticancer multi-drug, thereby achieving multi-target and multi-therapy simultaneous administration, and significantly reducing toxicity, beneficial to overcome multi-drug resistance of cancer. The intermediate drugs and polyethylene glycol-coupled drugs have synergistic interaction, can be used to prepare anticancer medicaments, and have great clinical value and broad market prospects.

BRIEF DESCRIPTION OF THE DRAWINGS

In order to more clearly illustrate the examples of the present invention or the technical solutions in the prior art, the drawings used in the embodiments or the description of the prior art will be briefly described below.

DETAILED DESCRIPTION OF THE EMBODIMENTS

Figure 1:
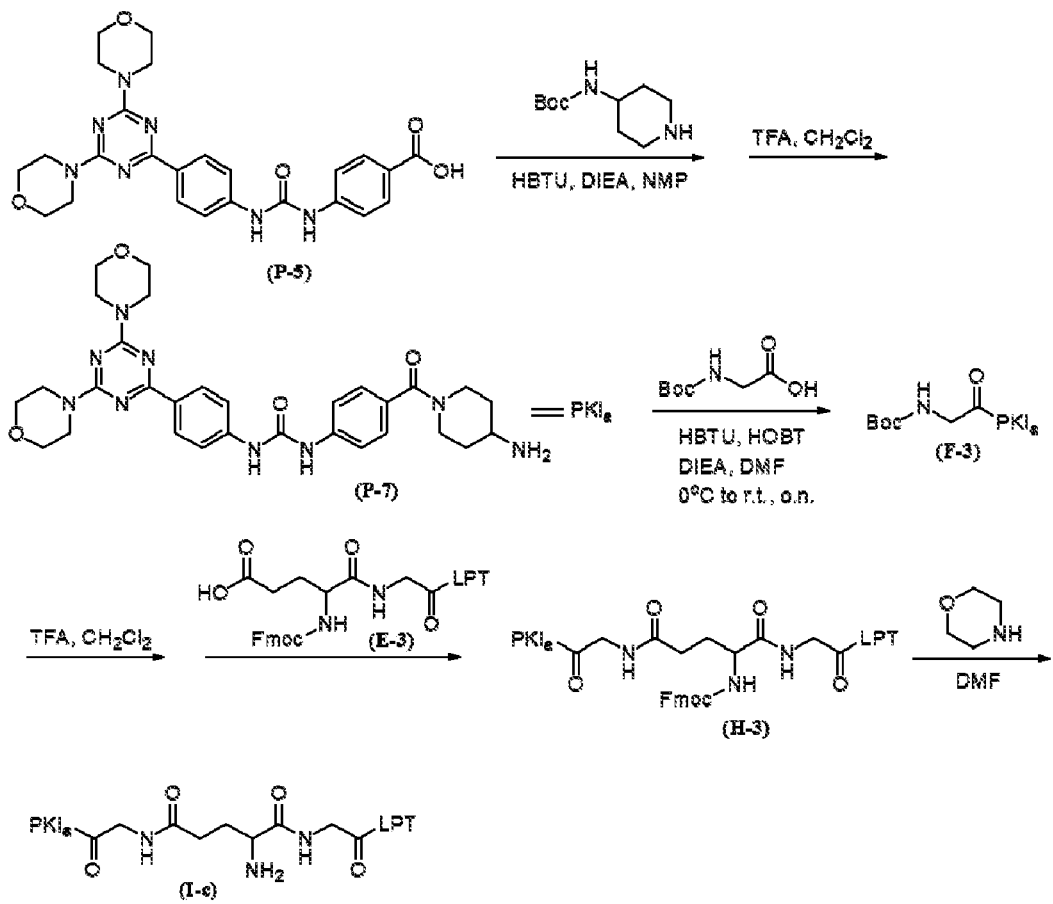
FIG. 1 is a scheme of synthesis route of the compound I-c provided in Example 5.

The embodiments of the present invention will be described in detail below with reference to the examples, but those skilled in the art will understand that the following embodiments are only used to illustrate the invention, and should not be construed as limiting the scope of the invention. If no specific conditions are specified in the embodiment, the general conditions or conditions recommended by the manufacturer are followed. The reagents or instruments of which the manufacturers are not indicated are commercially available conventional products.

The present embodiment provides an intermediate drug having synergistic anticancer activity, or a derivative or pharmaceutical acceptable salt thereof as shown by formula I;

$$Z \text{-}\!\!\left[\text{-N-AC}\right]_i \quad (1)$$

wherein, i=2, 3, 4 or 5; Z is selected from dicarboxylic acid, polycarboxylic acid having amino group or corresponding acyl substituent thereof, N is selected from amino acid, dipeptide or polypeptide; AC is selected from anticancer drug having amino group, hydroxyl, carboxyl or acyl. As shown in formula I, this intermediate drug has an amino acid or a polypeptide as a linker, and has a dicarboxylic acid or a polycarboxylic acid having an amino group as a linking bridge, thereby coupling at least two anticancer drugs having synergistic effects and forming anticancer dual-drug or anticancer multi-drug. Compared with the use of single anticancer drugs simultaneously, the toxicity is reduced, and the drug effect is enhanced.

N is selected from amino acid (for example glycine, serine, threonine, tyrosine, cysteine, aspartic acid and so on), dipeptide (for example GG, i.e. glycine-glycine; GS, i.e. glycine-serine; RE, i.e. arginine-glutamic acid), or polypeptide, such as tripeptide or tetrapeptide; wherein, tripeptide (for example GLG, i.e. glycine-leucine-glycine; GFA, i.e. glycine-phenylalanine-alanine; GLA, i.e. glycine-leucine-alanine), tetrapeptide (for example GFLG (SEQ ID NO: 1), i.e. glycine-phenylalanine-leucine-glycine). Amino acid or polypeptide is used as a linker, and the amino group and carboxyl therein play the role of connection groups. Amidation reactions of the amino group and carboxyl are performed respectively with anticancer drug and dicarboxylic acid or polycarboxylic acid having amino group, with strong reaction activity and good biocompatibility.

Z is selected from dicarboxylic acid, polycarboxylic acid having amino group or corresponding acyl substituent thereof. Z may be dicarboxylic acid having amino group, Z also may be polycarboxylic acid having amino group, Z also may be acyl substituent of dicarboxylic acid having amino group, and Z also may be acyl substituent of polycarboxylic acid having amino group. When Z is tricarboxylic acid having amino group, three synergistic anticancer drugs can be coupled on Z by acyls to form anticancer tri-drug. Similarly, when Z is tetracarboxylic acid having amino group, anticancer tetra-drug can be formed.

Further, the number of binding sites on Z is smaller than the amount of anticancer drug. Usually, at one binding site (for example a carboxyl) one anticancer drug can be bound. However, at one binding site two anticancer drugs can be bound by combining the two anticancer drugs together first to form an organics, and then binding the organics to the binding site. Similarly, at one binding site three or more than three anticancer drugs also can be bound.

Further, when Z is dicarboxylic acid having amino group, Z is any one selected from glutamic acid, glutamic acid derivative, aspartic acid, aspartic acid derivative, glutaric acid having amino group or derivative of glutaric acid having amino group. Glutamic acid and aspartic acid both are natural amino acid having two carboxyl, with strong reaction activity, and can be coupled with two amidated anticancer drug by acyl with high activity.

AC is selected from anticancer drug having amino group, hydroxyl, carboxyl or acyl, and anticancer drug can form amide bond with amino acid by amino group, hydroxyl, carboxyl or acyl, resulting in amino acid modified anticancer drug; anticancer drug also can form amide bond with amino acid or polypeptide by amino group, hydroxyl, carboxyl or acyl, resulting in polypeptide modified anticancer drug, which is easy to use Z for coupling.

Further, the anticancer drug includes immunotherapy cancer drug, chemotherapy drug or target drug, more preferably, at least one of AC is selected from immunotherapy cancer drug, at least one of AC is selected from chemotherapy drug or target drug, and the immunotherapy cancer drug has synergistic effect with the chemotherapy drug or the target drug. Optionally, at least one of AC is selected from chemotherapy drug, at least one of AC is selected from target drug, and the selected chemotherapy drug has synergistic effect with the target drug. Optionally, at least one of AC is selected from immunotherapy cancer drug, at least one of AC is selected from chemotherapy drug, at least one of AC is selected from target drug, and at least two of the immunotherapy cancer drug, chemotherapy drug and target drug have synergistic effect; further optionally, three of the immunotherapy cancer drug, chemotherapy drug and target drug have synergistic effect.

Thus, immunotherapy cancer drug-chemotherapy drug combined anticancer dual-drug, or immunotherapy cancer drug-target drug combined anticancer dual-drug, or chemotherapy drug-target drug combined anticancer dual-drug, or immunotherapy cancer drug-chemotherapy drug-target drug combined anticancer tri-drug can be obtained, thereby achieving multi-therapeutic combination of anticancer drugs;

wherein, the immunotherapy cancer drug may be selected from: lenalidomide, imiquimod, Resiquimod, NLG919, Epacadostat;

the chemotherapy drug may be selected from: paclitaxel, doxorubicin, 5-fluorouracil (5-FU), SB-743921, belotecan, etoposide; and the target drug may be selected from: dabrafenib, trametinib, palbociclib, ABT-888, Niraparib, de-terminal-dimethyl PKI-587, allosteric PKI-587, AZD-5363, MK-2206, lapatinib (Lapatinib ditosylate), dovitinib, Quisinostat, BIIB021.

The anticancer drug may also be selected from: Linifanib, MK-2206, TAK-580, SMK-17, JNJ-7706621, SNS-032, Ribociclib, Niraparib, HSP-990, XL-019, NVP-BSK805, Golotimod, Indoximod, PD-1/PD-L1 inhibitor 2, PD-1/PD-L1 inhibitor 1, Voreloxin, imatinib, Ponatinib, Dasatinib, Bosutinib, gefitinib, Vandetanib, Sunitinib, Nintedanib, Crizotinib, and Ceritinib.

SB-743921 has a structure formula of:

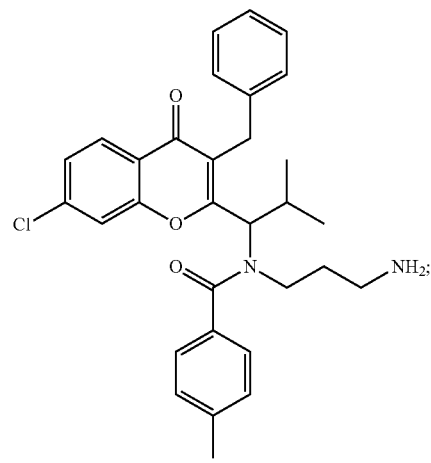 [SMILES: Cc1ccc(C(=O)N(CCCN)C(c2oc3cc(Cl)ccc3c(=O)c2Cc2ccccc2)C(C)C)cc1]

MK-2206 has a structure formula of:

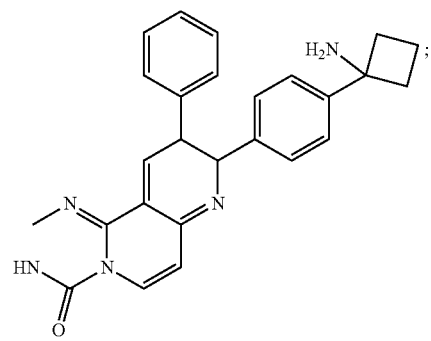 [SMILES: C/N=c1/c2c(ccn1C(N)=O)=NC(c1ccc(C3(N)CCC3)cc1)C(c1ccccc1)C=2]

BIIB021 has a structure formula of:

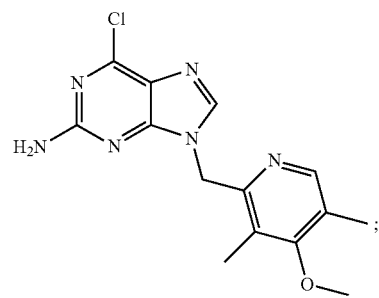 [SMILES: COc1c(C)cnc(Cn2cnc3c(Cl)nc(N)nc32)c1C]

ABT-888 has a structure formula of:

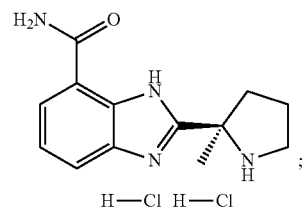

Linifanib (ABT-869) has a structure formula of:
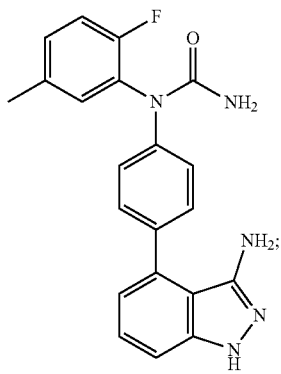 [SMILES: Cc1ccc(F)c(N(C(N)=O)c2ccc(-c3cccc4[nH]nc(N)c34)cc2)c1]
SMK-17 has a structure formula of:
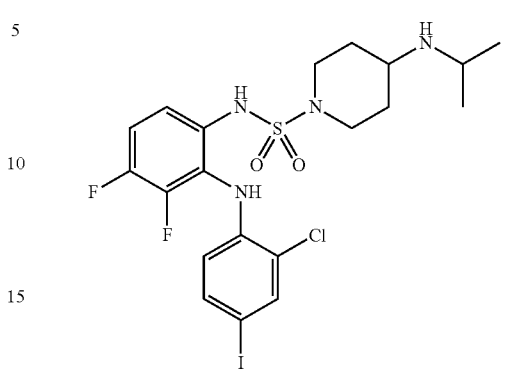
Lapatinib ditosylate has a structure formula of:
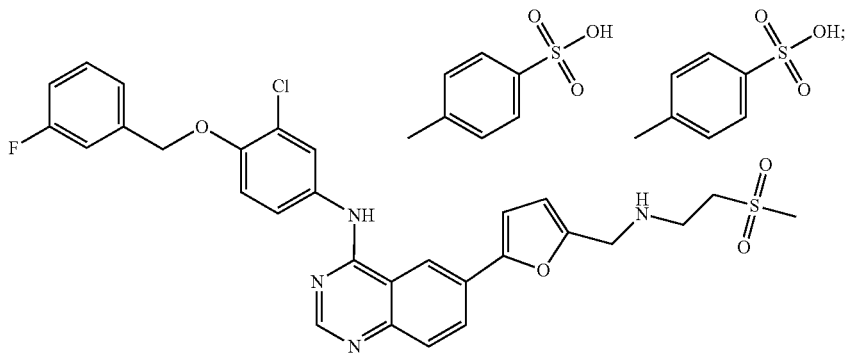
MK-2206 2HCl has a structure formula of:
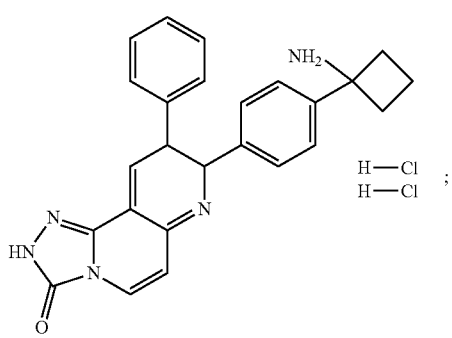
JNJ-7706621 has a structure formula of:
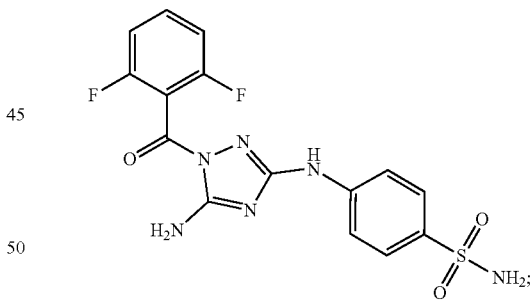
TAK-580 (MLN2480) has a structure formula of:
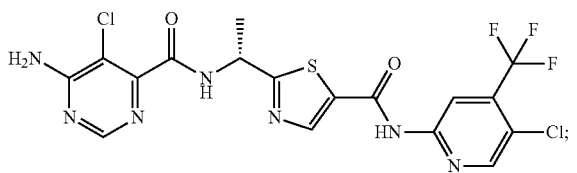 [SMILES: C[C@@H](NC(=O)c1ncnc(N)c1Cl)c1ncc(C(=O)Nc2cc(C(F)(F)F)c(Cl)cn2)s1]
SNS-032 (BMS-387032) has a structure formula of:
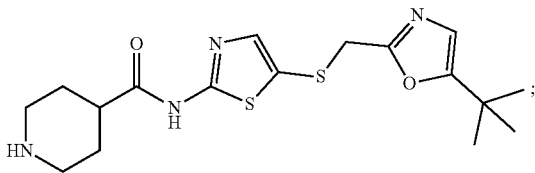 [SMILES: CC(C)(C)c1cnc(CSc2cnc(NC(=O)C3CCNCC3)s2)o1]

HSP-990 has a structure formula of:

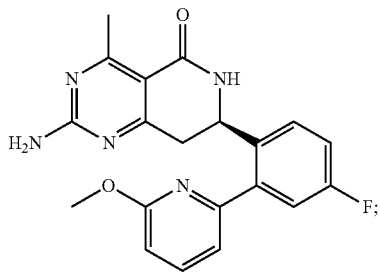 [SMILES: COc1cccc(-c2cc(F)ccc2[C@H]2Cc3nc(N)nc(C)c3C(=O)N2)n1]

XL-019 has a structure formula of:

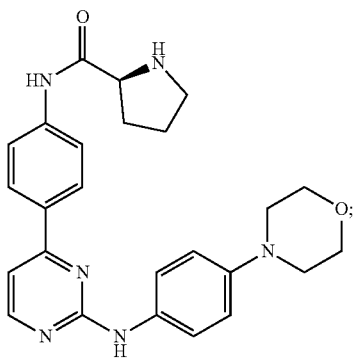 [SMILES: O=C(Nc1ccc(-c2ccnc(Nc3ccc(N4CCOCC4)cc3)n2)cc1)[C@@H]1CCCN1]

NVP-BSK805 has a structure formula of:

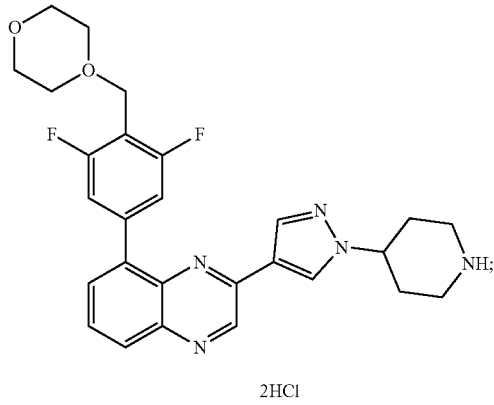

PD-1/PD-L1 inhibitor 2 has a structure formula of:

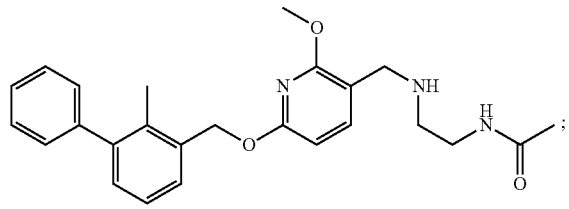 [SMILES: COc1nc(OCc2cccc(-c3ccccc3)c2C)ccc1CNCCNC(C)=O]

PD-1/PD-L1 inhibitor 1 has a structure formula of:

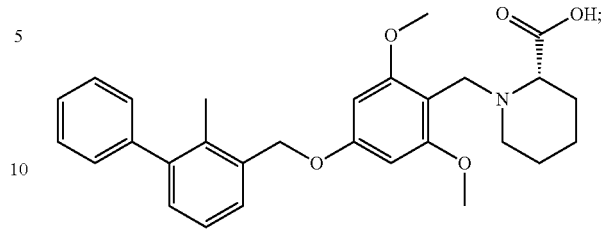

NLG919 has a structure formula of:

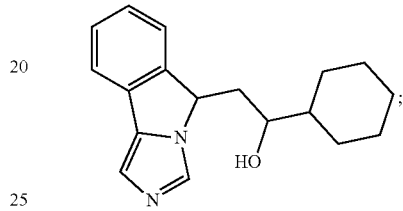

Imatinib or de-terminal-methyl imatinib has a structure formula of:

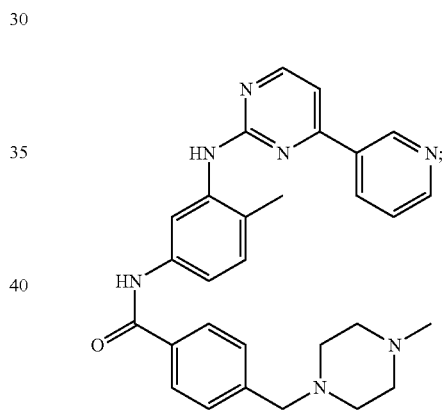

Ponatinib or de-terminal-methyl Ponatinib has a structure formula of:

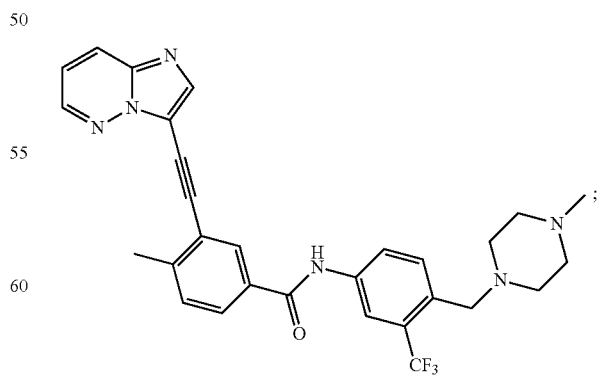

Bosutinib or Bosutinib which is demethylated at the terminal tertiary amine has a structure formula

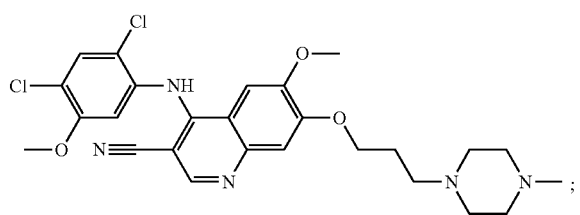 [SMILES: COc1cc(Nc2c(C#N)cnc3cc(OCCCN4CCN(C)CC4)c(OC)cc23)c(Cl)cc1Cl]

Gefitinib or gefitinib in which terminal morpholine ring is became primary amine has a structure formula of:

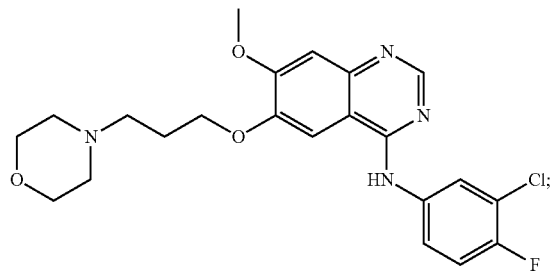 [SMILES: COc1cc2ncnc(Nc3ccc(F)c(Cl)c3)c2cc1OCCCN1CCOCC1]

Vandetanib or de-terminal-methyl Vandetanib has a structure formula of:

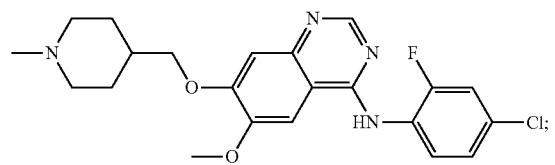 [SMILES: COc1cc2c(Nc3ccc(Cl)cc3F)ncnc2cc1OCC1CCN(C)CC1]

Sunitinib or Sunitinib in which terminal tertiary amine became primary amine has a structure formula of:

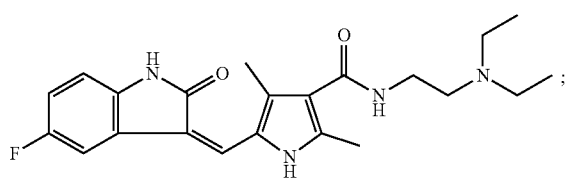 [SMILES: CCN(CC)CCNC(=O)c1c(C)[nH]c(/C=C2\C(=O)Nc3ccc(F)cc32)c1C]

Nintedanib or Nintedanib which is demethylated at the terminal tertiary amine has a structure formula of:

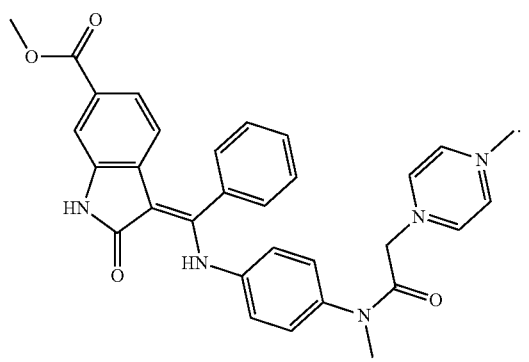

Further, the anticancer drug may also be a combination of at least two selected from Chlorambucil, melphalan, N-Formylmerphalan, lomustine, semustine, streptozocin, chlorozotocin, carboplatin, oxaliplatin, lobaplatin, tegafur, carmofur, Furtulon, cytarabine, enocitabine, palmitoyl cytarabine, ancitabine, azacytidine, mercaptopurine, thioguanine, Pentostatin, methotrexate, actinomycin D, bleomycin, daunorubicin, epirubicin, zorubicin, aclarubicin, mitoxantrone, Bisantrene, mitomycin C, hydroxycamptothecin, camptothecin, irinotecan, topotecan, Rubitecan, vinblastine, vincristine, vindesine, vinorelbine, docetaxel, nilotinib, erlotinib, Icotinib, afatinib, sorafenib, Pazopanib, vandetanib, vemurafenib, crizotinib, Ruxolitinib, axitinib, Regorafenib, Cabozantinib, trametinib, dabrafenib, Ibrutinib, Idelalisib, Lenvatinib, Bortezomib, Carfilzomib, Everolimus, Sirolimus, Tofacitinib, Olaparib, aflibercept, Romidepsin, Belinostat, Panobinostat, Palifermin, temsirolimus, Vorinostat, idelalisib, AZD9291, Cobimetinib, vismodegib, ixazomib, sonidegib, omacetaxine mepesuccinate, Venetoclax, Enzalutamide, Calicheamicins, Autistatins, Maytansinoids, Estradiol, tamoxifen, diethylstilbestrol, toremifene, idoxifene, miproxifene, droloxifene, raloxifene, arzoxifene, flutamide, nilutamide, Bicalutamide, testosterone, 5α-dihydrotestosterone, methyltestosterone, finasteride, dutasteride, dexamethasone, retinoic acid, niacin, nicotinamide, temozolomide, dacarbazine, etoposide, parthenolide, resveratrol, gemcitabine, metformin, trifluoperazine, thioridazine, salinomycin, curcumin, BKM120, BYL719, pictilisib, XL765, PF-05212384, PF-04691502, GS-9820, dactolisib, copanlisib, GDC-0941, GSK2141795, RG7422, BGT226, XL147, SAR260301, GSK2636771, GSK2269557, GSK2126458, GSK1059615, RG7604, RG7666, AMG 319, MLN1117, AZD5363, AZD8186, AZD6482, MK-8669, BGT226, GSK1059615, AZD8055, ipatasertib, GSK2110183, GSK690693, RG7440, Vemurafenib, LGX818, RG7304, MLN2480, Trametinib, MEK162, pimasertib, RG7167, TAK-733, Gefitinib, erlotinib, afatinib, dacomitinib, AZD8931, AEE788, BGJ398, LY2874455, AZD4547, TK1258, motesanib, Fostamatinib, GS-9973, TAK-659, MLN8237, AZD1152, tozasertib, AMG 900, MK-5108, TAK-901, GSK1070916, PF-03814735, LDK378, RG7853, RG7601, ABT-199, ABT-737, ABT-263, SAR405838, RG7388, JNJ-26854165, Tofacitinib, ruxolitinib, momelotinib, baricitinib, LY2784544, GSK2586184, GLPG0634, AZD1480, foretinib, LY2801653, SAR125844, AMG 208, AMG 337, Vorinostat, romidepsin, LBH589, JNJ-26481585, erismodegib, BMS-833923, LY2940680, PF-04449913, MK-8776, LY2603618, RG7741, AZD7762, olaparib, rucaparib, AZD2461, dinaciclib, LEE011, LY2835219, BAY 1000394, AZD5438, losmapimod, dilmapimod, LY2228820, MK-0752, PF-03084014, LY3039478,

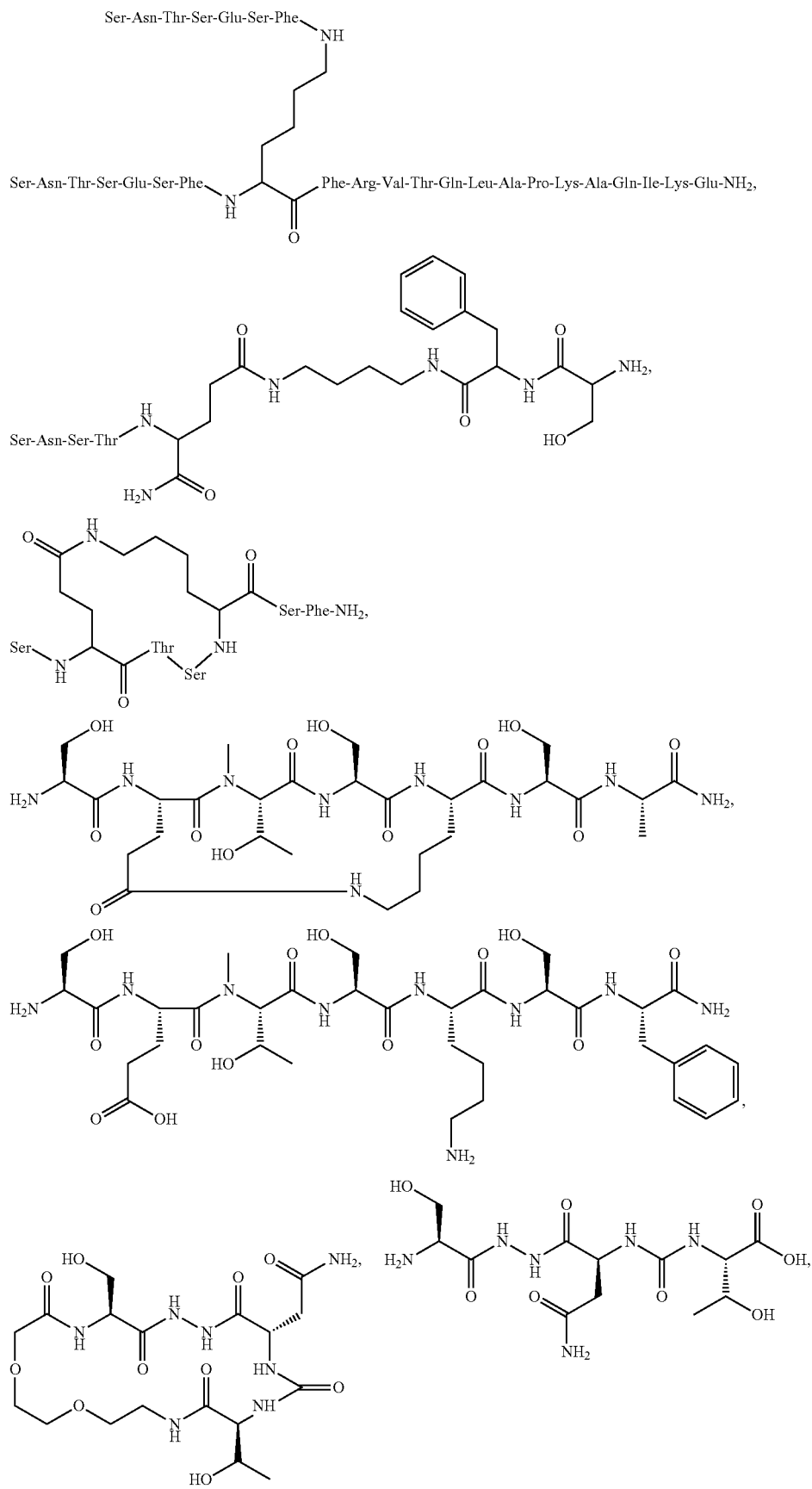

-continued
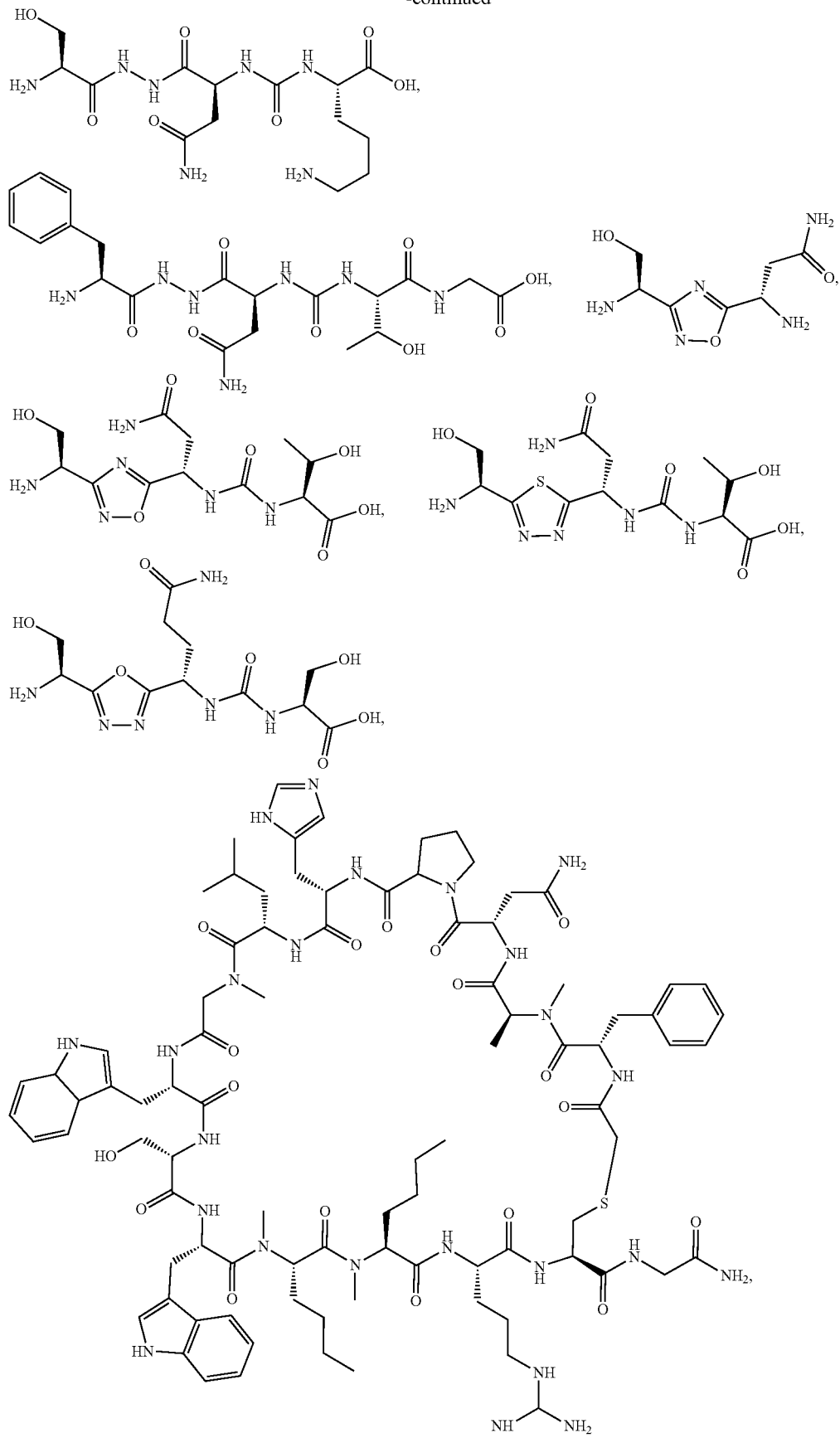

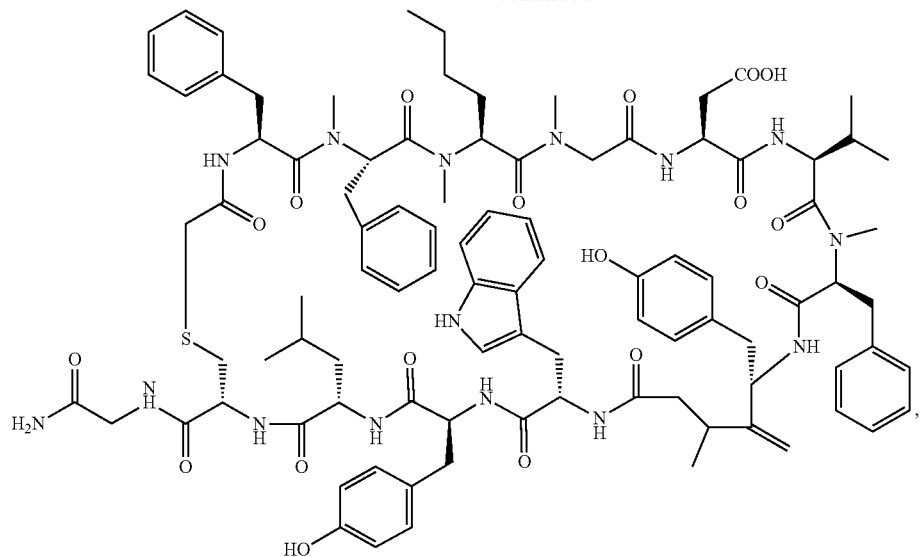
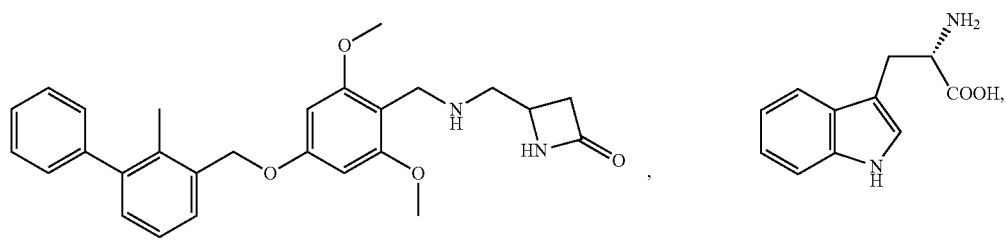
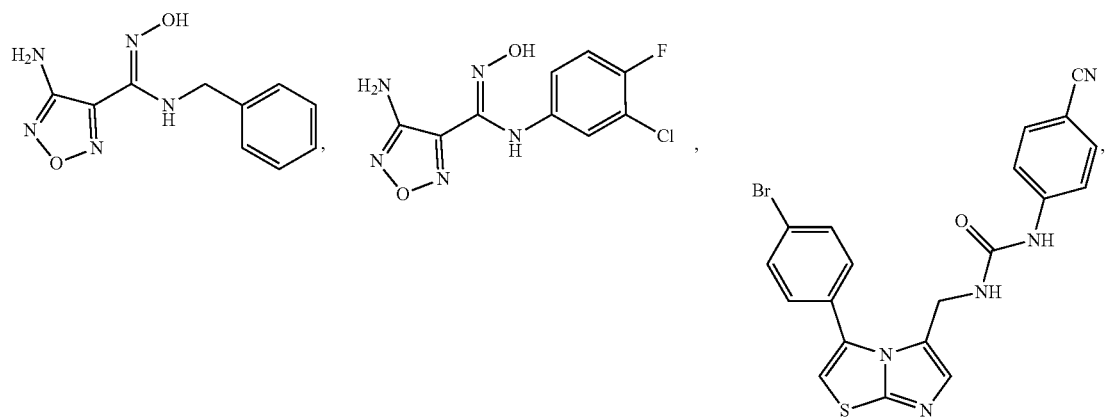

-continued
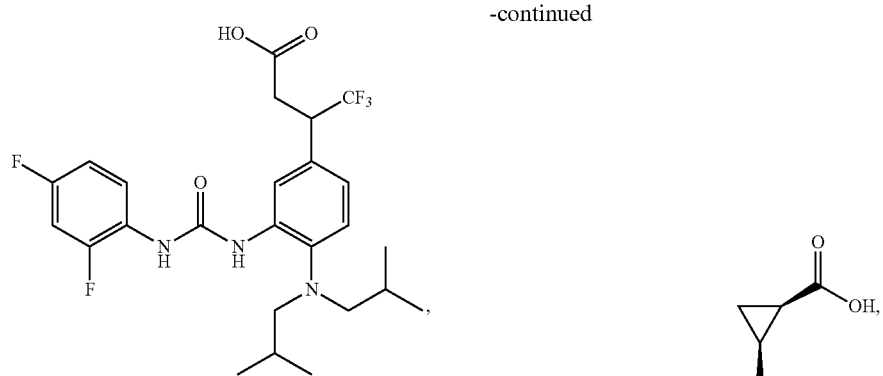
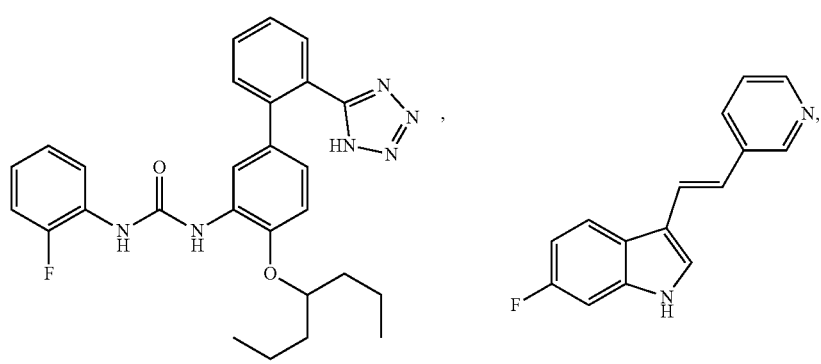
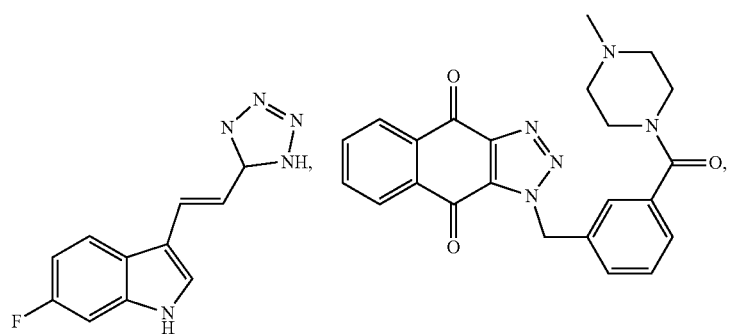
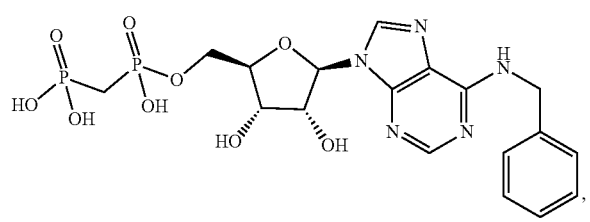

-continued
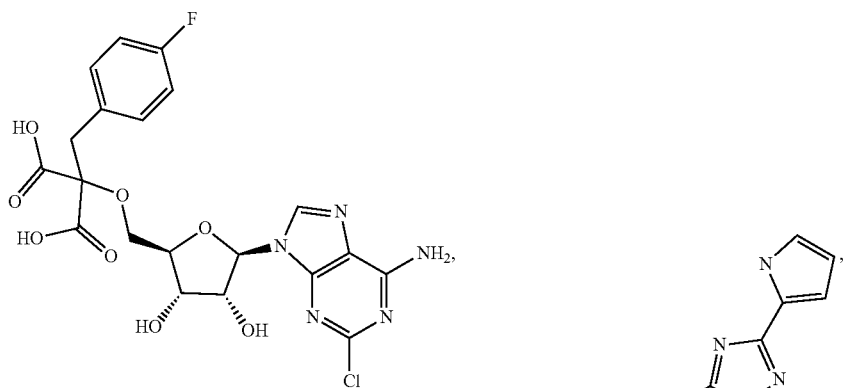
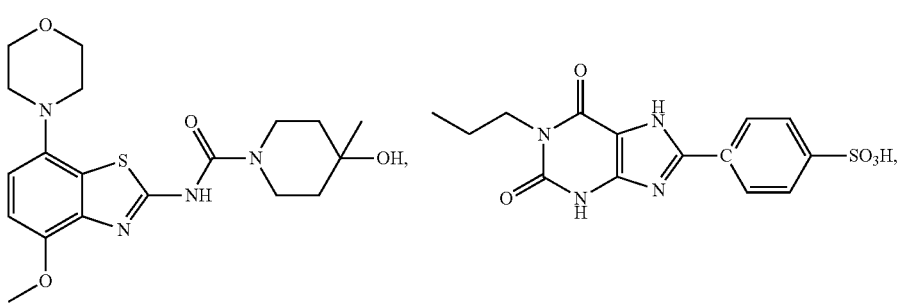
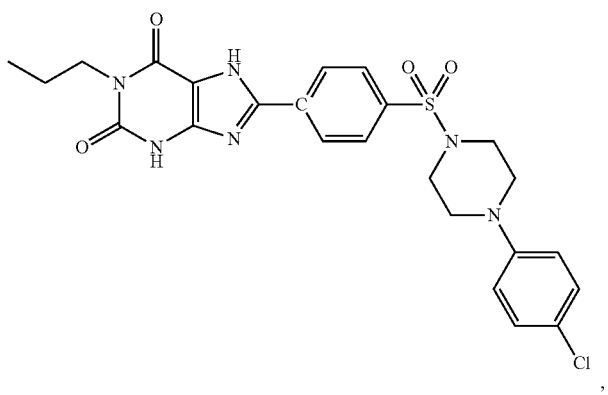
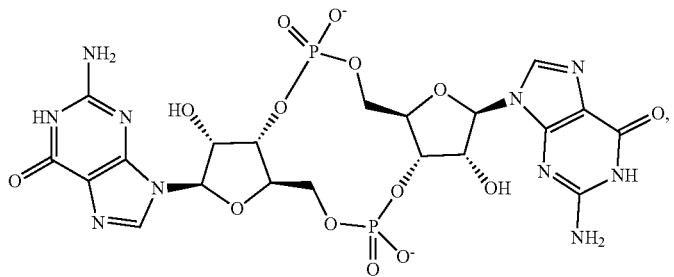

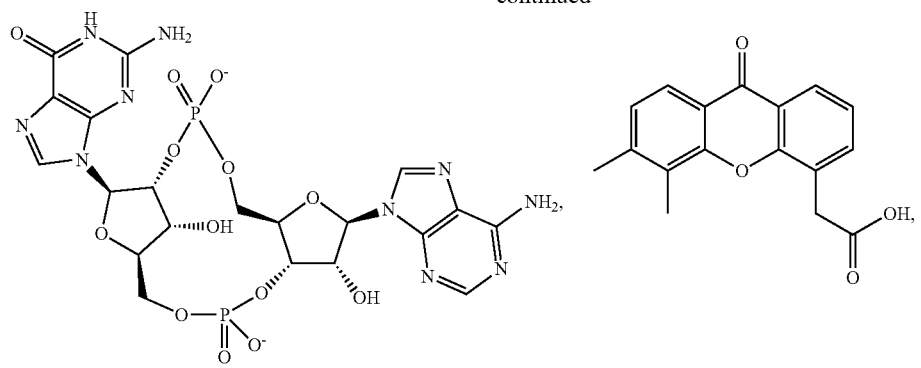
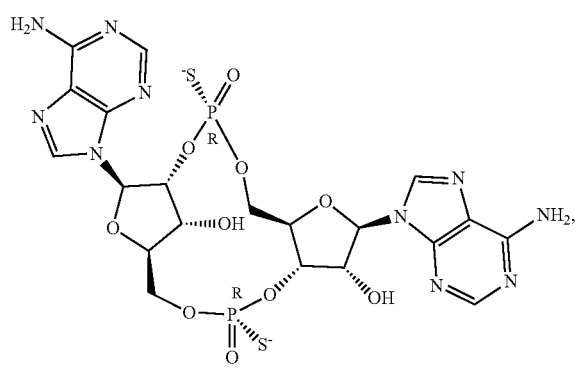
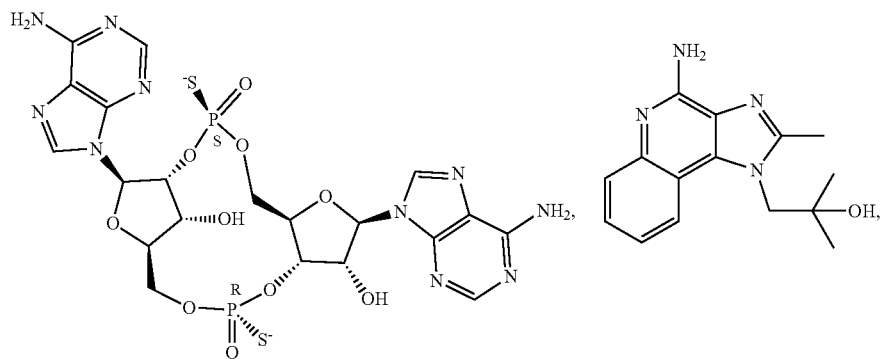
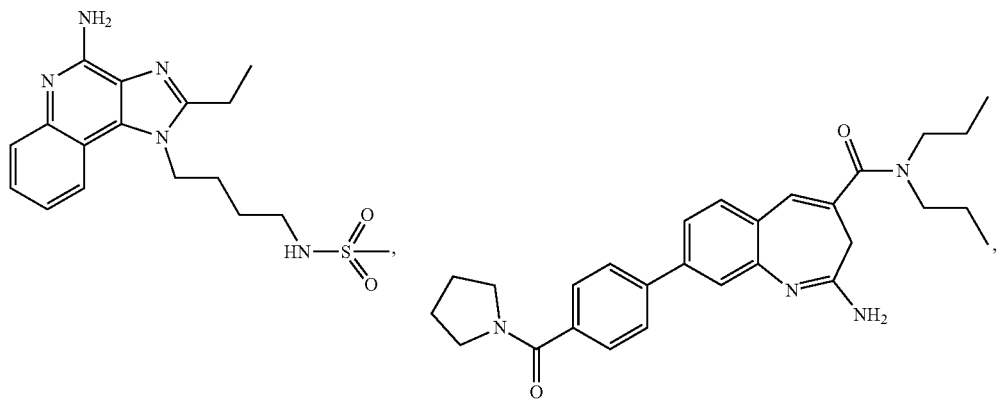

-continued
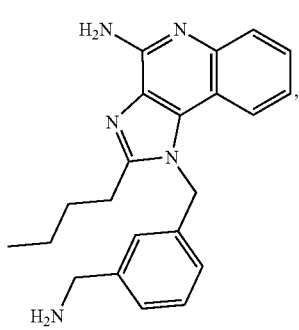
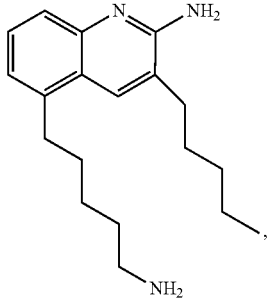
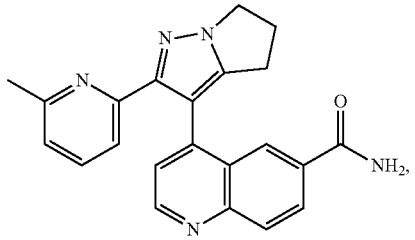
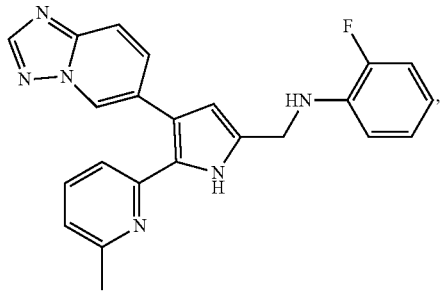
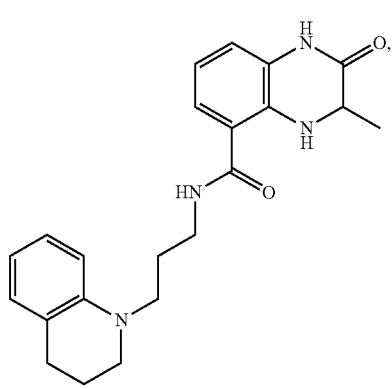
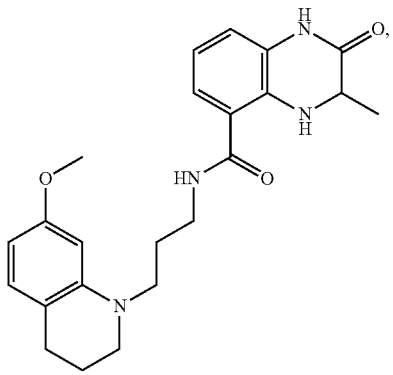
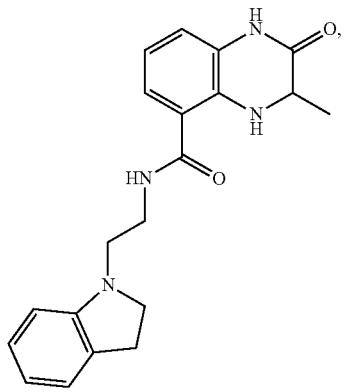
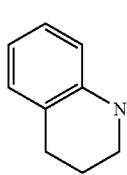
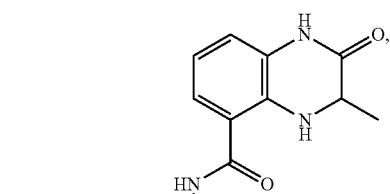
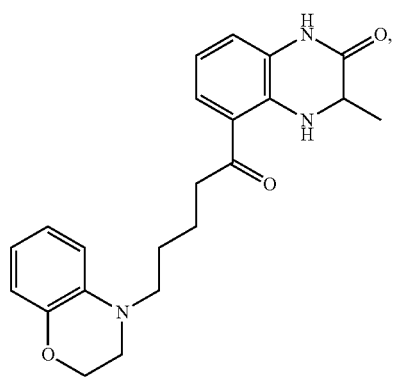

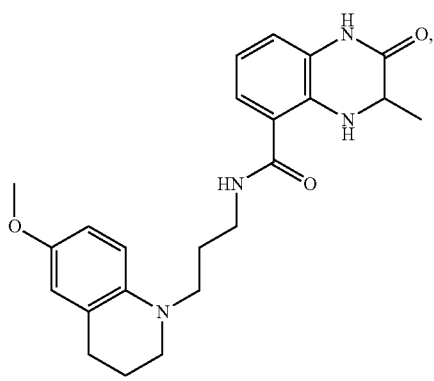

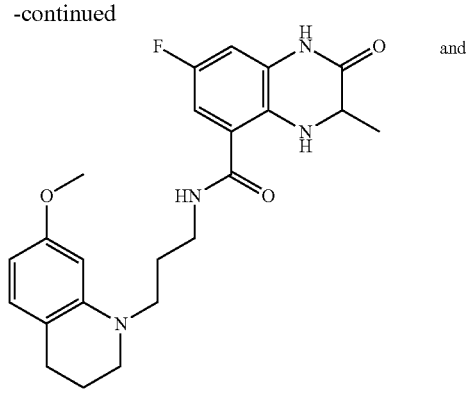 and

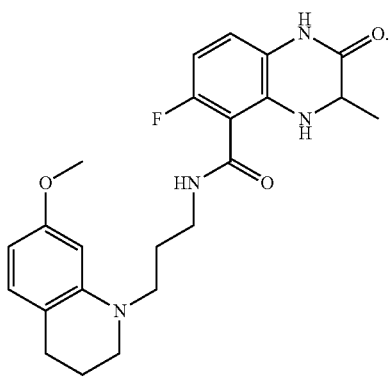

Further, in formula I, i=2, AC is a group selected from: a group consisting of Veliparib and allosteric PKI-587, a group consisting of palbociclib (briefly PCB) and allosteric PKI-587, a group consisting of lapatinib and de-terminal-dimethyl PKI-587, a group consisting of lapatinib and AZD5363, a group consisting of imiquimod and paclitaxel, or a group consisting of lenalidomide and de-terminal-dimethyl PKI-587. These groups of anticancer drugs all show a certain degree of synergistic effect, and can be used for preparing anticancer dual-drug;

wherein, the structure of allosteric PKI-587 is

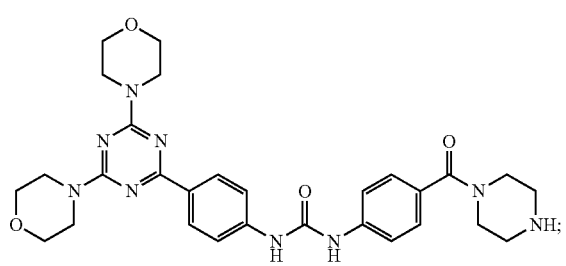 [SMILES: O=C(Nc1ccc(C(=O)N2CCNCC2)cc1)Nc1ccc(-c2nc(N3CCOCC3)nc(N3CCOCC3)n2)cc1]

the structure of de-terminal-dimethyl PKI-587 is

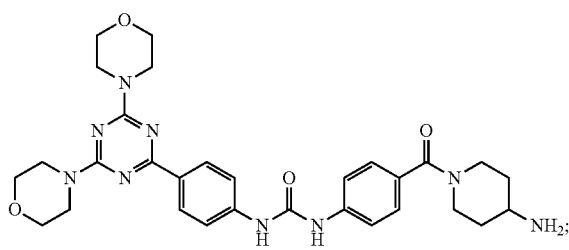 [SMILES: NC1CCN(C(=O)c2ccc(NC(=O)Nc3ccc(-c4nc(N5CCOCC5)nc(N5CCOCC5)n4)cc3)cc2)CC1]

the structure formula of AZD5363 is

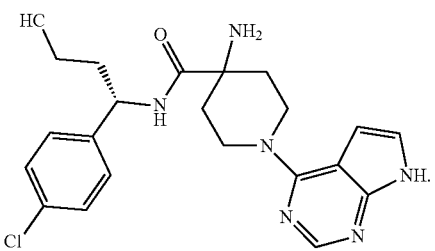 [SMILES: CCC[C@H](NC(=O)C1(N)CCN(c2ncnc3[nH]ccc23)CC1)c1ccc(Cl)cc1]

Preferably, the intermediate drug may be any one of the compounds as following:

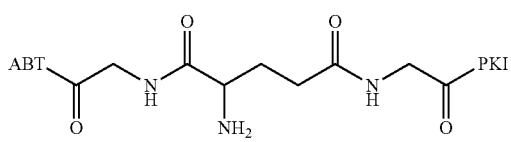

wherein, ABT is ABT-888, PKI is allosteric PKI-587;

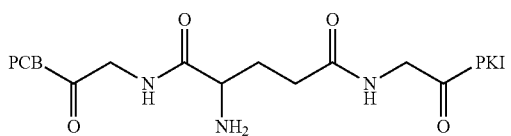

wherein, PCB is palbociclib, PKI is allosteric PKI-587;

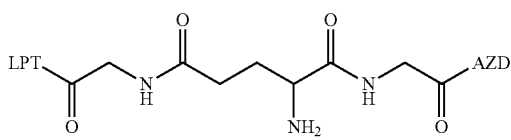

wherein, LPT is lapatinib, AZD is AZD5363;

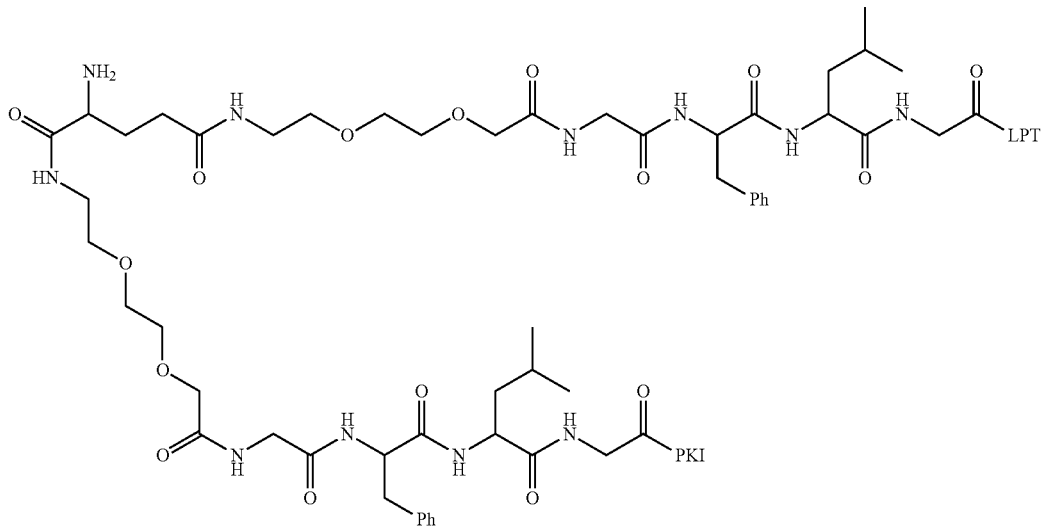

wherein, LPT is lapatinib, PKI is allosteric PKI-587;

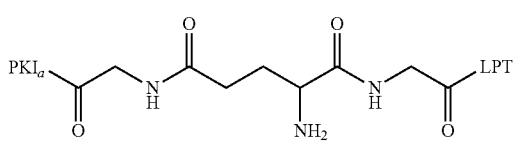

wherein, LPT is lapatinib, $PKI_a$ is de-terminal-dimethyl PKI-587.

A method for preparing the intermediate drug as shown by formula I above, wherein the method includes the following steps:

Step S1: performing amidation reactions of at least two anticancer drugs having synergistic effect respectively with an amino acid, derivative of amino acid, dipeptide, derivative of dipeptide, peptide or derivative of peptide, resulting in first intermediates having a structure unit of N-AC in the formula I;

preferably, the first intermediate is synthesized by a method including the following steps:

connecting the amino acid, derivative of amino acid, dipeptide, derivative of dipeptide, polypeptide or derivative of peptide having amino protecting group with anticancer drug by amidation in the presence of a polypeptide condensation agent, and then de-protecting the amino;

wherein, the polypeptide condensation agent includes HBTU, HOBT or HBTU. Alkaloid DIEA (N,N-diisopropylethylamine) may also be added to the reaction, and the reaction is performed under temperature of $-10 \sim 10°$ C., preferably $-4 \sim 4°$ C.

In order to enhance the specificity of the reaction, the amino group on the amino acid or polypeptide and or derivative thereof is protected with an amino protecting group before the reaction, and the amino protecting group is an alkoxycarbonyl amino protecting group, for example, a tert-butoxycarbonyl group (Boc), fluorenylmethoxycarbonyl (Fmoc), benzyloxycarbonyl (Cbz), trimethylsilylethoxycarbonyl (Teoc), and the like.

Step S2: performing an amidation reaction of any one of the first intermediates with dicarboxylic acid having amino group, polycarboxylic acid having amino group, a corresponding acyl substituent of dicarboxylic acid having amino group, or a corresponding acyl substituent of polycarboxylic acid having amino group, resulting in a second intermediate having a structure unit of Z—N-AC in the formula I;

preferably, the second intermediate is synthesized by a method including the following steps:

connecting the first intermediate with the dicarboxylic acid or polycarboxylic acid having amino group or the corresponding acyl substituent thereof, which simultaneously has amino protecting group and carboxyl protecting group, by amidation in the presence of PyAOP, and then de-protecting the carboxyl.

Further, amino-protected tert-butyl glutamate, tert-butyl aspartate are chosen, or Fmoc-protected tert-butyl glutamate, Fmoc-protected tert-butyl aspartate are used. It is beneficial to increase the reaction rate, reduce side product, and decrease coupling difficulty by simultaneously protecting amino group and carboxyl.

Step S3: performing an amidation reaction of the second intermediate with the remaining first intermediate, resulting in the intermediate drug $Z\text{-}[\text{N-AC}]_i$ as shown by formula I; preferably, the intermediate drug as shown by formula I is synthesized by a method further including the following steps: performing an amidation reaction of the second intermediate with at least one of the first intermediates in the presence of PyAOP and 2, 4, 6-trimethylpyridine at $-10°$ C.$\sim 10°$ C., and then de-protecting the amino group.

Further, at first at least two anticancer drugs are bound together to form an organics, and then amidation reaction is performed for the organics combined with at least two anticancer drugs and an amino acid or peptide or derivative thereof, thereby obtaining a drug intermediate as shown by formula I having at least one binding site linked with at least two anticancer drugs.

In the method, amino acid or polypeptide is used as a linker to prepare an amidated anticancer drug, i.e. the first intermediate, thereby reducing the steric hindrance of coupling at least two anticancer drugs simultaneously with the polycarboxylic acid having amino group, and reducing the reaction difficulty. Moreover, the types of reactions involved in the preparation of the intermediate drug are all amidation reactions, which have high selectivity, fast reaction rate, and less isomer side product, so the method has a high yield of product and fast reaction rate. The intermediate drug having synergistic anticancer activity or a derivative or pharmaceutical acceptable salt thereof prepared by the method may be used for preparing anticancer medicament, such as for achieving multi-target payload in a single nano-drug. When anticancer medicament is prepared, an excipient may be added, or a dosage form that is easy for administration may be prepared.

The above intermediate drug having synergistic anticancer activity or a derivative or pharmaceutical acceptable salt thereof, or a corresponding anticancer drug can be used for treating cancer.

The present embodiment also provides a polyethylene glycol-coupled synergistic anticancer drug, or a derivative or pharmaceutical acceptable salt thereof as shown by formula II;

PEG$\text{-}[\text{X}\text{-}(\text{Y})_m\text{-}\text{Z}\text{-}[\text{N-AC}]_i]_j$  (II)

wherein, PEG is selected from single-arm or multi-arm polyethylene glycol or polyethylene glycol derivative; X is selected from

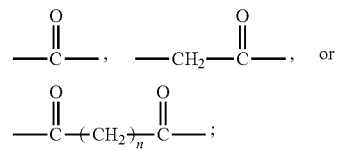

Y is selected from carboxylic acid having amino group or corresponding acyl substituent thereof, $Z\text{-}[\text{N-AC}]_i$ is the intermediate drug having synergistic anticancer activity, or a derivative or pharmaceutical acceptable salt thereof as shown by formula I;

m=0, 1 or 2; n=1~5; j=arm number of PEG.

In the compound of Formula II provided by the present embodiment, polyethylene glycol is used as carrier, and is coupled with the above intermediate drug $Z\text{-}[\text{N-AC}]_i$ by extension chain (Y), to obtain polyethylene glycol-coupled synergistic anticancer drug or derivative thereof, which not only retains properties of each of the anticancer drugs, but also has synergistic effect. By comparison with the single anticancer drug or $Z\text{-}[\text{N-AC}]_j$, the combined anticancer drugs coupled with polyethylene glycol has greatly decreasing toxicity and enhanced water solubility and bio-stability, and it has significant passive targeting and extreme low multi-drug resistance.

PEG is selected from single-arm or multi-arm polyethylene glycol or polyethylene glycol derivative, PEG may be single-arm polyethylene glycol or derivative of single-arm polyethylene glycol, also may be multi-arm polyethylene glycol or derivative of multi-arm polyethylene glycol. Preferably, PEG is single-arm, two-arm, four-arm or eight-arm polyethylene glycol, or PEG is derivative of single-arm, two-arm, four-arm or eight-arm polyethylene glycol; more preferably, the molecular weight of PEG is 12000, 20000, or 40000 Daltons.

Further, Y is selected from

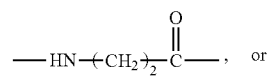

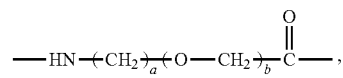

wherein, a=0~8; b=0~8; a and b are not 0 simultaneously. Optionally, a and b both are integers. Y is extension chain, which is beneficial to increase the number of branches, reduce the difficulty of coupling with polyethylene glycol, and improve the release efficiency of anticancer drug in the polyethylene glycol-coupled synergistic anticancer drug or derivative thereof.

More preferably, Y is selected from
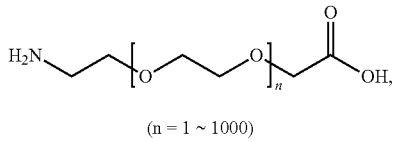
(n = 1 ~ 1000)
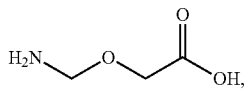
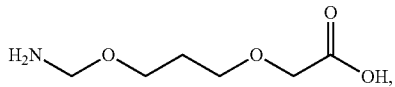
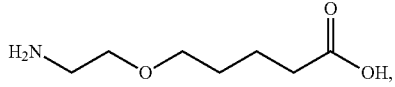
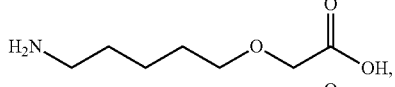
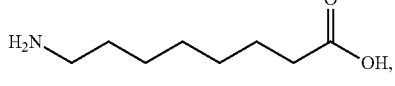
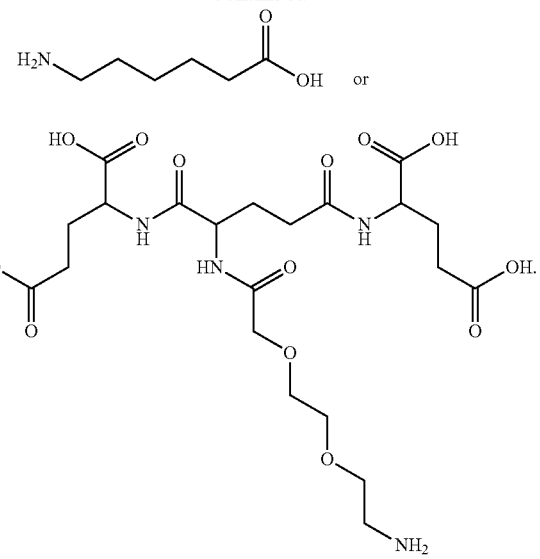
More particularly, the polyethylene glycol-coupled synergistic anticancer drug or a derivative or pharmaceutical acceptable salt thereof is any one of compounds as followed:
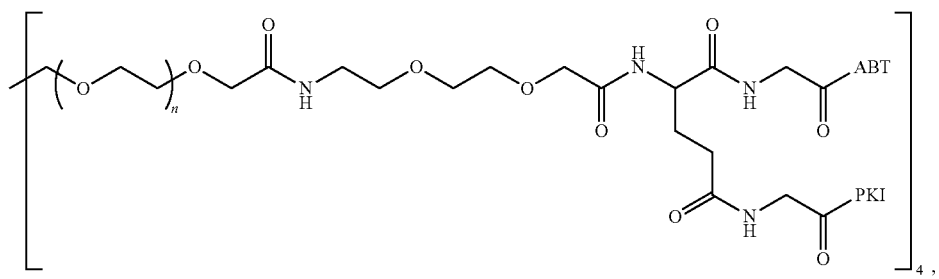
wherein, ABT is ABT-888, PKI is allosteric PKI-587;
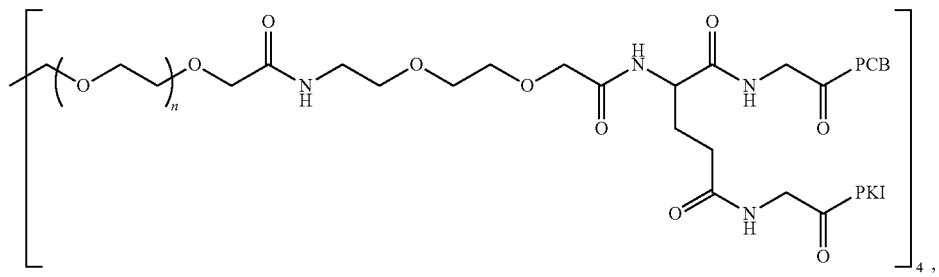
wherein, PCB is palbociclib, PKI is allosteric PKI-587;

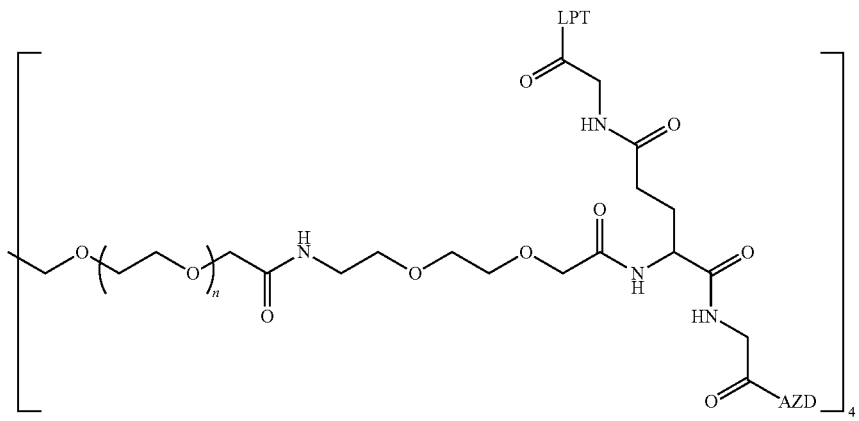
wherein, LPT is lapatinib, AZD is AZD5363;
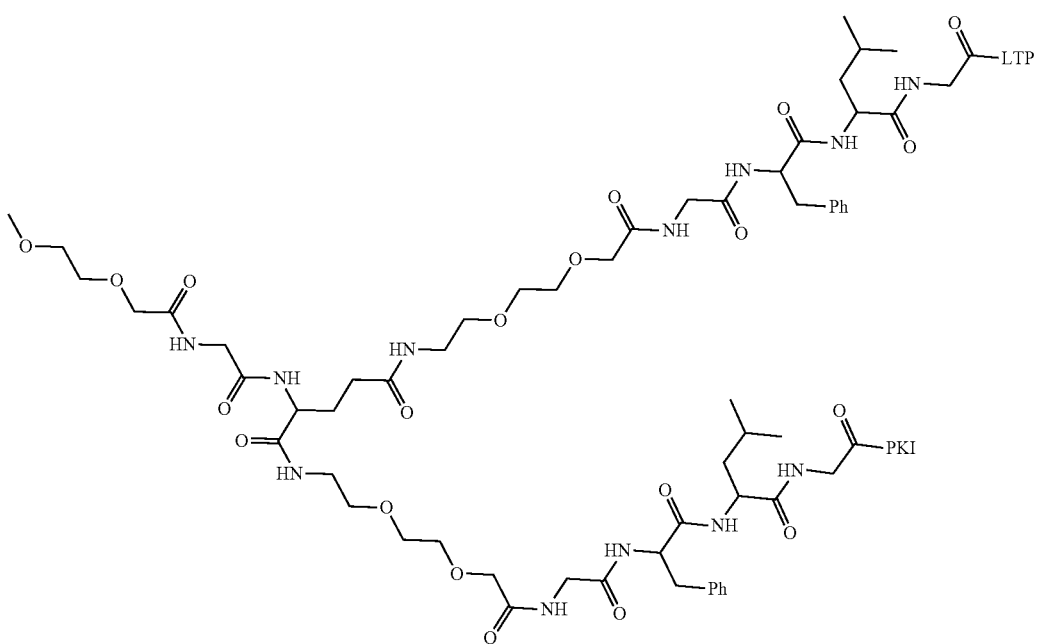
wherein, LPT is lapatinib, PKI is allosteric PKI-587;

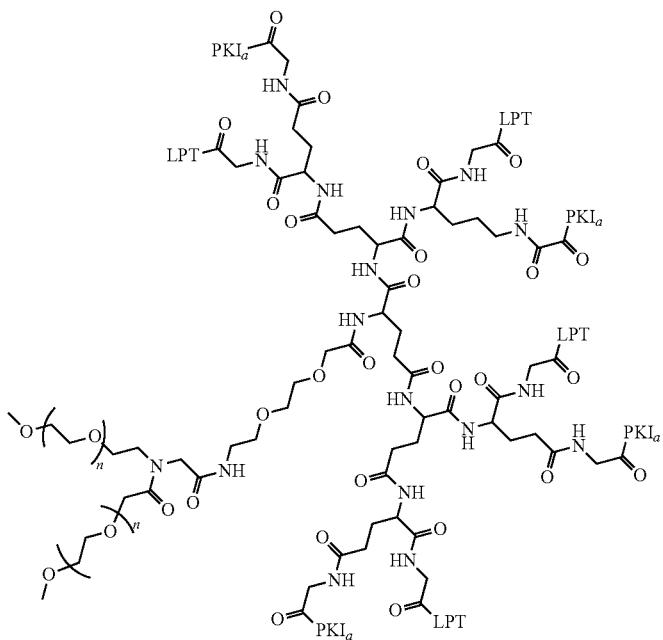

wherein, LPT is lapatinib, $PKI_a$ is de-terminal-dimethyl PKI-587.

A method for preparing a polyethylene glycol-coupled synergistic anticancer drug, or a derivative or pharmaceutical acceptable salt thereof as shown by formula II, wherein the method includes the following steps:

Step S1: performing amidation reaction of the intermediate drug as shown by formula I with carboxylic acid having amino group or a corresponding acyl substituent thereof, resulting in the fourth intermediate having structure unit $(Y)_m—Z—[-AC]_i$ in formula II;

preferably, the fourth intermediate is synthesized by a method including the following steps:

connecting the carboxylic acid, which has amino group and amino protecting group, or corresponding acyl substituent thereof with the third intermediate by amidation in the presence of a polypeptide condensation agent, and then de-protecting the amino group.

Step S2: coupling the fourth intermediate with polyethylene glycol or a derivative thereof by amide bond, resulting in a product having a structure as shown by formula II.

From the analysis of the reaction route, there is another way for the synthesis of the polyethylene glycol-coupled synergistic anticancer drug or derivative thereof, that is, coupling an anticancer drug to the polyethylene glycol and obtaining an anticancer drug-polyethylene glycol complex; and then coupling other anticancer drug(s) with the resulting anticancer drug-polyethylene glycol complex to form an anticancer dual-drug or anticancer multi-drug wherein polyethylene glycol is used as carrier. After years of research, the inventors have discovered that, it is difficult to introduce a second anticancer drug into the anticancer drug-polyethylene glycol complex due to the high steric hindrance and energy barrier of the reaction. The method has low yield and many side products, and is difficult to be enlarged in the industry. However, the method provided by this embodiment, including first synthesizing the anticancer dual-drug or anticancer multi-drug and then coupling the anticancer dual-drug or anticancer multi-drug with polyethylene glycol by extension chain, is simple, has mild reaction conditions, fast reaction rate and high yield, and is suitable for industrial production.

The polyethylene glycol-coupled anticancer dual-drug or the polyethylene glycol-coupled anticancer multi-drug can achieve multi-target and multi-therapy simultaneous administration, can greatly reduce toxicity, and is beneficial for overcoming multi-drug resistance of cancer, and has synergistic effect, can be used to prepare anticancer medicament, with significant clinical value and broad market prospects.

The polyethylene glycol-coupled anticancer dual-drug or the polyethylene glycol-coupled anticancer multi-drug or a derivative or pharmaceutical acceptable salt thereof can be further processed into other forms of anticancer drugs, which can be added with an excipient or prepared into various dosage forms that are easy to administer.

The above polyethylene glycol-coupled anticancer dual-drug or the polyethylene glycol-coupled anticancer multi-drug or a derivative or pharmaceutical acceptable salt thereof, or the corresponding anticancer medicament can be used to treat cancer.

The characteristics and performance of the present invention are described in detail below in conjunction with the examples:

Example 1

Synthesis of an Intermediate Drug Having Synergistic Anticancer Activity as Shown in Formula I-1

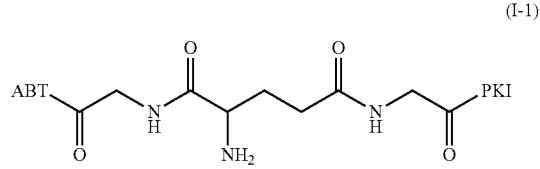

(I-1)

Example 1-1

Preparation of

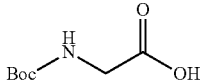
(A-1)

Glycine (11.1194 g, 148.12 mmol) was added to a 1 L round bottom flask, and dissolved in 1,4-dioxane (150 ml). Magnetic stick was added. 2N NaOH (88.88 ml, 177.78 mmol) was added, and Boc anhydride (48.5 g, 222.22 mmol) was added under stirring. After the reaction was complete, the reaction solution was transferred to a rotary evaporator to concentrate, and the concentrate was transferred to a 1 L separatory funnel, and washed with ethyl ether (100 ml) and repeated twice. The aqueous phase and the organic phase were separated, and the aqueous phase was adjusted to pH=4 by adding 1 mol/L hydrochloric acid. The aqueous phase was extracted with ethyl acetate (150 ml×5), and the organic phases were combined, dried over anhydrous sodium sulfate, and suction filtered. Water in the filtrate was removed with toluene, and solvent in the filtrate was removed by evaporation, resulting in Compound A-1, with a yield of 100%.

Example 1-2

Preparation of

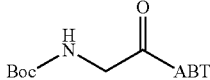
(B-1)

ABT-888 (4.8448 g, 19.8301 mmol, Shanghai LouLan), Compound A-1 (4.1691 g, 23.7962 mmol), HBTU (11.2806 g, 29.7452 mmol) and HOBT (4.0192 g, 29.7452 mmol) were added to a 500 ml round bottom flask, and dissolved in N,N-dimethylformamide (80 ml). The reaction solution was cooled in a low- and constant-temperature reaction bath at 0° C. for 20 min, then DIEA (15.53 ml, 89.2356 mmol) was slowly added. After 2 hours, the reaction solution was moved to room temperature and stirred overnight. The reaction solution was poured into saturated NaHCO₃ solution (200 mL), and extracted by ethyl acetate (200 mL×3), followed by washing with saturated sodium bicarbonate solution (200 mL×2), and the organic phase was dried over anhydrous MgSO₄ and suction filtered. Silica gel powder was added to the filtration product to make a solid solution, which was then loaded on a chromatographic column and eluted with gradient eluent of dichloromethane to 7% methanol/3% aqueous ammonia/dichloromethane. Eluate was collected and the solvent was removed by evaporation, to afford 9.7 g of Compound B-1, with a yield of 100%.

Example 1-3

Preparation of

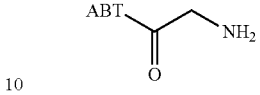
(C-1)

Compound B-1 (7.8 g, 19.4271 mmol) was added to a 500 ml round bottom flask, and dissolved in 80 ml of dichloromethane, and TFA (29.77 ml, 388.5430 mmol) was added under stirring. The reaction solution was stirred overnight at room temperature, and after the reaction was complete, the reaction solution was concentrated. Appropriate amount of methanol was added to dissolve the crude product, and appropriate amount of sodium bicarbonate powder was added to neutralize excess TFA. After the neutralization, suction filtration was performed, and appropriate amount of silica gel powder was added to the filtrate to make a solid solution, which was then loaded on a chromatographic column and eluted with gradient eluent of 1% methanol/dichloromethane to 5% methanol/dichloromethane, to 1% aqueous ammonia/5% methanol/dichloromethane to 4% aqueous ammonia/8% methanol/dichloromethane. Eluate was collected and the solvent was removed by evaporation, to afford 4.8740 g of Compound C-1, with a yield of 87%.

Example 1-4

Preparation of

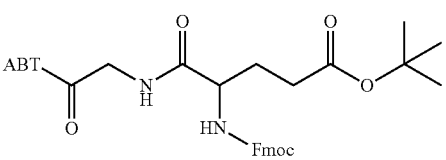
(D-1)

Compound C-1 (4.7 g, 15.5887 mmol), Fmoc-protected tert-butyl glutamate (9.2862 g, 21.8242 mmol) and PyAOP (11.3787 g, 21.8242 mmol) were placed into a 250 mL round bottom flask, and then 100 ml of DMF was added. The mixture was stirred for 30 min at −5° C. At the same condition, 2,4,6-trimethylpyridine (2.06 ml, 15.5887 mmol) was slowly added dropwise. After the addition of 2,4,6-trimethylpyridine was complete, the reaction continued for 2 h at low temperature, and then the reaction solution was moved to a freezer of 0° C. and stirred for 1 day. After the reaction was complete, the reaction solution was moved to a 2 L round bottom flask, and then about 800 ml of ethyl ether was added to precipitate. After precipitation, silica gel powder was added to make a solid solution, which was then loaded on a chromatographic column and eluted with gradient eluent of 1% methanol/dichloromethane to 7% methanol/dichloromethane. Eluate was collected and concentrated by evaporation to remove the solvent to afford 9.6957 g of Compound D-1, with a yield of 85.6%.

Example 1-5

Preparation of

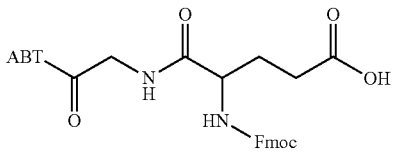
(E-1)

Compound D-1 (9.6957 g, 13.3366 mmol) was added to a 300 ml round bottom flask, and dissolved in 50 ml of dichloromethane. TFA (20.5 ml, 266.7318 mmol) was added under stirring. The reaction solution was stirred overnight at room temperature, and after the reaction was complete, the reaction solution was concentrated. Appropriate amount of methanol was added to dissolve crude product, and appropriate amount of sodium bicarbonate powder was added to neutralize excess TFA. After the neutralization, suction filtration was performed, and appropriate amount of silica gel powder was added to the filtrate to make a solid solution, which was then loaded on a chromatographic column and eluted with gradient eluent of 3% methanol/dichloromethane to 8% methanol/dichloromethane. Eluate was concentrated by evaporation to remove the solvent to afford 8.4 g of Compound E-1, with a yield of 93.9%.

ITMS +c ESI Full ms [120.00-1000.00] [M+H$^+$]: 653.40, [M+Na$^+$]: 675.40, [M+K$^+$]: 691.32.

$^1$H-NMR (400 Hz, DMSO-d$_6$) δ 12.70-12.00 (m, 1H), 9.52-8.25 (m, 1H), 8.25-7.75 (m, 4H), 7.80-7.52 (m, 4H), 7.49-7.10 (m, 4H), 4.35-4.15 (m, 3H), 4.15-3.90 (m, 3H), 3.90-3.70 (m, 4H), 2.75-2.60 (m, 1H), 2.20-2.15 (m, 1H), 2.15-1.95 (m, 2H), 1.95-1.88 (m, 3H), 1.86-1.81 (m, 1H), 1.76-1.65 (m, 1H).

Example 1-6

Preparation of

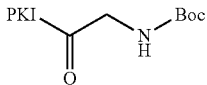
(F-1)

Allosteric PKI-587 (10 g, 17.43071 mmol, Changsha Kangpeng), Compound A-1 (3.665 g, 20.9169 mmol), HBTU (9.9156 g, 26.1461 mmol) and HOBT (3.533 g, 26.1461 mmol) were added to a 500 ml round bottom flask, and dissolved in N,N-dimethylformamide (80 ml). The solution was cooled in a low- and constant-temperature reaction bath of 0° C. for 20 min, and then DIEA (13.65 ml, 78.4382 mmol) was slowly added dropwise. After 2 hours, the reaction solution was moved to room temperature, and stirred overnight. The reaction solution was poured into saturated NaHCO$_3$ solution (200 mL), extracted by ethyl acetate (200 mL×3). The organic phases were combined, and added with silica gel powder to make a solid solution, which was then loaded on a chromatographic column and eluted with gradient eluent of 1% methanol/dichloromethane to 5% methanol/dichloromethane, to 3% aqueous ammonia/6% methanol/dichloromethane. Eluate was concentrated by evaporation to remove the solvent, to afford Compound F-1, with a yield of 100%.

Example 1-7

Preparation of

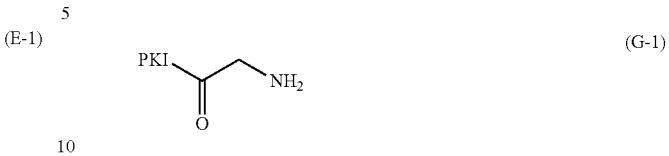
(G-1)

Compound F-1 (12.7314 g, 17.4307 mmol) was added to a 500 ml round bottom flask and dissolved in 100 ml of dichloromethane, and TFA (26.7 ml, 348.614 mmol) was added under stirring. The reaction solution was stirred overnight at room temperature, and after the reaction was complete, the reaction solution was concentrated. Appropriate amount of methanol was added to dissolve crude product, and appropriate amount of sodium bicarbonate powder was added to neutralize excess TFA. After the neutralization, suction filtration was performed, and appropriate amount of silica gel powder was added to the filtrate to make a solid solution, which was then loaded on a chromatographic column and eluted with gradient eluent of dichloromethane to 3% methanol/dichloromethane, to 2% aqueous ammonia/5% methanol/dichloromethane to 6% aqueous ammonia/7% methanol/dichloromethane. Eluate was collected and the solvent was removed by evaporation to afford 6.6 g of Compound G-1, with a yield of 60.1%.

Example 1-8

Preparation of

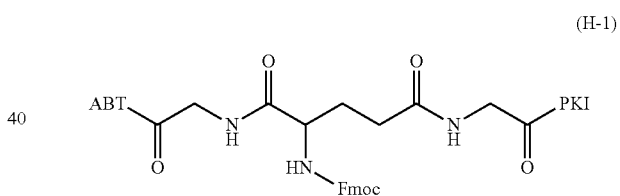
(H-1)

Compound E-1 (3.8784 g, 5.9458 mmol), Compound G-1 (2.5 g, 3.9638 mmol) and PyAOP (3.10 g, 5.9458 mmol) were placed in a 200 ml round bottom flask, and then 20 ml of DMF was added. The solution was stirred for 30 min at −5° C. At the same condition, 2,4,6-trimethylpyridine (0.52 ml, 3.9638 mmol) was slowly added dropwise. After the addition of 2,4,6-trimethylpyridine was complete, the reaction continued for 2 h at low temperature, and then the reaction solution was moved to a freezer of 0° C. and stirred for 1 day. The next day, Compound 11-58 (1.0 g, 1.5855 mmol) and 2,4,6-trimethylpyridine (0.208 ml, 1.5855 mmol) were added. The reaction solution was moved a freezer of 0° C. After the reaction was complete, the reaction solution was moved to a 2 L round bottom flask, and then anhydrous ethyl ether was added to precipitate. Silica gel powder was added to make a solid solution, which was then loaded on a chromatographic column and eluted with gradient eluent of 1% methanol/dichloromethane to 6% methanol/dichloromethane, to 2% aqueous ammonia/6% methanol/dichloromethane to 4% aqueous ammonia/7% methanol/dichloromethane. Eluate was collected and concentrated to afford 3.3 g of Compound H-1, with a yield of 78%.

Example 1-9

Preparation of

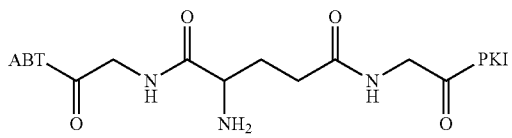
(I-1)

Compound H-1 (3.25 g, 2.5700 mmol) was added to a 500 ml round bottom flask, and dissolved in DMF (15 ml), and morpholine (3.7 ml, 77.0995 mmol) was added under stirring, followed with stirring at room temperature for 3 hours. After the reaction was complete, the reaction solution was moved to a 2 L round bottom flask. Anhydrous ethyl ether was added to precipitate. Ethyl ether phase was removed. The precipitate was dissolved in appropriate amount of methanol/dichloromethane, dried in vacuo, dissolved in a solvent, loaded on a chromatographic column, and eluted with gradient eluent of 5% methanol/dichloromethane to 4% aqueous ammonia/9% methanol/dichloromethane. Eluate was concentrated by evaporation to remove the solvent to afford 2.7 g of Compound I-1, with a yield of 100%.

ITMS +c ESI Full ms [300.00-1600.00] [M+H$^+$]: 1043.61, [M+Na$^+$]: 1065.64

$^1$H-NMR (400 Hz, DMSO-d$_6$) δ 12.70-12.30 (m, 1H), 9.35-9.20 (m, 1H), 9.10-8.95 (m, 2H), 8.35-8.25 (m, 2H), 8.15-8.05 (m, 1H), 7.85-7.75 (m, 1H), 7.70-7.65 (m, 1H), 7.60-7.50 (m, 4H), 7.40-7.35 (m, 2H), 7.30-7.20 (m, 1H), 4.15-4.05 (m, 6H), 4.03-3.95 (m, 2H), 3.96-3.90 (m, 2H), 3.90-3.70 (m, 11H), 3.54-3.43 (m, 7H), 3.42-3.40 (m, 1H), 3.15-3.10 (m, 1H), 2.25-2.14 (m, 3H), 2.14-2.06 (m, 2H), 2.06-1.97 (m, 3H), 1.96-1.92 (m, 1H), 1.90-1.86 (m, 3H), 1.85-1.80 (m, 1H), 1.62-1.50 (m, 1H).

Example 2

Synthesis of Polyethylene Glycol-Coupled Synergistic Anticancer Drug or Derivative Thereof as

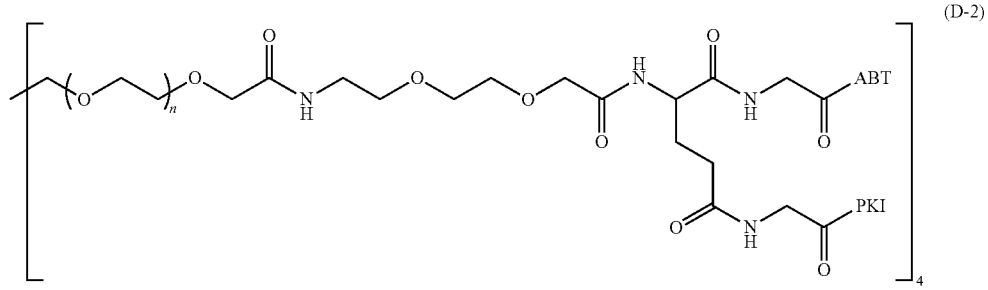
(D-2)

Example 2-1

Preparation of

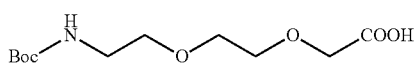
(A-2)

To a 1 L round bottom flask magnetic stick was added, H$_2$NCH$_2$CH$_2$OCH$_2$CH$_2$OH (9.542 ml, 95.1113 mmol) was added and dissolved in 150 ml of dichloromethane, and triethylamine (26.5133 ml, 190.2226 mmol) was added, and Boc anhydride (24.9096 g, 114.1335 mmol) was added under stirring. After the reaction was complete, the reaction solution was moved to a rotary evaporator to concentrate, dissolved in methanol, and added with sodium bicarbonate powder (13 g) under stirring to neutralize triethylamine. Suction filtration was performed, and silica gel powder was added to make a solid solution, which was then loaded on a chromatographic column and eluted with gradient eluent of 10% ethyl acetate/petroleum ether to 50% ethyl acetate/petroleum ether, followed by elution with gradient eluent of 3% methanol/ethyl acetate to 6% methanol/ethyl acetate. Eluate was collected and the solvent was removed by evaporation, resulting in 16.3341 g of compound

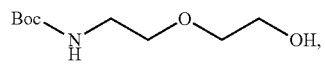 [SMILES: CC(C)(C)OC(=O)NCCOCCO]

with a yield of 83.77%.

Compound

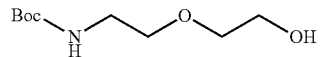

(16.334 g, 75.581 mmol) was placed in a 1 L round bottom flask, and 200 ml of tetrahydrofuran was added. The reaction solution was stirred at −5° C., and potassium tert-butoxide (75.58 ml, 75.581 mmol) was added dropwise by a liquid separator under protection of nitrogen gas. After 40 min, ethyl bromoacetate (10.56 ml, 95.4972 mmol) was added, and the temperature was adjusted to 0° C. After stirring for 3 hours, the reaction solution was moved to room temperature and stirred overnight. After the reaction was complete, the reaction solution was added with 100 ml of water, and placed into a rotary evaporator to concentrate. The concentrated reaction solution was moved to a 1 L separatory funnel, added with 100 ml of water, and then extracted with ethyl acetate (100 ml×2). The organic phases were combined, dried over anhydrous sodium sulfate, and suction filtered. Silica gel powder was added to make a solid solution, which was then loaded on a chromatographic column and eluted with gradient eluent of 10% ethyl acetate/petroleum ether to 35% ethyl acetate/petroleum ether. Eluate was collected and the solvent was removed by evaporation to afford 15.0 g of compound

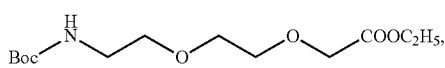

with a yield of 68.13%.
Compound

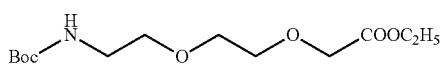

(15 g, 51.4862 mmol) was placed in a 500 ml round bottom flask, and 1,4-dioxane (100 ml) was added. Lithium hydroxide (5.28 g, 113.2697 mmol) was added under stirring, and water was added dropwise, until the solution became clear and yellow. After the reaction was complete, the reaction solution was placed into a rotary evaporator to concentrate. The concentrated reaction solution was moved to a 1 L separatory funnel, added with 50 ml of water, and extracted with n-hexane:ethyl ether 1:1 (200 ml×2). Aqueous phase was isolated, dropwise added with hydrochloric acid (1 mol/L) until pH=1, and extracted with ethyl acetate (100 ml×4). The organic phases were combined, dried over anhydrous sodium sulfate, suction filtered, water-removed with toluene, evaporated on a rotary evaporator to remove the solvent to afford Compound A-2.

Example 2-2

Preparation of

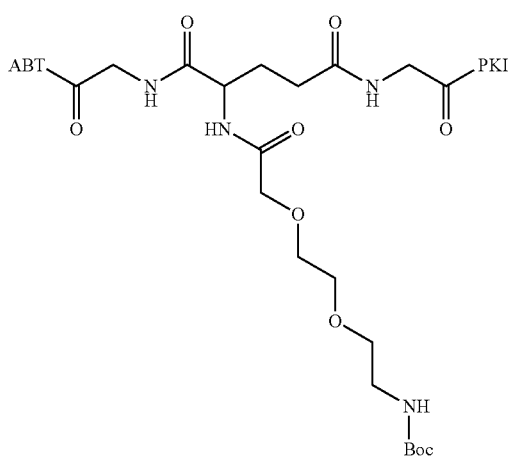

(B-2)

Compound I-1 (2.5 g, 2.3965 mmol), Compound A-2 (0.9458 g, 3.5974 mmol), HBTU (1.3633 g, 3.5974 mmol) and HOBT (0.4857 g, 3.5974 mmol) were added to a 500 ml round bottom flask, and dissolved in N,N-dimethylformamide (30 ml). The solution was cooled in a low- and constant-temperature reaction bath of 0° C. for 20 min, and then DIEA (1.9 ml, 10.7481 mmol) was slowly added dropwise. The reaction solution was moved to room temperature after 2 hours, and stirred overnight. After the reaction was complete, the reaction solution was moved to a 2 L round bottom flask. Anhydrous ethyl ether was added to precipitate, and then the ethyl ether phase was removed. The precipitate was dissolved in appropriate amount of methanol/dichloromethane, dried by suction filtration, dissolved in a solvent, loaded on a chromatographic column and eluted with eluent of 4% methanol/dichloromethane to 2% aqueous ammonia/4% methanol/dichloromethane to 3% aqueous ammonia/8% methanol/dichloromethane. Eluate was evaporated to remove the solvent, to afford 3.0 g of Compound B-2, with a yield of 97%.

Example 2-3

Preparation of

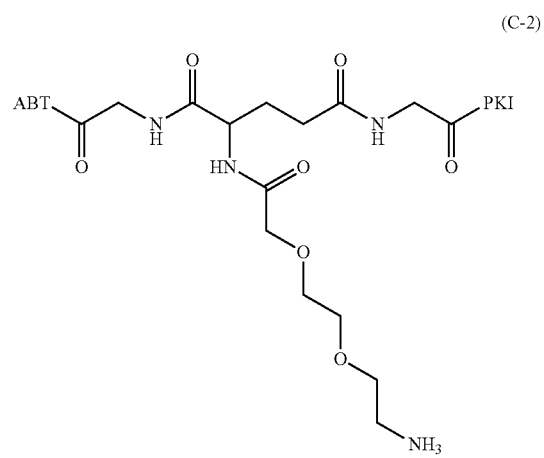

(C-2)

Compound B-2 (2.95 g, 2.2890 mmol) was added to a 500 ml round bottom flask, and dissolved in 20 ml of dichloromethane, and TFA (3.5 ml, 45.7932 mmol) was added under stirring. The reaction solution was stirred overnight at room temperature, and after the reaction was complete, the reaction solution was concentrated. Appropriate amount of methanol was added to dissolve crude product, and appropriate amount of sodium bicarbonate powder was added to neutralize excess TFA. After the neutralization, suction filtration was performed. Crude product was dissolved in a solvent, loaded on a chromatographic column and eluted with gradient eluent of 5% methanol/dichloromethane to 2% aqueous ammonia/6% methanol/dichloromethane to 3% aqueous ammonia/8% methanol/dichloromethane. Eluate was collected and evaporated to remove the solvent to afford 2.6229 g of Compound C-2, with a yield of 96.5%.

ITMS +c ESI Full ms [400.00-1800.00] [M+H$^+$]: 1188.78, [M+Na$^+$]: 1210.69.

$^1$H-NMR (400 Hz, DMSO-d$_6$) δ12.60-12.40 (m, 1H), 9.45-9.20 (m, 3H), 8.30-8.25 (m, 2H), 8.20-8.10 (m, 1H), 8.00-7.92 (m, 1H), 7.80-7.75 (m, 2H), 7.75-7.70 (m, 1H), 7.70-7.60 (m, 1H), 7.60-7.50 (m, 5H), 7.40-7.35 (m, 2H), 4.40-4.35 (m, 1H), 4.15-4.00 (m, 3H), 4.00-3.85 (m, 6H), 3.88-3.75 (m, 8H), 3.75-3.70 (m, 2H), 3.70-3.60 (m, 9H), 3.60-3.55 (m, 7H), 3.55-3.40 (m, 2H), 3.20-3.10 (m, 4H), 3.00-2.90 (m, 2H), 2.20-2.05 (m, 4H), 2.05-1.95 (m, 3H), 1.90-1.85 (m, 4H), 1.80-1.70 (m, 1H).

Example 2-4

Preparation of

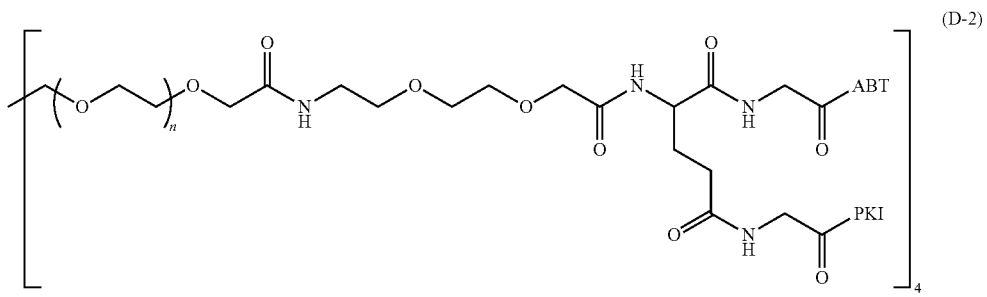

Compound C-2 (2.3766 g, 2 mmol) was added to a 200 ml round bottom flask, and dissolved in 15 ml of dichloromethane, and DMF (15 ml) was added to aid in solubilization. Macromolecule polyethylene glycol 4ARM-SCM-40K (10 g, 0.25 mmol, Beijing Jiankai) and magnetic stick were added, and stirred at 12 rpm. After the reaction was complete, the reaction solution was moved to a 2 L round bottom flask. Anhydrous ethyl ether was added to precipitate, and suction filtration was performed. Filtrate product was dissolved in dichloromethane, loaded on a chromatographic column and eluted with gradient eluent of dichloromethane to 5% methanol/dichloromethane to 4% aqueous ammonia/8% methanol/dichloromethane. Eluate was collected and evaporated to remove the solvent to afford 10.2 g of Compound D-2.

MALDI-TOF-MS [25000-60000] 42124-45870; highest peak: 44322

$^1$H-NMR (400 Hz, DMSO-$d_6$) δ 12.60-12.40 (m, 4H), 9.30-9.20 (m, 4H), 9.10-9.05 (m, 4H), 9.05-8.95 (m, 4H), 8.30-8.25 (m, 10H), 8.17-8.05 (m, 4H), 7.95-7.90 (m, 2H), 7.73-7.75 (m, 5H), 7.75-7.65 (m, 5H), 7.65-7.58 (m, 5H), 7.58-7.52 (m, 17H), 7.40-7.35 (m, 9H), 7.23-7.18 (m, 4H), 7.15-7.06 (m, 3H), 4.40-4.30 (m, 5H), 4.10-4.00 (m, 5H), 4.00-3.90 (m, 5H), 3.90-3.85 (m, 24H), 3.80-3.70 (m, 20H), 3.60-3.45 (m, 9130H), 3.45-3.40 (m, 44H), 3.40-3.35 (m, 64H), 3.20-3.15 (m, 4H), 3.06-2.85 (m, 9H), 2.40-2.30 (m, 15H), 2.05-1.95 (m, 12H), 1.80-1.70 (m, 9H).

Example 3

Synthesis of Intermediate Drug Having Synergistic Anticancer Activity as Shown by Formula I-3:

Example 3-1

Preparation of

Palbociclib (6.0 g, 13.4078 mmol, Beijing Isomersyn), Compound A-1 (2.8189 g, 16.0894 mmol), HBTU (7.6272 g, 20.1117 mmol) and HOBT (2.7191 g, 20.1117 mmol) were added to a 500 ml round bottom flask, and dissolved in N,N-dimethylformamide (75 ml). The solution was cooled in a low- and constant-temperature reaction bath of 0° C. for 20 min, and then DIEA (10.5 ml, 60.3351 mmol) was slowly added dropwise. The reaction solution was moved to room temperature after 2 hours, and stirred overnight. The reaction solution was poured into saturated NaHCO$_3$ solution (200 mL), and extracted by ethyl acetate (200 mL×2). The organic phases were combined, dried by anhydrous MgSO$_4$, suction filtered, and evaporated to remove the solvent, to afford 8.4 g of Compound (B-3)

with a yield of 100%.

Compound B-3 (8.1077 g, 13.4078 mmol) was added to a 300 ml round bottom flask, and dissolved in 80 ml of dichloromethane, and TFA (20.5 ml, 268.156 mmol) was added under stirring. The reaction solution was stirred overnight at room temperature, and after the reaction was complete, the reaction solution was concentrated. Appropriate amount of methanol was added to dissolve crude product, and appropriate amount of sodium bicarbonate powder was added to neutralize excess TFA. After the neutralization, suction filtration was performed. Appropriate amount of silica gel powder was added to the filtrate to make a solid solution, which was then loaded on a chromatographic column and eluted with gradient eluent of 1% methanol/dichloromethane to 2% methanol/dichloromethane, to 1% aqueous ammonia/4% methanol/dichloromethane to 5% aqueous ammonia/7% methanol/dichloromethane. Eluate was collected and evaporated to remove the solvent, to afford 5.0428 g of Compound C-3, with a yield of 75%.

Example 3-2

Preparation of

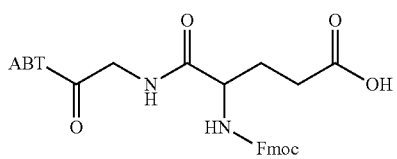
(E-3)

Compound C-3 (5.0428 g, 9.9917 mmol), Fmoc-protected tert-butyl glutamate (5.9520 g, 13.9884 mmol) and PyAOP (7.2933 g, 13.9884 mmol) were placed into a 300 ml round bottom flask, and then 100 ml of DMF was added. The solution was stirred for 30 min at −5° C. At the same condition, 2,4,6-trimethylpyridine (1.32 ml, 9.9917 mmol) was slowly added dropwise. After the addition of 2,4,6-trimethylpyridine was complete, the reaction continued for 2 h at low temperature, and then the reaction solution was moved to a freezer of 0° C. and stirred for 1 day. After the reaction was complete, the reaction solution was moved to a 2 L round bottom flask, and then about 500 ml of ethyl ether was added to precipitate. After precipitation, silica gel powder was added to make a solid solution, which was then loaded on a chromatographic column and eluted with gradient eluent of 1% methanol/dichloromethane to 7% methanol/dichloromethane. Eluate was collected and concentrated to afford 7.9 g of Compound

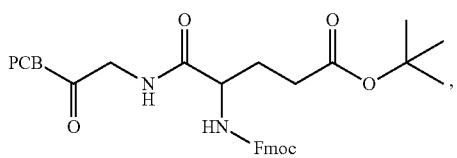
(D-3)

with a yield of 86.7%.

Compound D-3 (7.9 g, 8.6637 mmol) was added to a 500 ml round bottom flask, and dissolved in 80 ml of dichloromethane, and TFA (13.3 ml, 170.3274 mmol) was added under stirring. The reaction solution was stirred overnight at room temperature, and after the reaction was complete, the reaction solution was moved to a rotary evaporator to concentrate. The concentrate was dissolved in small amount of dichloromethane, and n-hexane was added to precipitate for three times, in order to remove majority of impurities. Appropriate amount of methanol was added to dissolve crude product, and appropriate amount of sodium bicarbonate powder was added to neutralize excess TFA. After the neutralization, suction filtration was performed. Filtrate was evaporated to remove the solvent to afford 7 g of Compound E-3, with a yield of 94.4%.

ITMS +c ESI Full ms [200.00-1600.00] [M+H$^+$]: 856.61, [M+Na$^+$]: 878.53, [M+K$^+$]: 894.52

$^1$H-NMR (400 Hz, DMSO-d$_6$) δ 12.30-11.85 (m, 1H), 10.30-10.20 (m, 1H), 9.00-8.95 (m, 1H), 8.10-8.05 (m, 1H), 8.05-7.95 (m, 1H), 7.85-7.80 (m, 1H), 7.75-7.70 (m, 2H), 7.65-7.60 (m, 1H), 7.60-7.50 (m, 1H), 7.50-7.40 (m, 2H), 7.40-7.30 (m, 2H), 5.90-5.75 (m, 1H), 4.15-4.05 (m, 2H), 4.05-3.95 (m, 1H), 3.25-3.15 (m, 3H), 2.65-2.60 (m, 2H), 2.45-2.40 (m, 4H), 2.35-2.30 (m, 5H), 2.28-2.15 (m, 2H), 2.00-1.83 (m, 3H), 1.82-1.70 (m, 4H), 1.65-1.52 (m, 2H), 1.30-1.20 (m, 1H).

Example 3-3

Preparation of

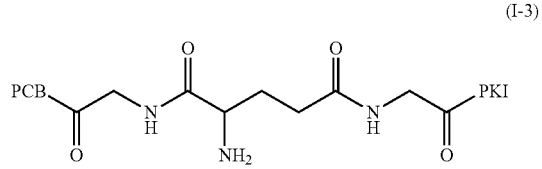
(I-3)

Compound E-3 (6.1075 g, 7.1349 mmol), Compound G-1 (2.5 g, 3.9639 mmol) and PyAOP (3.10 g, 5.9459 mmol) were placed into a 200 ml round bottom flask, and then 40 ml of DMF was added. The solution was stirred for 30 min at −5° C. At the same condition, 2,4,6-trimethylpyridine (0.52 ml, 3.9639 mmol) was slowly added dropwise. After the addition of 2,4,6-trimethylpyridine was complete, the reaction continued for 2 h at low temperature, and then the reaction solution was moved to a freezer of 0° C. and stirred for 1 day. The next day, 11-58 (0.5 g, 0.7928 mmol) and 2,4,6-trimethylpyridine (0.10 ml, 0.7928 mmol) were added. The reaction solution was moved to a freezer of 0° C. After the reaction was complete, the reaction solution was moved to a 2 L round bottom flask, and added with anhydrous ethyl ether to precipitate. Precipitate was dried by suction filtration, dissolved in a solvent, loaded on a chromatographic column, and eluted with gradient eluent of 3% methanol/dichloromethane to 6% methanol/dichloromethane, to 2% aqueous ammonia/5% methanol/dichloromethane to 3% aqueous ammonia/6% methanol/dichloromethane. Eluate was collected and concentrated to afford 1.5 g of Compound

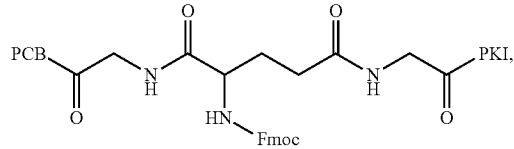
(H-3)

with a yield of 100%.

H-3 (6.4 g, 4.3606 mmol) was added to a 500 ml round bottom flask and dissolved in 15 ml of DMF, and morpholine (11.5 ml, 0.1308 mmol) was added under stirring and the mixture was stirred at room temperature for 3 hours. After the reaction was complete, the reaction solution was moved to a 2 L round bottom flask. Anhydrous ethyl ether was added to precipitate, and then the ethyl ether phase was removed. The precipitate was dissolved in appropriate amount of methanol/dichloromethane, dried in vacuo, dissolved in a solvent, loaded on a chromatographic column, and eluted with gradient eluent of 4% methanol/dichloromethane to 5% methanol/dichloromethane, to 2% aqueous ammonia/5% methanol/dichloromethane to 4% aqueous ammonia/8% methanol/dichloromethane. Eluate was evaporated to remove the solvent, to afford 5.9 g of Compound I-3, with a yield of 100%.

ITMS +c ESI Full ms [200.00-1600.00] [M+H$^+$]: 1246.82, [M+Na$^+$]: 1268.76

$^1$H-NMR (400 Hz, DMSO-d$_6$) δ 10.20-10.00 (m, 1H), 9.10-9.00 (m, 1H), 9.05-8.90 (m, 2H), 8.35-8.25 (m, 2H), 8.10-8.00 (m, 2H), 7.90-7.80 (m, 1H), 7.60-7.45 (m, 5H), 7.45-7.35 (m, 2H), 5.85-5.80 (m, 1H), 4.17-4.12 (m, 1H), 4.06-4.02 (m, 1H), 4.00-3.97 (m, 1H), 3.97-3.90 (m, 2H), 3.90-3.70 (m, 8H), 3.70-3.55 (m, 13H), 3.55-3.40 (m, 8H), 3.30-3.27 (m, 3H), 3.25-3.20 (m, 3H), 3.15-3.10 (m, 2H), 2.30-2.20 (m, 4H), 1.95-1.85 (m, 3H), 1.84-1.72 (m, 3H), 1.70-1.50 (m, 3H).

Example 4

Synthesis of Polyethylene Glycol-Coupled Synergistic Anticancer Drug or Derivative Thereof as Shown by Formula C-4:

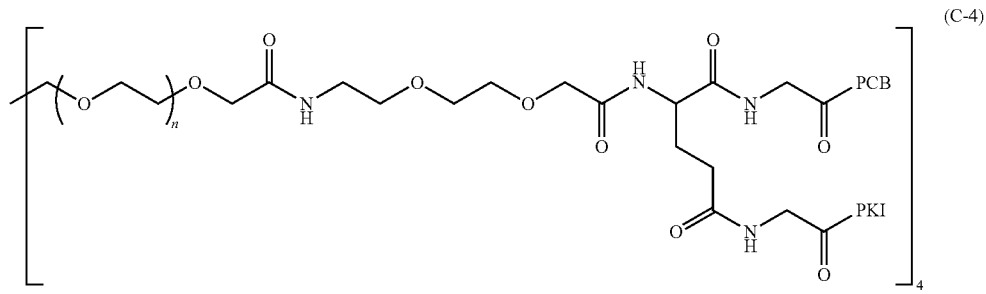

Example 4-1

Preparation of

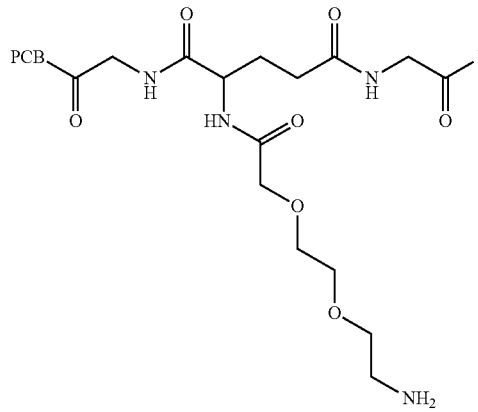

(B-4)

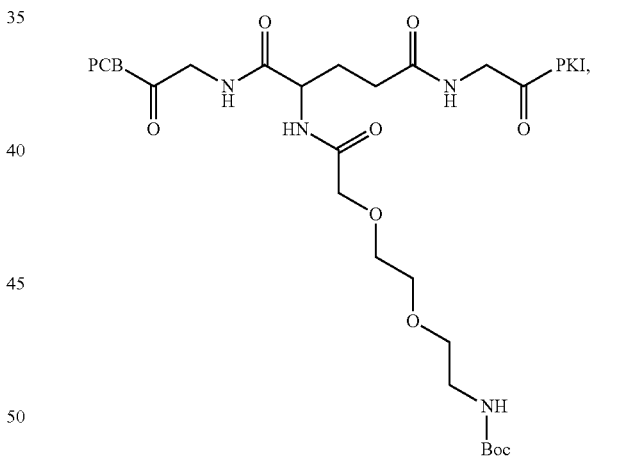

(A-4)

Compound I-3 (5.8 g, 4.6564 mmol), Compound A-2 (1.8376 g, 6.9846 mmol), HBTU (2.4688 g, 6.9846 mmol) and HOBT (1.3086 g, 6.9846 mmol) were added to a 500 ml round bottom flask, and dissolved in N,N-dimethylformamide (50 ml). The solution was cooled in a low- and constant-temperature reaction bath of 0° C. for 20 min, and then DIEA (3.65 ml, 20.9538 mmol) was slowly added dropwise. After 2 hours, the reaction solution was moved to room temperature, and stirred overnight. After the reaction was complete, the reaction solution was moved to a 2 L round bottom flask. Anhydrous ethyl ether was added to precipitate, and then the ethyl ether phase was removed. The precipitate was dissolved in appropriate amount of methanol/dichloromethane, dried in vacuo, dissolved in a solvent, loaded on a chromatographic column, and eluted with gradient eluent of 4% methanol/dichloromethane, to 2% aqueous ammonia/4% methanol/dichloromethane to 3% aqueous ammonia/8% methanol/dichloromethane. Eluate was evaporated to remove the solvent to afford 6.2 g of Compound with a yield of 89.8%.

Compound A-4 (6.1 g, 4.0893 mmol) was added to a 500 ml round bottom flask, and dissolved in 20 ml of dichloromethane, and TFA (6.3 ml, 81.7859 mmol) was added under stirring. The reaction solution was stirred overnight at room temperature, and after the reaction was complete, the reaction solution was concentrated. Appropriate amount of methanol was added to dissolve crude product, and appropriate amount of sodium bicarbonate powder was added to neutralize excess TFA. After the neutralization, suction filtration was performed. The filtration product was dissolved in a solvent, loaded on a chromatographic column and eluted with gradient eluent of 5% methanol/dichloromethane, to 2% aqueous ammonia/5% methanol/dichloromethane to 4% aqueous ammonia/8% methanol/dichloromethane. Eluate was collected and evaporated to remove the solvent to afford 4.9 g of Compound B-4, with a yield of 86%.

ITMS +c ESI Full ms [300.00-1600.00] [M+H$^+$]: 1391.84, [M+Na$^+$]: 1413.77

$^1$H-NMR (400 Hz, DMSO-d$_6$) δ 10.15-10.05 (m, 1H), 9.15-9.05 (m, 1H), 9.05-8.90 (m, 2H), 8.35-8.20 (m, 3H), 8.10-8.00 (m, 2H), 7.75-7.60 (m, 2H), 7.60-7.55 (m, 4H), 7.45-7.30 (m, 2H), 5.85-5.80 (m, 1H), 4.45-4.35 (m, 1H), 4.25-4.10 (m, 1H), 4.10-3.90 (m, 4H), 3.90-3.85 (m, 3H), 3.85-3.70 (m, 7H), 3.70-3.55 (m, 29H), 3.40-3.35 (m, 6H), 3.30-3.25 (m, 3H), 3.25-3.10 (m, 3H), 2.60-2.57 (m, 1H), 2.45-2.40 (m, 2H), 2.35-2.30 (m, 2H), 2.30-2.18 (m, 3H), 2.05-1.75 (m, 5H), 1.65-1.45 (m, 2H).

Example 4-2

Preparation of

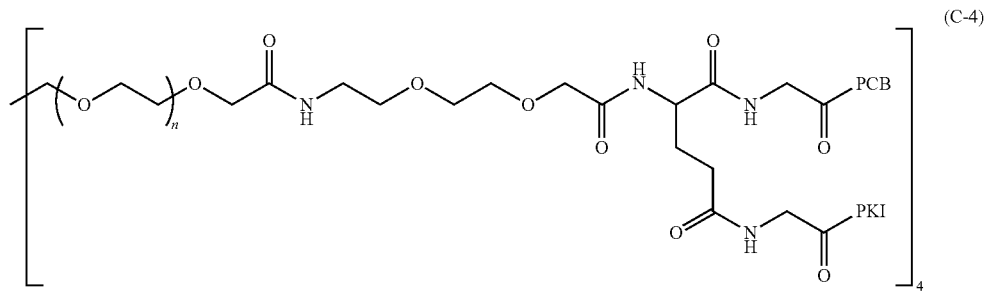

(C-4)

Compound A-4 (2.7832 g, 2 mmol) was added to a 200 ml round bottom flask and dissolved in 15 ml of dichloromethane, and DMF (15 ml) was added to aid in solubilization. Macromolecule 4ARM-SCM-40K (10 g, 0.25 mmol, Beijing Jiankai) and magnetic stick were added and slowly stirred. After the reaction was complete, the reaction solution was moved to a 2 L round bottom flask, added with anhydrous ethyl ether to precipitate, and suction filtered. The filtrate product was dissolved in dichloromethane, loaded on a chromatographic column, and eluted with gradient eluent of dichloromethane to 5% methanol/dichloromethane, to 4% aqueous ammonia/8% methanol/dichloromethane. Eluate was collected and evaporated to remove the solvent to afford 10.8 g of Compound C-4.

MALDI-TOF-MS [25000-60000] 45172-48292, highest peak: 46670

$^1$H-NMR (400 Hz, DMSO-d$_6$) δ10.15-10.05 (m, 4H), 9.15-9.05 (m, 4H), 9.05-8.90 (m, 8H), 8.35-8.25 (m, 12H), 8.10-8.05 (m, 8H), 7.90-7.85 (m, 4H), 7.75-7.62 (m, 8H), 7.60-7.50 (m, 16H), 7.40-7.30 (m, 8H), 5.90-5.80 (m, 4H), 4.45-4.35 (m, 5H), 4.20-4.10 (m, 6H), 4.10-3.95 (m, 16H), 3.95-3.85 (m, 26H), 3.85-3.70 (m, 38H), 3.70-3.60 (m, 78H), 3.60-3.58 (m, 39H), 3.58-3.40 (m, 3559H), 3.40-3.35 (m, 25H), 3.25-3.10 (m, 14H), 2.30-2.20 (m, 13H), 2.00-1.70 (m, 22H), 1.65-1.53 (m, 8H).

Example 5

Synthesis of Intermediate Drug Having Synergistic Anticancer Activity as Shown by Formula I-5:

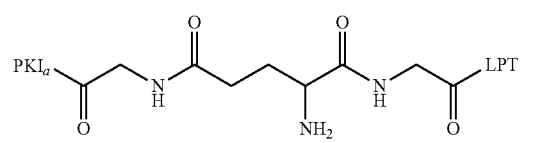

(I-5)

The synthesis route was shown in FIG. 1.

Example 5-1

Preparation of

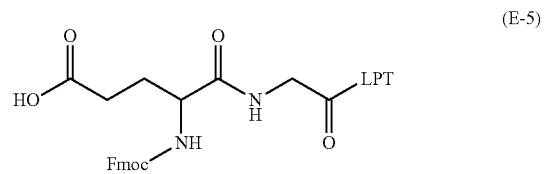

(E-5)

Compound A-1 (3.0148 g, 17.2099 mmol), lapatinib (10 g, 17.2099 mmol, Wuhan Yuancheng Gongchuang Technology Co., LTD), HBTU (9.6881 g, 25.8149 mmol) and HOBT (3.4881 g, 25.8149 mmol) were added to a 500 ml round bottom flask, and dissolved in DMF (150 mL). Solution was cooled in a low- and constant-temperature reactor of −5° C. for 20 min, and then DIEA (13.4902 mL, 77.4447 mmol) was slowly added dropwise. After being reacted for 2 h, the solution was moved to room temperature and stirred overnight. After the reaction was complete, the reaction solution was moved to 2 L separatory funnel, added with 300 ml of saturated NaHCO$_3$ solution, and then extracted by ethyl acetate three times. The organic phases were combined, and washed by saturated NaHCO$_3$ solution and saturated saline respectively one time. The organic phase was dried over anhydrous MgSO$_4$, suction filtered, and then concentrated under reduced pressure to afford 12.70 g of compound

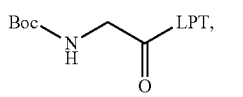
(B-5)

with a yield of 100%.

Compound B-5 (12.7 g, 17.2099 mmol) was placed into a round bottom flask, and dissolved in 50 ml of $CH_2Cl_2$, and TFA (26.4 mL, 344.1985 mmol) was added under stirring. The solution was stirred overnight at room temperature. After the reaction was complete, the solution was concentrated under reduced pressure, and the residue was dissolved in appropriate amount of anhydrous methanol. $NaHCO_3$ solid powder was added to neutralize the remaining of TFA. After neutralization, the solution was filtered, and appropriate amount of silica gel powder was added to the filtrate to make a solid solution, which was loaded on a chromatographic column and eluted with 5% methanol/dichloromethane, followed by elution with gradient eluent of 2.5% aqueous ammonia/7% methanol/dichloromethane to 5% aqueous ammonia/10% methanol/dichloromethane. Eluate was collected and concentrated under reduced pressure, to afford 10.98 g of Compound

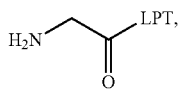
(C-5)

with a yield of 99.6%.

Compound C-5 (9 g, 14.1013 mmol), Fmoc-protected tert-butyl glutamate (8.40 g, 19.7418 mmol) and PyAOP (10.2930 g, 19.7418 mmol) were placed into a 1 L round bottom flask, and then 260 ml of DMF was added. The solution was stirred for 30 min at −5° C. At the same condition, 2,4,6-trimethylpyridine (1.86 ml, 14.1013 mmol) was slowly added dropwise. After the addition of 2,4,6-trimethylpyridine was complete, the reaction continued for 2 h at low temperature, and then the reaction solution was moved to a freezer of 0° C. and stirred for 2 days. After the reaction was complete, the reaction solution was moved to a 1 L separatory funnel, added with about 300 ml of saturated saline, and extracted by ethyl acetate three times. The organic phases were combined, and washed two times by saturated saline. The organic phases were combined and concentrated. The residue was dissolved in appropriate amount of dichloromethane, loaded on a chromatographic column, and eluted with dichloromethane, followed by elution with gradient eluent of 1% methanol/dichloromethane to 6% methanol/dichloromethane. Eluate was collected and concentrated to afford 14.7 g of Compound

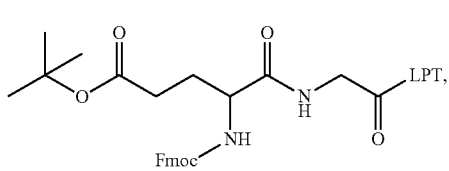
(D-5)

with a yield of 99%.

Compound D-5 (14.7 g, 28.6884 mmol) was added to a flask, dissolved in 100 ml of dichloromethane, and stirred at room temperature, and then trifluoroacetic acid (TFA) (44 mL, 573.7674 mmol) was slowly added dropwise under stirring and stirred overnight at room temperature. After the reaction was complete, the solvent in the reaction mixture was removed by evaporation on a rotary evaporator. The dry crude product was dissolved in dichloromethane, and precipitated by n-hexane, and then the n-hexane phase was removed; the operation was repeated three times, in order to remove majority of impurities. The product was collected and concentrated under reduced pressure to afford 13.9 g of Compound E-5, with a yield of 99.6%.

ITMS −c ESI Q 1MS [200.00-1100.00] [M−H$^+$]: 987.41
ITMS +c ESIQ 1MS [200.00-1100.00] [M+H$^+$]: 989.32

Example 5-2

The Process for Preparing De-Terminal-Dimethyl PKI-587 (i.e. $PKI_a$):

P-5 (4.2 g, 8.31 mmol) was added to a reaction bottle, and then NMP (40 ml) was added, and DIEA (6.44 g, 49.86 mmol) and HBTU (15.76 g, 41.35 mmol) were sequentially added. The mixture was stirred for 1 hour at room temperature to dissolve. Tert-butyl piperidin-4-yl carbamate (6.66 g, 33.23 mmol) was added, and reacted for 3 nights at room temperature. After the reaction was complete, water and DCM were added, making the mixture layered, and the aqueous layer was extracted twice by DCM. The organic phases were combined, washed with water four times, washed with saturated sodium bicarbonate aqueous solution and saturated saline one time respectively, dried over anhydrous magnesium sulfate, and concentrated under reduced pressure to afford oily substances. 42 ml of methanol was added at room temperature, followed by crystallization for half an hour and filtration. Filtrate was dried to afford 4.2 g of light red solid, with a yield of 73.5%.

ITMS +c ESI Full ms [150.00-1200.00] [M+H$^+$] 688.35.

The light red solid above (3 g, 4.36 mmol) was added to a reaction bottle, and then 45 ml of dioxane was added, and 5 M HCl (15 ml) was added dropwise in an ice bath. After the addition of HCl was complete, the reaction continued for 48 h at room temperature. After the reaction was complete, the reaction mixture was filtered. Filter cake was washed with sodium bicarbonate solution and washed with methanol to afford a white solid, which was then dried in vacuo to afford 2.2 g of $PKI_a$, with a yield of 85%.

$^1$H-NMR (400 Hz, DMSO-d$_6$) δ 9.60-9.40 (m, 2H), 8.45-8.25 (m, 2H), 7.80-7.60 (m, 1H), 7.60-7.51 (m, 4H), 7.40-7.25 (m, 2H), 4.00-3.55 (m, 18H), 3.40-2.98 (m, 3H), 1.90-1.60 (m, 2H), 1.50-1.30 (m, 3H) ITMS +c ESI Full ms [150.00-1200.00] [M+H$^+$] 588.37.

Example 5-3

Preparation of

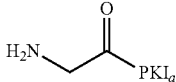
(G-5)

$PKI_a$ (1 g, 1.7027 mmol), Compound A-1 (328.11 mg, 1.8730 mmol), HBTU (958.51 mg, 2.5541 mmol) and HOBT (345.10 mg, 2.5541 mmol) were placed into a 500 ml round bottom flask, and then 15 ml of DMF was added. The solution was stirred at −5° C. At the same condition, DIEA (1.33 ml, 7.6622 mmol) was slowly added dropwise. After DIEA was added, the reaction continued for 2 h at low temperature, and then the reaction solution was moved to room temperature and stirred overnight. After the reaction was complete, the reaction solution was moved to a 2 L separatory funnel, added with 200 ml of saturated sodium bicarbonate solution, and extracted by ethyl acetate three times. The organic phases were combined, and washed by saturated saline twice. The organic phases were combined, dried over anhydrous magnesium sulfate, filtered, and filtrate was evaporated to remove the solvent. The residue was dissolved in appropriate amount of dichloromethane, loaded on a chromatographic column, and eluted with gradient eluent of 3% methanol/dichloromethane to 8% methanol/dichloromethane. Eluate was collected and concentrated, to afford 1.6293 g of compound

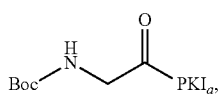
(F-5)

with a yield of 100%.

Compound F-5 (500 mg, 0.6716 mmol) was placed into a 200 ml round bottom flask, and dissolved in about 10 ml of dichloromethane, and TFA (0.5 ml, 6.716 mmol) was added under stirring. The reaction solution was stirred overnight at room temperature, and after the reaction was complete, the reaction solution was concentrated. Appropriate amount of methanol was added to dissolve crude product, and appropriate amount of sodium bicarbonate powder was added to neutralize excess TFA. After the neutralization, suction filtration was performed, and filtrate was concentrated to dryness. The residue was dissolved in appropriate amount of dichloromethane, loaded on a chromatographic column, and eluted with gradient eluent of 4% methanol/dichloromethane to 7% methanol/dichloromethane followed by elution with gradient eluent of 3% aqueous ammonia/6% methanol/dichloromethane to 4% aqueous ammonia/8% methanol/dichloromethane. Eluate was collected and concentrated by evaporation to remove the solvent, resulting in 360 mg of Compound G-5, with a yield of 84%.

Example 5-4

Preparation of

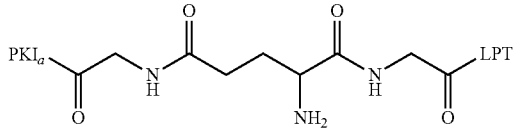
(I-c)

Compound G-5 (2 g, 3.1011 mmol), Compound E-5 (3.3761 g, 3.4112 mmol) and PyAOP (2.2643 g, 4.3429 mmol) were placed into a 100 mL round bottom flask, and then 50 ml of DMF was added. The solution was stirred for 30 min at −5° C. At the same condition, 2,4,6-trimethylpyridine (0.41 ml, 3.1011 mmol) was slowly added dropwise. After the addition of 2,4,6-trimethylpyridine was complete, the reaction continued for 2 h at low temperature, and then the reaction solution was stirred overnight at −2° C. After the reaction was complete, the reaction solution was precipitated by anhydrous ethyl ether, and then the ethyl ether phase was removed, and the precipitation was repeated twice. The precipitate was dissolved in appropriate amount of dichloromethane, loaded on a chromatographic column, and eluted with gradient eluent of 2% methanol/dichloromethane to 8% methanol/dichloromethane, followed by elution with 3% aqueous ammonia/8% methanol/dichloromethane. Eluate was collected and concentrated to afford 4 g of Compound H-5, with a yield of 100%.

Compound H-5 (4 g, 2.4745 mmol) was placed into a 500 ml round bottom flask and dissolved in about 20 ml of DMF, and morpholine (6.5 ml, 74.2364 mmol) was added under stirring. The reaction solution was stirred at room temperature for 3 h. After the reaction was complete, the reaction solution was precipitated by ethyl ether to remove large quantity of impurities detected at ultraviolet wavelength, and the ethyl ether phase was removed. Precipitate was dissolved in a mixture of methanol and dichloromethane, loaded on a chromatographic column, and eluted with gradient eluent of 3% methanol/dichloromethane to 8% methanol/dichloromethane, followed by elution with 3% aqueous ammonia/8% methanol/dichloromethane. Eluate was collected and concentrated by evaporation to remove the solvent to afford 2.23 g of Compound I-5, with a yield of 70%.

$^1$H-NMR (400 Hz, DMSO-d$_6$) δ 9.95-9.85 (m, 1H), 9.10-9.00 (m, 1H), 8.97-8.88 (m, 1H), 8.76-8.70 (m, 1H), 8.60-8.50 (m, 1H), 8.40-8.33 (m, 1H), 8.32-8.25 (m, 2H), 8.24-8.16 (m, 1H), 8.05-7.95 (m, 2H), 7.92-7.83 (m, 1H), 7.82-7.78 (m, 1H), 7.75-7.65 (m, 1H), 7.59-7.43 (m, 5H), 7.37-7.25 (m, 4H), 7.21-7.15 (m, 1H), 7.15-7.03 (m, 1H), 6.70-6.55 (m, 1H), 5.35-5.20 (m, 2H), 4.80-4.64 (m, 2H), 4.40-4.10 (m, 3H), 3.90-3.65 (m, 13H), 3.64-3.58 (m, 9H), 3.40-3.32 (m, 2H), 3.10-3.00 (m, 3H), 2.28-2.10 (m, 2H), 1.90-1.67 (m, 6H), 1.65-1.56 (m, 1H), 1.40-1.28 (m, 2H)

ITMS +c ESI Full ms [200.00-2000.00] [M+H$^+$]: 1394.38

Example 6 Synthesis of polyethylene glycol-coupled synergistic anticancer drug or derivative thereof as shown by formula F-6:

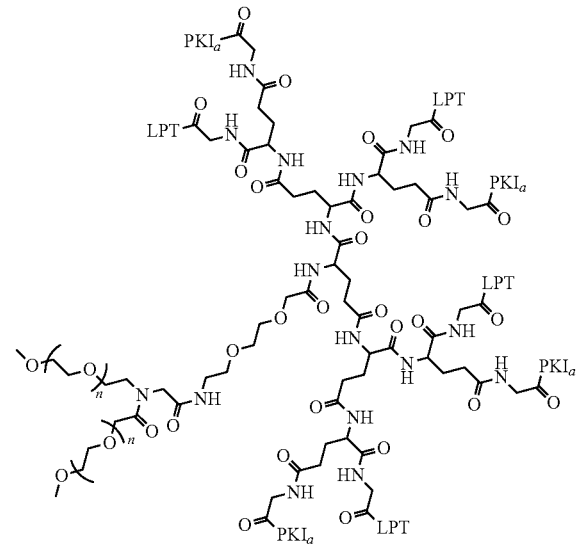
(F-6)

Figure 2:
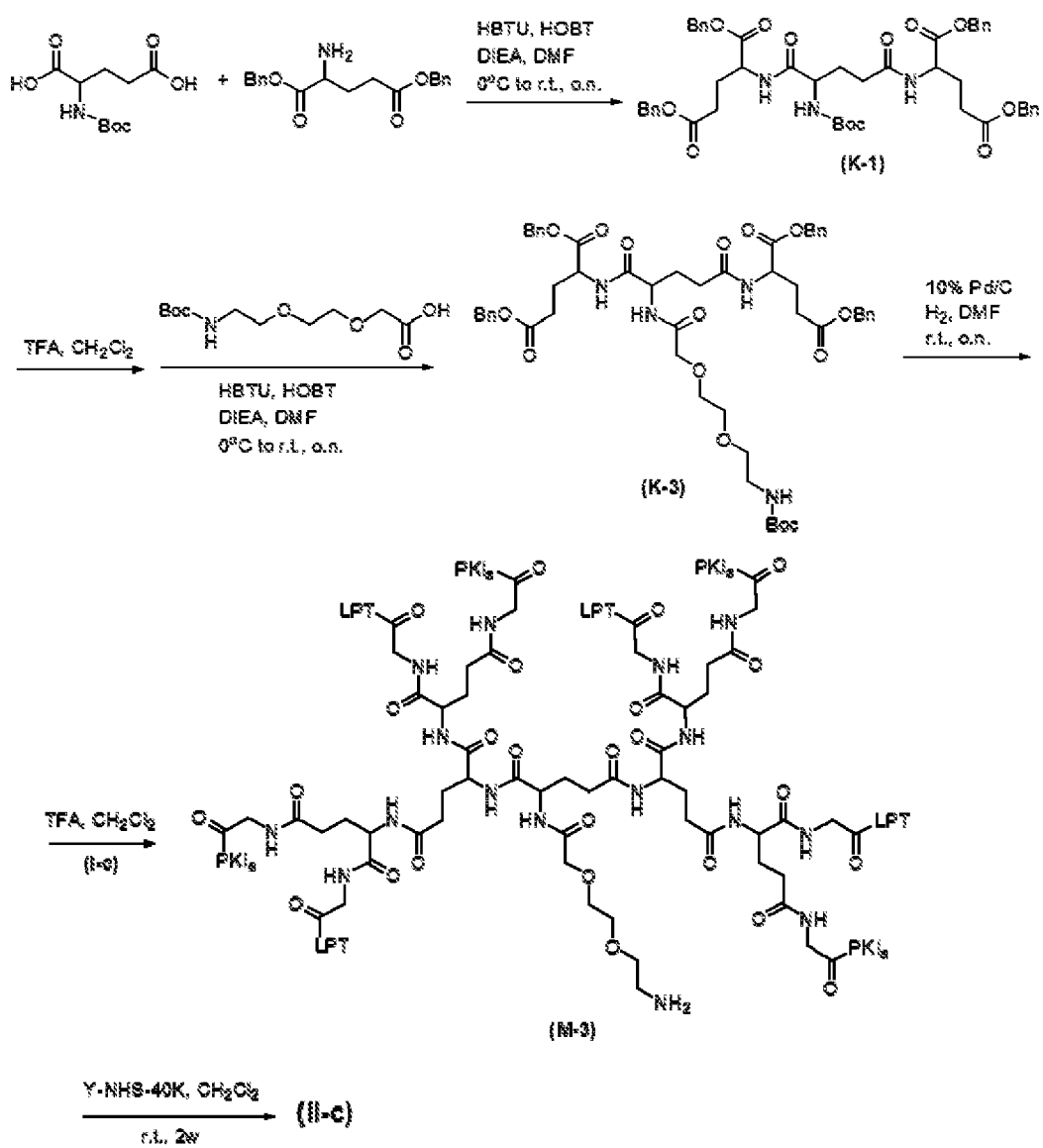
FIG. 2 is a scheme of synthesis route of the compound II-c provided in Example 6.

Synthesis route was shown in FIG. 2.

Example 6-1

Preparation of

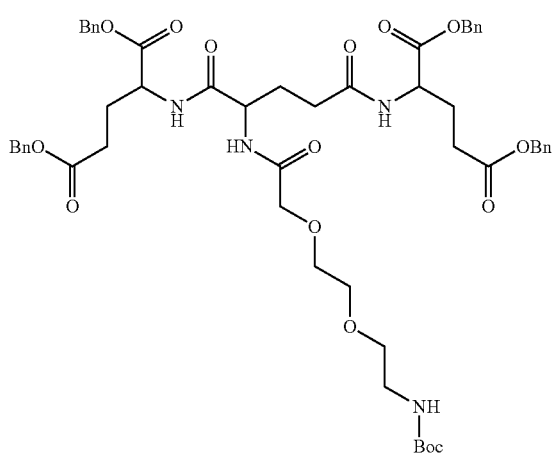

(C-6)

The mixture of dibenzyl glutamate (42.0 g, 128.2795 mmol), Boc-protected glutamic acid (14.4122 g, 58.3089 mmol), HBTU (65.6482 g, 174.9266 mmol) and HOBT (23.6361 g, 174.9266 mmol) were dissolved in DMF (300 mL), and cooled in a low- and constant-temperature reaction bath of −5° C. for 30 min. DIEA (91.41 mL, 524.7799 mmol) was added dropwise. After DIEA was added, the reaction continued in a reaction bath of −5° C. for 1 hour, and then reaction bottle was moved to room temperature. The reaction continued for two days, and then the reaction mixture was moved to saturated sodium bicarbonate solution (400 mL), and extracted by ethyl acetate (300 mL×3). The organic phases were combined, washed by saturated sodium bicarbonate solution twice (200 mL×2), dried over magnesium sulfate and concentrated. The concentrate was purified on a chromatography silica gel column with an eluent of 10%-50% ethyl acetate-petroleum ether, resulting in 16.1 g of

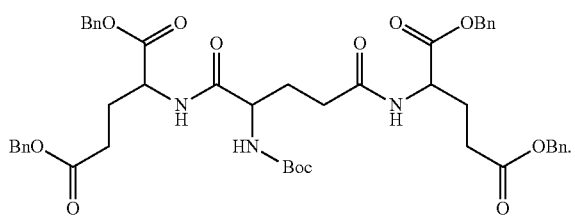

(A-6)

Compound A-6 (16 g, 18.4760 mmol) was placed into a 500 ml round bottom flask, and then about 50 mL of dichloromethane was added to dissolve, and TFA (14.2 mL, 184.7596 mmol) was added under stirring. The reaction solution was stirred overnight at room temperature, and then concentrated on a rotary evaporator, in order to remove large quantity of TFA. The crude product was dissolved in methanol, added with NaHCO$_3$ solid powder, neutralized, filtered. The filtrate was concentrated, dried, and purified by column chromatography with eluent of 10%-90% ethyl acetate-petroleum ether and 5% methanol-ethyl acetate, resulting in 24 g of compound

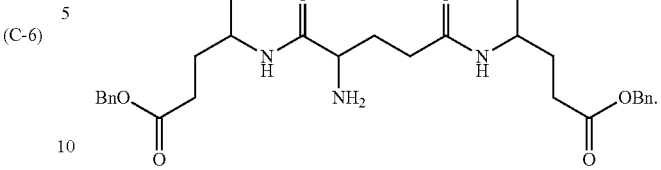

(B-6)

Compound B-6 (14 g, 18.2796 mmol), BocNHCH$_2$CH$_2$OCH$_2$CH$_2$OCH$_2$COOH (7.2113 g, 27.4194 mmol), HBTU (13.7203 g, 76.5593 mmol) and HOBT (4.9399 g, 36.5593 mmol) were placed into a 500 ml round bottom flask, dissolved in DMF (150 mL), and stirred at −5° C. for 20 min, and then DIEA (19.10 mL, 109.6778 mmol) was slowly added dropwise. After the addition of DIEA, the reaction continued at −5° C. for 2 hours and kept at room temperature and stirred overnight. The reaction solution was added in saturated NaHCO$_3$ solution (300 mL) and extracted by ethyl acetate (500 mL). Organic phase was dried over magnesium sulfate, filtered, concentrated, and was purified on a silica gel column with 15%-60% ethyl acetate-petroleum ether and 4%-5% methanol-ethyl acetate, resulting in 7.5 g of

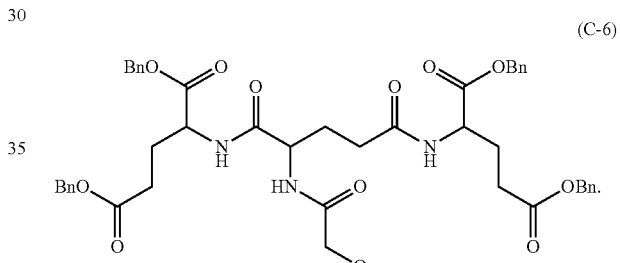

(C-6)

Example 6-2

Preparation of Compound E-6, of which the structure is shown in FIG. 2.

Compound I-5 (2.23 g, 1.6014 mmol), Compound C-6 (0.2588 g, 0.4 mmol), HBTU (0.9 g, 2.4 mmol) and HOBT (0.3243 g, 2.4 mmol) were placed into a 500 ml round bottom flask, and then 30 ml of DMF was added. The solution was stirred for 30 min at −5° C. At the same condition, DIEA (1.25 ml, 7.2 mmol) was slowly added dropwise. After the addition of DIEA, the reaction continued for 2 h at low temperature, and then the reaction solution was stirred overnight at −2° C. After the reaction was complete, the reaction solution was precipitated by anhydrous ethyl ether, and then the ethyl ether phase was removed, and the precipitation was repeated twice. The precipitate was dissolved in appropriate amount of methanol and dichloromethane, and appropriate amount of silica gel powder was added to make a solid solution, which was then loaded on a chromatographic column, eluted with 2% dichloromethane, and eluted with 3% aqueous ammonia/7% methanol/dichloromethane to 5% aqueous ammonia/9% methanol/dichloromethane. Eluate was collected and concentrated to afford 1.6 g of E-6 with Boc-protected amino group, i.e. Compound D-6, with a yield of 72%.

Compound D-6 (1.4 g, 0.2277 mmol) was placed into a 200 ml round bottom flask, and about 15 ml of dichloromethane was added to dissolve, and TFA (0.52 ml, 6.8314 mmol) was added under stirring. The reaction solution was stirred overnight at room temperature, and after the reaction was complete, the reaction solution was concentrated by a rotary evaporator, in order to remove large quantity of TFA. The concentrate was dissolved in methanol and dichloroethanol, and the remaining of TFA was neutralized with solid sodium bicarbonate. After neutralization and filtration, appropriate amount of silica gel powder was added to the filtrate to make a solid solution, which was loaded on a chromatographic column, eluted firstly with 200 ml of dichloromethane and then isocratic-eluted with 5% methanol/dichloromethane. Appropriate amount of methanol was added to dissolve the crude product, and appropriate amount of sodium bicarbonate powder was added to neutralize excess TFA. After the neutralization, suction filtration was performed, and appropriate amount of silica gel powder was added to the filtrate to make a solid solution, which was loaded on a chromatographic column, and eluted with gradient eluent of 2% aqueous ammonia/5% methanol/dichloromethane to 3% aqueous ammonia 8% methanol/dichloromethane. Eluate was collected, concentrated by evaporation to remove the solvent, to afford 1.09 g of Compound E-6, with a yield of 80%.

$^1$H-NMR (400 Hz, DMSO-d$_6$) δ 9.95-9.75 (m, 4H), 9.20-9.06 (m, 5H), 89.06-8.95 (m, 4H), 8.80-8.69 (m, 4H), 8.64-8.50 (m, 4H), 8.35-8.15 (m, 14H), 8.15-8.06 (m, 3H), 8.05-7.98 (m, 7H), 7.94-7.85 (m, 4H), 7.85-7.75 (m, 5H), 7.75-7.66 (m, 4H), 7.64-7.42 (m, 20H), 7.40-7.22 (m, 19H), 7.20-7.12 (m, 4H), 7.10-7.00 (m, 3H), 6.72-6.65 (m, 2H), 6.60-6.50 (m, 2H), 6.50-6.40 (m, 3H), 5.35-5.15 (m, 8H), 4.85-4.65 (m, 8H), 4.40-4.00 (m, 26H), 4.00-3.72 (m, 46H), 3.71-3.53 (m, 45H), 3.52-3.48 (m, 3H), 3.45-3.40 (m, 4H), 3.200-3.15 (m, 16H), 3.10-2.95 (m, 14H), 2.30-2.10 (m, 8H), 2.05-1.85 (m, 6H), 1.85-1.65 (m, 14H)

MALDI-TOF MS [5500-6500] [M+H$^+$]: 6052, [M+Na$^+$]: 6079

Example 6-3

Preparation of Compound F-6

Compound E-6 (1.09 g, 0.1802 mmol) was added to a 200 ml round bottom flask, and then about 30 ml of dichloromethane and 10 ml of DMF were added to dissolve compound M-3, and Y-NHS-40K (5.0466 g, 0.1201 mmol) was added. The reaction solution was stirred at room temperature in dark. After the reaction was complete, the solution was precipitated by anhydrous ethyl ether, and filtered. The filter cake was dissolved in dichloromethane, loaded on a chromatographic column, and eluted with the following eluents sequentially: dichloromethane, 5% methanol/dichloromethane, and 3% aqueous ammonia/8% methanol/dichloromethane, to afford 5.7 g of F-6.

MALDI-TOF MS: 41503-43007

Example 7

Synthesis of Intermediate Drug Having Synergistic Anti-cancer Activity as Shown by Formula D-7:

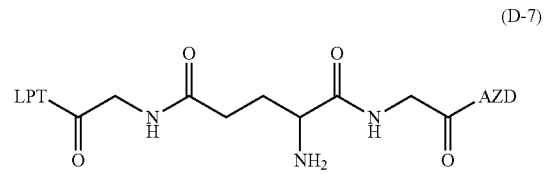

(D-7)

Figure 3:
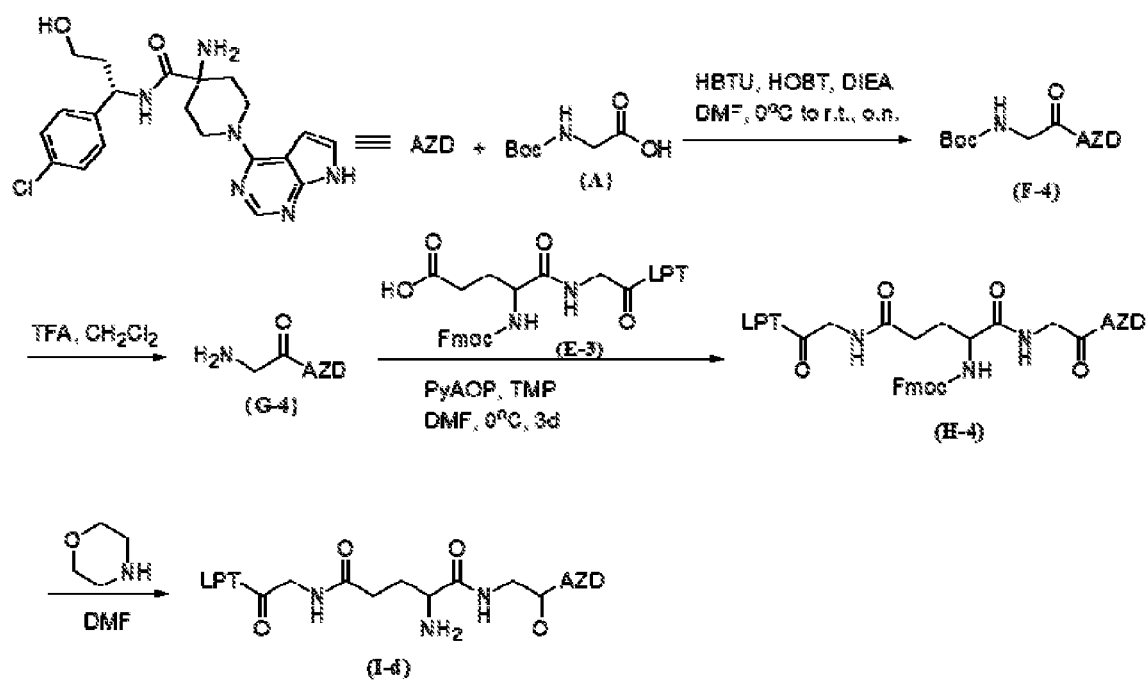
FIG. 3 is a scheme of synthesis route of the compound I-d provided in Example 7.

Synthesis route was shown in FIG. 3.

Example 7-1

Preparation of

(B-7)

AZD5363 (100 mg, 0.2335 mmol, Shanghai LouLan), Boc-Gly (40.9041 mg, 0.2335 mmol), HBTU (131.4439 mg, 0.3502 mmol) and HOBT (47.3253 mg, 0.3502 mmol) were placed into a 100 mL round bottom flask, and then dissolved in DMF (6 ml). The solution was stirred for 30 min at −5° C., and then DIEA (0.183 ml, 1.0507 mmol) was slowly added dropwise. After the addition of DIEA, the solution was reacted for 2 h at low temperature, and then the reaction temperature was increased to 0° C. and the reaction solution was stirred overnight. After the reaction was complete, the reaction solution was moved to a 0.25 L separatory funnel, added with 30 ml of saturated sodium bicarbonate solution, and then extracted by ethyl acetate twice (20 ml×2). The organic phases were combined, and washed by saturated sodium bicarbonate solution twice (20 ml×2 l). The organic phases were combined, dried by anhydrous sodium sulfate and suction filtered. The filtrate was concentrated, loaded on a chromatographic column, and eluted with gradient eluent of 3% methanol/ethyl acetate to 4% methanol/ethyl acetate, followed by elution with 4% triethylamine/methanol/ethyl acetate. Eluate was collected and concentrated to afford 75.8 mg of Compound A-7, with a yield of 56%.

ITMS +c ESI Full MS [200.00-1100.00] [M+H$^+$]: 586.31, [M+Na$^+$]: 608.27

Compound A-7 (1 g, 1.7080 mmol) was added to a 100 mL round bottom flask and dissolved in dichloromethane (15 mL), and then TFA (2.6 mL, 34.1618 mmol) was added. The reaction solution was stirred overnight at room temperature. After the reaction was complete, the reaction solution was concentrated and dried under reduced pressure, and then the residue was dissolved in appropriate amount of methanol. Sodium bicarbonate solid powder was added under stirring to neutralize the remaining of TFA. After the neutralization, the solution was filtered, and appropriate amount of silica gel powder was added to the filtrate to make a solid solution, which was loaded on a chromatographic column and eluted with gradient eluent of 2% aqueous ammonia/5% methanol/dichloromethane to 4% aqueous ammonia/9% methanol/dichloromethane. Eluate was collected, concentrated by evaporation to remove the solvent to afford 763.8 mg of Compound B-7, with a yield of 100%.

ITMS +c ESI Full MS [120.00-1000.00] [M+H$^+$]: 486.20, [M+Na$^+$]: 508.17

Example 7-2

Preparation of

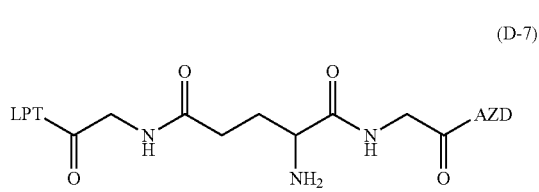
(D-7)

Compound B-7 (83.58 mg, 0.1722 mmol), Compound E-3 (170.4 mg, 0.1722 mmol), PyAOP (125.7 mg, 0.2410 mmol) were placed into a 25 ml round bottom flask, and then DMF (3 ml) was added to dissolve. The solution was stirred for 30 min at −5° C. At the same condition, 2,4,6-trimethylpyridine (0.06 ml, 0.1722 mmol) was slowly added dropwise. After the addition of 2,4,6-trimethylpyridine was complete, the reaction continued for 2 h at low temperature, and then the reaction solution was moved to a freezer of 0° C. and stirred for 2 days. After the reaction was complete, the reaction solution was moved to a 0.25 L separatory funnel, added with about 20 ml of saturated saline, and extracted by ethyl acetate four times. The organic phases were combined and concentrated by evaporation to remove the solvent. The residue was dissolved in appropriate amount of dichloromethane, loaded on a chromatographic column and purified. Eluate was collected and concentrated to afford 250.92 mg of Compound

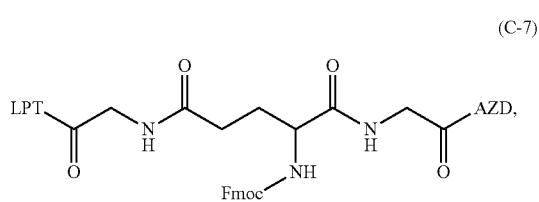
(C-7)

with a yield of 99%.

Compound C-7 (128 mg, 0.08235 mmol) was placed into 50 ml round bottom flask and dissolved in about 1.2 ml of DMF, and morpholine (0.144 ml, 1.6470 mmol) was added under stirring. The reaction solution was stirred at room temperature for 3 h. After the reaction was complete, the reaction solution was precipitated by ethyl ether to remove large quantity of impurities detected at ultraviolet wavelength. Ethyl ether phase was removed. Precipitate was dissolved in dichloromethane mixed solution, loaded on a chromatographic column, and eluted with 5% methanol/dichloromethane, and then eluted with 3% aqueous ammonia/8% methanol/dichloromethane. Eluate was collected, concentrated by evaporation to remove the solvent to afford 108 mg of Compound D-7, with a yield of 99%.

$^1$H-NMR (400 Hz, DMSO-$d_6$) δ 11.85-11.60 (m, 1H), 10.00-9.80 (m, 1H), 8.80-8.70 (m, 1H), 8.60-8.50 (m, 1H), 8.40-8.25 (m, 2H), 8.25-8.15 (m, 2H), 8.15-8.10 (m, 1H), 8.02-7.98 (m, 1H), 7.96-7.92 (m, 1H), 7.85-7.76 (m, 1H), 7.75-7.65 (m, 1H), 7.51-7.44 (m, 1H), 7.35-7.25 (m, 6H), 7.24-7.12 (m, 2H), 7.12-7.05 (m, 1H), 6.73-6.65 (m, 1H), 6.62-6.55 (m, 1H), 0.30-5.25 (m, 2H), 4.91-4.82 (m, 1H), 4.80-4.69 (m, 1H), 4.65-4.50 (m, 1H), 4.49-4.36 (m, 3H), 4.34-4.26 (m, 1H), 3.90-3.80 (m, 1H), 3.80-3.70 (m, 3H), 3.68-3.60 (m, 1H), 3.40-3.30 (m, 3H), 3.10-3.00 (m, 3H), 2.35-2.20 (m, 2H), 2.15-2.03 (m, 3H), 2.20-1.85 (m, 2H), 1.70-1.55 (m, 6H)

MALDI-TOF MS [1200-1300] [M+Na$^+$]: 1256.6

ITMS +c ESIQ 1MS [300.00-1300.00] [M+H$^+$]: 1234.76, [M+Na$^+$]: 1256.63

Example 8

Synthesis of Polyethylene Glycol-Coupled Synergistic Anticancer Drug or Derivative Thereof as Shown by Formula C-8:

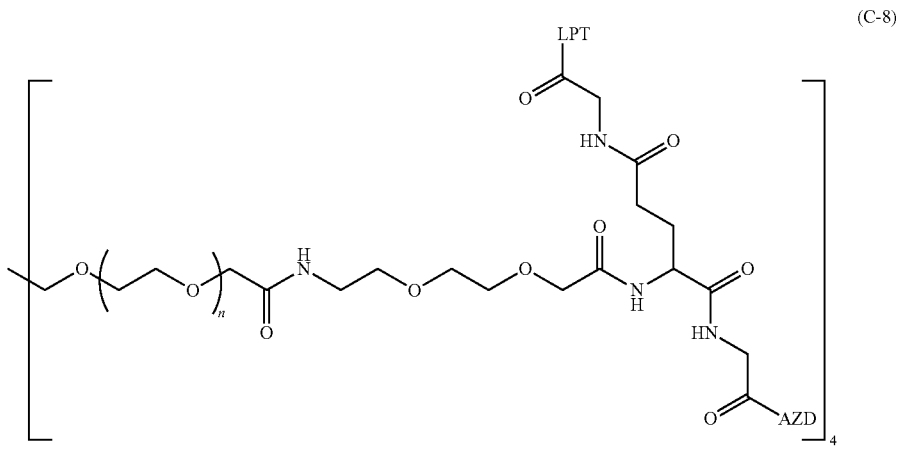
(C-8)

Figure 4:
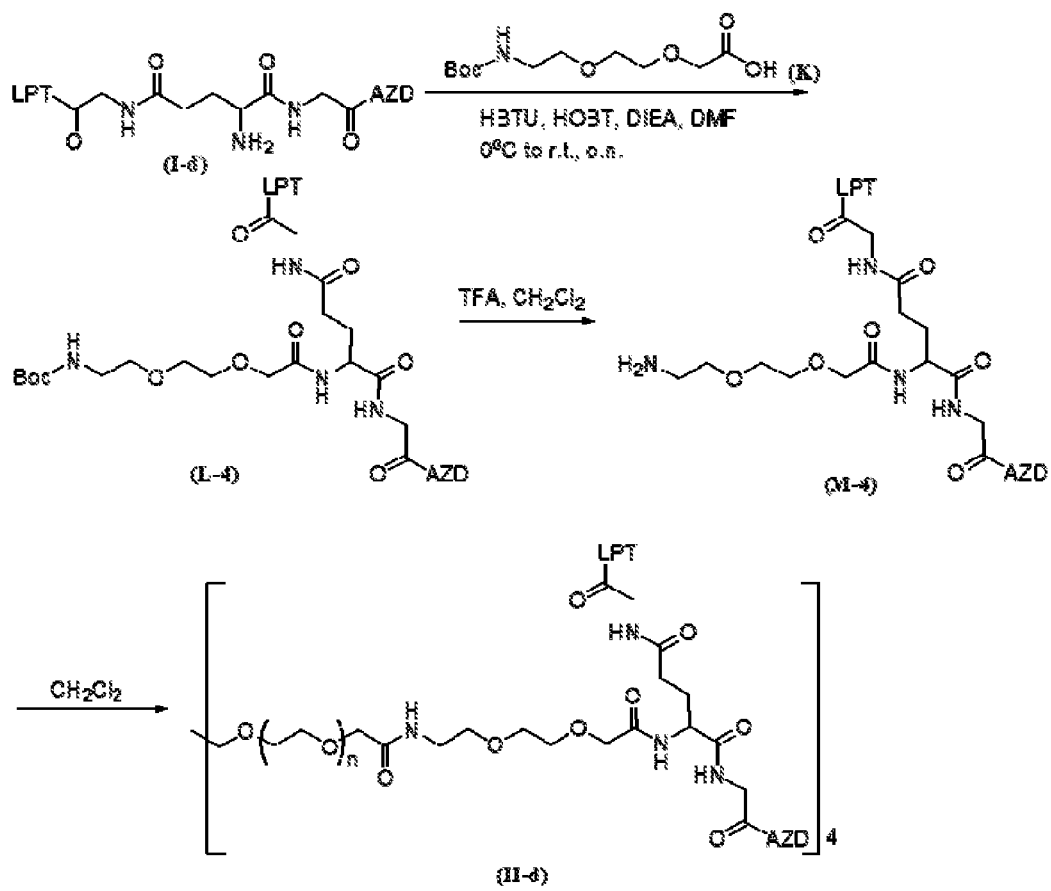
FIG. 4 is a scheme of synthesis route of the compound II-d provided in Example 8.

Synthesis route was shown in FIG. 4.

Compound D-7 (0.95 g, 0.7702 mmol), Compound B-2 (0.2026 g, 0.7702 mmol), HBTU (0.4336 g, 1.1554 mmol)

and HOBT (0.1561 g, 1.1554 mmol) were placed into a 500 ml round bottom flask, and then dissolved in DMF (80 ml). The solution was stirred at −5° C. At the same condition, DIEA (0.6 ml, 3.4661 mmol) was slowly added dropwise. After the addition of DIEA, the reaction continued for 1 h at low temperature, and then the reaction solution was moved to room temperature and stirred overnight. After the reaction was complete, the reaction solution was moved to a 1 L round bottom flask and was precipitated by n-hexane. N-hexane phase was removed, and precipitate was dissolved in methanol and dichloromethane. Appropriate amount of silica gel powder was added to make a solid solution, which was loaded on a chromatographic column and eluted with gradient eluent of 2% aqueous ammonia/4% methanol/dichloromethane to 3% aqueous ammonia/6% methanol/dichloromethane. Eluate was collected and concentrated to afford 660 mg of Compound A-8, with a yield of 58%.

Compound A-8 (650 mg, 0.4397 mmol) was placed into a 100 mL round bottom flask, and about 15 ml of dichloromethane was added to dissolve, and TFA (0.67 ml, 8.7934 mmol) was added under stirring. The reaction solution was stirred at room temperature for 3 h. After the reaction was complete, the reaction solution was concentrated to remove the solvent, and then the residue was dissolved in appropriate amount of methanol. Solid sodium bicarbonate powder was added under stirring to neutralize the remaining of TFA. After the neutralization was completed, the mixture was filtered, and appropriate amount of silica gel powder was added to the filtrate to make a solid solution, which was loaded on a chromatographic column, eluted with 2% methanol/dichloromethane, and then eluted with gradient eluent of 2% aqueous ammonia/5% methanol/dichloromethane to 3% aqueous ammonia/8% methanol/dichloromethane. Eluate was collected, concentrated by evaporation to remove the solvent, to afford 550 mg of Compound B-8, with a yield of 91%.

Compound B-8 (550 mg, 0.3986 mmol) was placed into a 100 mL round bottom flask and dissolved in dichloromethane (30 ml) and DMF (6 ml), and then 4ARM-SCM-40K (2.8972 g, 0.06643 mmol) was added. The reaction solution was stirred at room temperature for 2 weeks. After the reaction was complete, the reaction solution was precipitated by anhydrous ethyl ether and filtered. The filter cake was dissolved in dichloromethane, loaded on a chromatographic column, and eluted with the following eluents sequentially: dichloromethane, 5% methanol/dichloromethane, and 3% aqueous ammonia/8% methanol/dichloromethane. Eluate was collected, concentrated by evaporation to remove the solvent, to afford 2.0 g of Compound C-8 9-140. with a yield of 71%.

$^1$H-NMR (400 Hz, DMSO-d$_6$) δ 11.70-11.60 (m, 4H), 10.00-9.75 (m, 4H), 8.80-8.60 (m, 4H), 8.60-8.50 (m, 4H), 8.37-8.25 (m, 8H), 8.25-8.15 (m, 4H), 8.15-8.05 (m, 8H), 8.04-7.98 (m, 4H), 7.98-7.83 (m, 8H), 7.82-7.78 (m, 4H), 7.77-7.70 (m, 4H), 7.38-7.25 (m, 32H), 7.25-7.12 (m, 8H), 7.11-7.05 (m, 4H), 6.80-6.12 (m, 4H), 6.70-6.55 (m, 4H), 5.38-5.22 (m, 8H), 4.91-4.82 (m, 4H), 4.80-4.69 (m, 4H), 4.58-4.50 (m, 4H), 4.49-4.33 (m, 12H), 4.30-4.15 (m, 8H), 3.98-3.90 (m, 8H), 3.85-3.74 (m, 16H), 3.65-3.58 (m, 8H), 3.59-3.48 (m, 4192.68H), 3.40-3.35 (m, 24H), 3.10-3.00 (m, 20H), 2.30-2.18 (m, 8H), 2.15-2.04 (m, 8H), 2.04-1.92 (m, 12H), 1.90-1.75 (m, 24H)

MALDI-TOF MS [40000-50000] highest peak 46130.8.

Example 9

Synthesis of Drug Intermediate as Shown by Formula J-9:

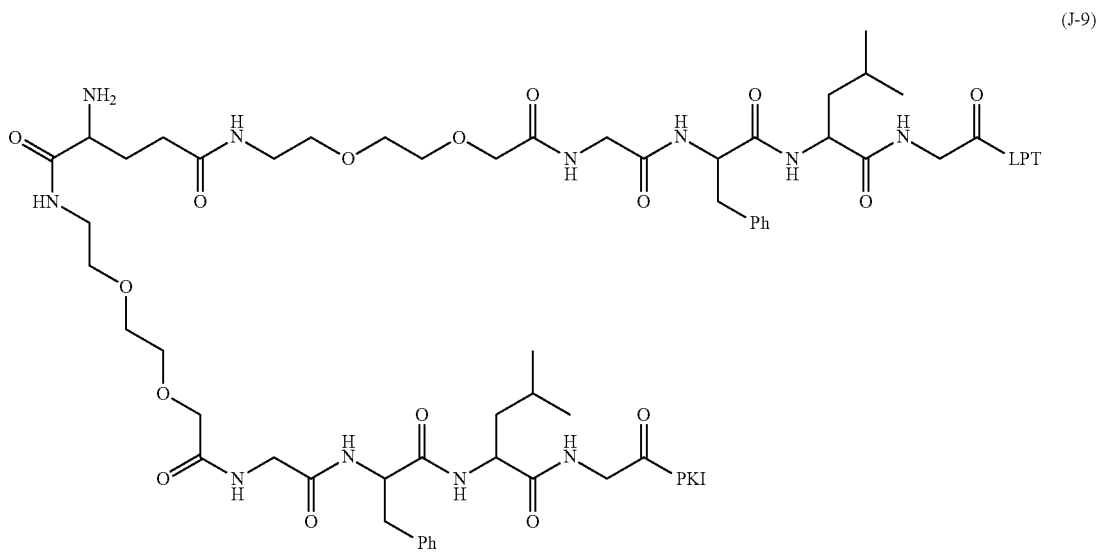

(J-9)

Example 9-1

Preparation of Compound

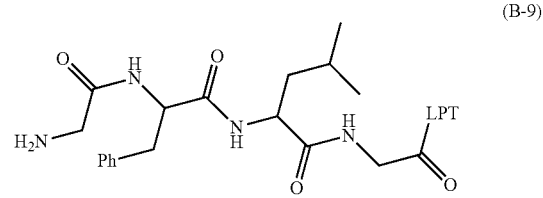

(B-9)

Raw material Boc-NH-GFLG-OBn (protected SEQ ID NO: 1) (3.0054 g, 5.148 mmol, Nanjing PharmaBlock Sciences, Inc.), and 10% palladium/carbon catalyst (75 mg)

were added to a hydrogenation reaction apparatus, and then DMF (30 ml) was added to dissolve the above raw material, with the level of solvent above stir bar. The hydrogenation reaction apparatus was closed. Water pump was used to pump out the air in reaction system for about 3 min, and then hydrogen was recharged. The operation of pumping-recharging was repeated three times, making the pressure readings on the hydrogenation reaction apparatus be 18 psi. Reaction solution was stirred overnight at room temperature. The end of the reaction was detected by TLC plate. After the reaction was complete, post-treatment was performed. Reaction solution was homogenously added dropwise to a suction filter filled with compacted diatomite, and then the reaction apparatus was washed by DMF (20 ml), until no product was left in the reaction apparatus, resulting in DMF solution of reaction product

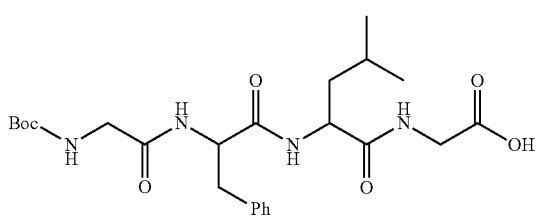 [SMILES: CC(C)CC(NC(=O)C(Cc1ccccc1)NC(=O)CNC(=O)OC(C)(C)C)C(=O)NCC(=O)O]

(Boo-NH-GFLG-OH) (protected SEQ ID NO: 1), which was directly used in next step.

The above product Boc-NH-GFLG-OH (protected SEQ ID NO: 1) (5.149 mmol), lapatinib (2.601 g, 4.477 mmol, Wuhan Yuancheng Gongchuang Technology Co., LTD), HBTU (2.547 g, 6.715 mmol) and HOBT (0.907 g, 6.715 mmol) were placed into a 250 mL round bottom flask and dissolved in DMF (90 ml). The solution was stirred for 30 min at −5° C., and then DIEA was slowly added dropwise (3.33 ml, 20.147 mmol). After the addition of DIEA was complete, the reaction continued for 2 h at low temperature, and then the reaction apparatus was placed at room temperature and the reaction solution was stirred overnight. After the reaction was complete, post-treatment was performed to afford 3.7347 g of compound

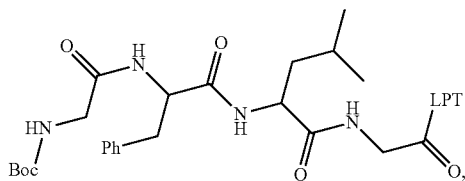

(A-9)

with a yield of 79.025%.

A-9 (7.3782 g, 6.989 mmol) was added to a 250 mL round bottom flask, and dissolved in dichloromethane (75 ml), and then TFA (5.192 ml, 69.89 mmol) was added, and the solution was stirred overnight at room temperature. After the reaction was complete, the reaction solution was concentrated under reduced pressure to remove the solvent. The residue was dissolved in appropriate amount of ethyl acetate, transferred to 500 mL separatory funnel, and added with saturated sodium bicarbonate (100 ml) to neutralize the remaining of TFA. After the neutralization, organic phase was isolated, and the product in aqueous phase was extracted by ethyl acetate for 3 times (150 ml*3). The organic phases were combined, dried over anhydrous sodium sulfate, suction filtered, and then the filtrate was concentrated. The concentrate was mixed with silica gel powder, loaded on a chromatographic column and eluted with 4% methanol/1% aqueous ammonia/dichloromethane. Eluate was collected and concentrated by evaporation to remove the solvent, to afford 4.7308 g of Compound B-9, with a yield of 70.85%.

$^1$H NMR (400 MHz, DMSO-d$_6$) δ 9.86 (s, 1H), 8.75-8.74 (m, 1H), 8.56 (s, 1H), 8.22-8.01 (m, 5H), 7.82-7.73 (m, 2H), 7.53-7.49 (m, 1H), 7.33-7.11 (m, 11H), 6.70-6.55 (m, 2H), 5.27 (s, 2H), 4.76-4.60 (m, 3H), 4.38-4.26 (m, 3H), 3.77-3.62 (m, 3H), 3.39-3.37 (m, 1H), 3.07-3.02 (m, 6H), 2.86-2.82 (m, 1H), 1.82 (s, 2H), 1.61-1.49 (m, 3H), 0.88-0.80 (m, 6H).

Example 9-2

Preparation of Compound

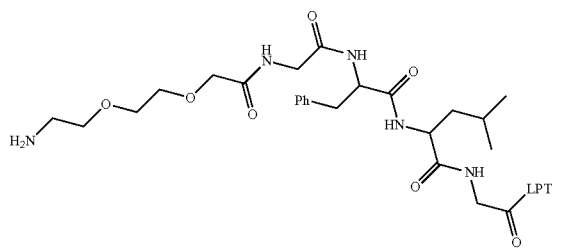

(C-9)

Compound B-9, i.e. GFLG-LPT (modified SEQ ID NO: 1) (4.6 g, 4.81 mmol), Boc-NHCH$_2$CH$_2$O—CH$_2$CH$_2$OCH$_2$COOH (1.52 g, 5.772 mmol, purchased from Changsha Kangpeng Pharmaceutical Co., Ltd.), HBTU (2.74 g, 7.22 mmol) and HOBT (0.976 g, 7.22 mmol) were placed into a 500 ml round bottom flask and then dissolved in DMF (138 ml). The solution was stirred for 30 min at −5° C., and then DIEA (3.58 ml, 21.65 mmol) was slowly added dropwise. After the addition of DIEA was complete, the reaction continued for 2 h at low temperature, and then the reaction apparatus was placed at room temperature and the solution was stirred overnight. After the reaction was complete, post-treatment was performed to afford 3.19 g of compound

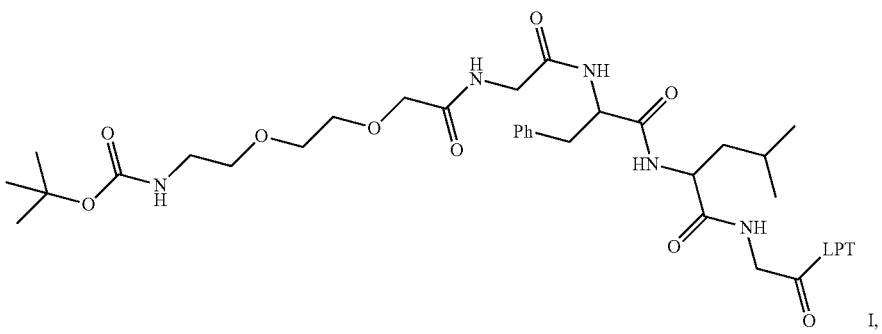

I, with a yield of 55.38%.

The above compound (3.13 g, 2.61 mmol) was added to a 100 mL round bottom flask, and dissolved in dichloromethane (45 ml), and then TFA (1.94 ml, 26.1 mmol) was added at room temperature, and the reaction was stirred at room temperature for 4 days. After the reaction was complete, the reaction solution was concentrated under reduced pressure to remove the solvent. The residue was dissolved in appropriate amount of ethyl acetate, transferred to a 500 mL separatory funnel, and added with saturated sodium bicarbonate (100 ml) to neutralize the remaining of TFA. After the neutralization, organic phase was isolated, and the product in aqueous phase was extracted by ethyl acetate for 3 times (150 ml*3). The organic phases were combined, dried over anhydrous sodium sulfate and suction filtered, and then the filtrate was concentrated. The concentrate was mixed with silica gel powder, loaded on a chromatographic column and eluted with 4% methanol/2% aqueous ammonia/dichloromethane. Eluate was collected and concentrated by evaporation to remove the solvent, to afford 2.072 g of Compound C-9, with a yield of 72.1%.

$^1$H NMR (400 MHz, DMSO-d$_6$) δ 8.75-8.74 (m, 1H), 8.56 (s, 1H), 8.14-8.12 (m, 3H), 8.02-8.01 (m, 2H), 7.82-7.73 (m, 3H), 7.50-7.47 (m, 1H), 7.35-7.11 (m, 11H), 6.70-6.55 (m, 2H), 5.27 (s, 2H), 4.76-4.70 (m, 2H), 4.59-4.53 (m, 1H), 4.38-4.13 (m, 3H), 3.89-3.75 (m, 5H), 3.58-3.52 (m, 7H), 3.37-3.34 (m, 1H), 3.07-3.03 (m, 5H), 2.80-2.77 (m, 1H), 2.64-2.61 (m, 2H), 1.98-1.47 (m, 5H), 0.88-0.80 (m, 6H); MALDI-TOF MS: [M+H$^+$] 1100.30, [M−H$^+$] 1098.25, [M+Na$^+$] 1122.25.

Example 9-3

Preparation of Compound

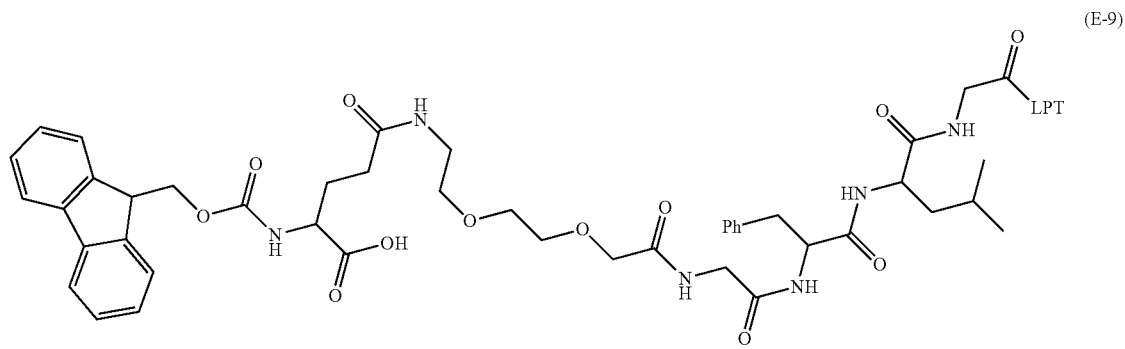

(E-9)

Fmoc-Glu-OH (OtBu) (0.54 g, 1.27 mmol) was placed into a 100 mL round bottom flask, and dissolved in DMF (21 mL), and then Compound C-9, i.e. LC-GFLG-LPT (modified SEQ ID NO: 1) (1.0 g, 0.908 mmol), and PyAOP (0.66 g, 1.27 mmol) were added. The solution was stirred for 30 min at 0° C., and then 2,4,6-trimethylpyridine (0.12 ml, 0.908 mmol) was slowly added dropwise. After the addition of 2,4,6-trimethylpyridine was complete, reaction continued at this low temperature for 3 days. After the reaction was complete, post-treatment was performed to afford 0.388 g of pure product Kangpeng Pharmaceutical Co., Ltd.), HBTU (5.094 g, 13.431 mmol) and HOBT (1.8149 g, 13.431 mmol) were placed into a 250 mL round bottom flask and then dissolved in DMF (95 ml). The solution was stirred for 30 min at −5° C., and then DIEA was slowly added dropwise (6.659 ml, 40.293 mmol). After the addition of DIEA was complete, the reaction continued for 2 h at low temperature, and then the reaction apparatus was placed at room temperature and the

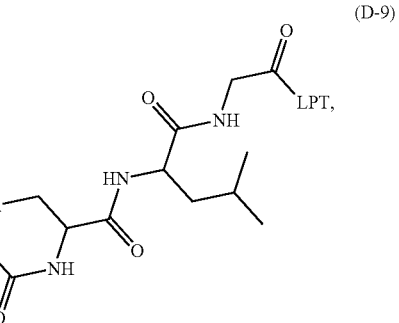

(D-9)

and 1.419 g of combined product was obtained, with a yield of 94.2%.

MALDI-TOF MS: [M+H$^+$] 1507.45, [M−H$^+$] 1505.40, [M+Na$^+$] 1529.45.

Compound D-9 (1.35 g, 0.895 mmol) was placed into a 100 mL round bottom flask and dissolved in dichloromethane (15 ml), and then TFA (4.5 ml) was added. The reaction solution was stirred overnight at room temperature. After the reaction was complete, the reaction solution was concentrated under reduced pressure to remove the solvent. The residue was dissolved in dichloromethane (5 ml), added with n-hexane (50 ml) and shaken, making the product precipitate, and then placed in a freezer to stand for 30 min, after which the supernatant was poured, and the residue was dissolved in dichloromethane (5 ml); n-hexane (50 ml) was added and shaken, making the product precipitated, and then placed in a freezer to stand for 30 min; this operation was repeated twice. The precipitated product was concentrated under reduced pressure to remove the solvent. The product was collected to afford 1.585 g of E-9.

MALDI-TOF MS: [M−H$^+$] 1449.40.

Example 9-4

Preparation of Compound

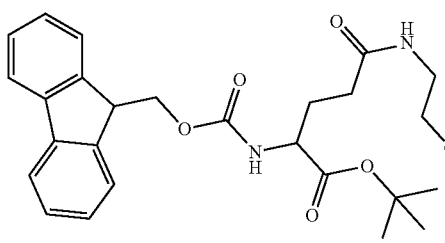

(G-9)

Boc-NH-GFLG-OH (protected SEQ ID NO: 1) (10.297 mmol), allosteric PKI-587 (5.136 g, 8.954 mmol, Changsha reaction continued under stirring overnight. After the reaction was complete, the reaction solution was transferred to a 1 L separatory funnel, added with saturated sodium bicarbonate solution (200 ml), and extracted by ethyl acetate three times (200 ml*3). The organic phases were combined, and washed by saturated sodium bicarbonate (100 ml) one time, and then the water therein was removed by saturated sodium chloride (100 ml). Organic phase was collected and placed in a 2 L round bottom flask, placed in a freezer overnight for crystallization, and suction filtered to afford 9.1019 g of compound

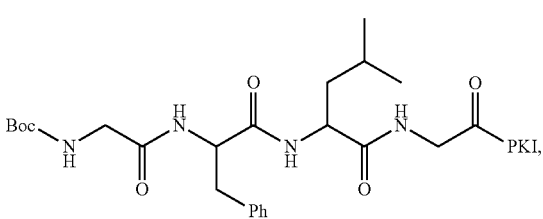

(F-9)

with a yield of 96.98%.

$^1$H NMR (400 MHz, DMSO-d$_6$) δ 9.43 (d, J=16.0 Hz, 2H), 8.29-8.27 (m, 3H), 7.95-7.88 (m, 2H), 7.58-7.54 (m, 4H), 7.40-7.38 (m, 2H), 7.24-7.22 (m, 5H), 6.93 (t, J=8.0 Hz, 1H), 4.55-4.35 (m, 2H), 3.98-3.51 (m, 28H), 3.04-3.00 (m, 1H), 2.89-2.69 (m, 1H), 1.64-1.50 (m, 3H), 1.36 (s, 9H), 0.90-0.83 (m, 6H). MALDI-TOF MS: [M+H$^+$] 1048.50, [M−H$^+$] 1046.40, [M+Na$^+$] 1070.45.

Compound F-9 (3.007 g, 2.862 mmol) was added to a 250 mL round bottom flask and dissolved in dichloromethane (35 ml), and then TFA (2.125 ml, 28.62 mmol) was added. The solution was stirred overnight at room temperature. After the reaction was complete, the reaction solution was concentrated under reduced pressure to remove the solvent. The residue was dissolved in appropriate amount of ethyl acetate, transferred to a 500 mL separatory funnel, and added with saturated sodium bicarbonate (100 ml) to neutralize the remaining of TFA. After the neutralization, organic phase was separated, and the product in aqueous phase was extracted by ethyl acetate for 3 times (150 ml*3). The organic phases were combined, and solid was precipitated, followed by suction filtration. The precipitated solid is proved by TLC to be the desired product. The product was collected to afford 2.2522 g of compound G-9, with a yield of 83.001%. $^1$H NMR (400 MHz, DMSO-$d_6$) S=9.20 (d, J=12.0 Hz, 2H), 8.30-8.27 (m, 4H), 7.96-7.94 (t, J=8.0 Hz, 1H), 7.58-7.54 (m, 4H), 7.40-7.38 (m, 2H), 7.26-7.24 (m, 5H), 5.23 (s, 2H), 4.63 (s, 1H), 4.38-4.37 (m, 1H), 3.99-3.50 (m, 28H), 3.07-3.03 (m, 1H), 2.80-2.77 (m, 1H), 1.62-1.49 (m, 3H), 0.91-0.84 (m, 6H). MALDI-TOF MS: [M+H$^+$] 948.40.

Example 9-5

Preparation of Compound (H-9)

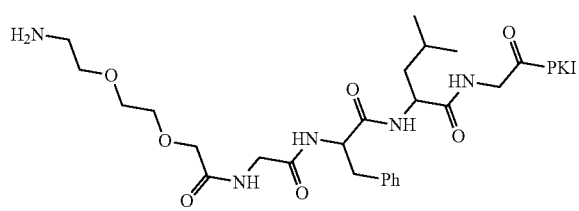

Compound G-9, i.e. GFLG-PKI (modified SEQ ID NO: 1) (2.18 g, 2.299 mmol), Boc-NHCH$_2$CH$_2$O—CH$_2$CH$_2$OCH$_2$COOH (0.73 g, 2.759 mmol), HBTU (1.31 g, 3.449 mmol) and HOBT (0.47 g, 3.449 mmol) were placed into a 250 mL round bottom flask and then dissolved in DMF (66 ml). The solution was stirred for 30 min at −5° C., and then DIEA (1.71 ml, 10.346 mmol) was slowly added dropwise. After the addition of DIEA was complete, the reaction continued for 2 h at low temperature, and then the reaction apparatus was placed at room temperature and the reaction continued under stirring overnight. After the reaction was complete, post-treatment was performed to afford 1.2286 g of product, with a yield of 34.4%. $^1$H NMR (400 MHz, DMSO-$d_6$) δ=9.08 (s, 1H), 8.98 (s, 1H), 8.30-8.11 (m, 4H), 7.89-7.77 (m, 2H), 7.58-7.53 (m, 4H), 7.40-7.38 (m, 2H), 7.23-7.17 (m, 5H), 6.79-6.77 (t, J=8.0 Hz, 1H), 4.56-4.55 (t, J=4.0 Hz, 1H), 4.36-4.34 (m, 1H), 3.89-3.51 (m, 34H), 3.36-3.33 (m, 2H), 3.06-3.05 (m, 3H), 2.78-2.76 (m, 1H), 1.62-1.50 (m, 3H), 1.36 (s, 9H), 0.90-0.83 (m, 6H).

The above product (2.02 g, 1.69 mmol) was added to a 100 mL round bottom flask and dissolved in dichloromethane (21 ml), and then TFA (1.25 ml, 16.9 mmol) was added. The reaction continued under stirring at room temperature for 4 days. After the reaction was complete, the reaction solution was concentrated under reduced pressure to remove the solvent. The residue was dissolved in appropriate amount of ethyl acetate, transferred to a 500 mL separatory funnel, and added with saturated sodium bicarbonate (100 ml) to neutralize the remaining of TFA. After the neutralization, organic phase was isolated, and the product in aqueous phase was extracted by ethyl acetate for 3 times (150 ml*3). The organic phases were combined, dried over anhydrous sodium sulfate and suction filtered, and then the filtrate was concentrated. The concentrate was mixed with silica gel powder, loaded on a chromatographic column, and eluted with 6% methanol/2% aqueous ammonia/dichloromethane. Eluate was collected and concentrated by evaporation to afford 1.057 g of Compound H-9, with a yield of 56.4%.

$^1$H NMR (400 MHz, DMSO-$d_6$) δ 9.08 (s, 1H), 9.05 (s, 1H), 8.30-8.12 (m, 4H), 7.90-7.82 (m, 2H), 7.58-7.53 (m, 4H), 7.40-7.38 (m, 2H), 7.25-7.20 (m, 5H), 4.56-4.55 (t, J=4.0 Hz, 1H), 4.36-4.34 (m, 1H), 3.89-3.51 (m, 34H), 3.05-3.02 (m, 1H), 2.79-2.62 (m, 3H), 1.63-1.48 (m, 5H), 0.90-0.83 (m, 6H). MALDI-TOF MS: [M+H$^+$] 1093.45, [M−H$^+$] 1091.40, [M+Na$^+$] 1115.40.

Example 9-6

Preparation of Compound J-9:

Compound E-9 (1.30 g, 0.895 mmol) was placed into a 100 mL round bottom flask and dissolved in DMF (20 ml), and then Compound H-9, i.e. LC-GFLG-PKI (modified SEQ ID NO: 1) (0.979 g, 0.895 mmol) and PyAOP (0.56 g, 1.2 mmol) were added. The solution was stirred for 30 min at 0° C., and then 2,4,6-trimethylpyridine (0.45 ml, 3.41 mmol) was slowly added dropwise. After the addition of 2,4,6-trimethylpyridine was complete, reaction continued for 2 days at this low temperature. After the reaction was complete, the reaction solution was transferred to a 1000 mL separatory funnel, and washed by deionized water (200 ml). The reaction bottle was washed by ethyl acetate. The mixed phases in the separatory funnel were shaken strongly. The organic phase was isolated, and extracted by ethyl acetate for three times (200 ml*3). The organic phases were combined, and washed by saturated sodium chloride (100 ml) for three times. The reaction product attached to the bottle wall was dissolved in methanol and dichloromethane. The products were combined and suction filtered. The filtrate was concentrated, mixed with silica gel powder, loaded on a chromatographic column and eluted with 10% methanol/dichloromethane. Eluate was collected and concentrated to afford 1.123 g of compound

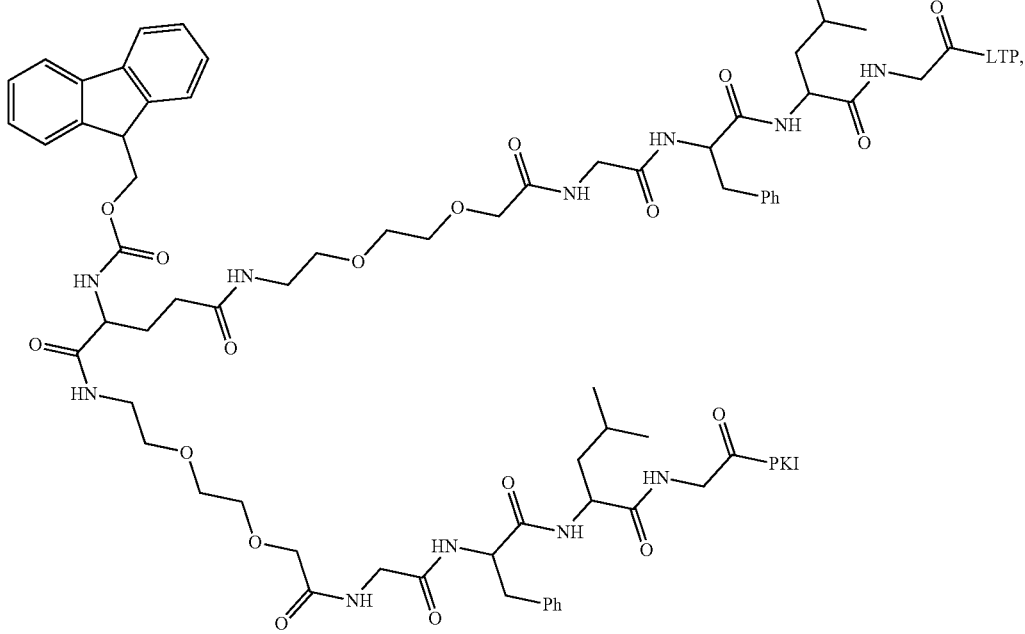

(I-9)

with a yield of 72.9%.

Compound I-9 (1.07 g, 0.423 mmol) was added to a 100 mL round bottom flask and dissolved in DMF (13 ml), and then morpholine (1.11 ml, 12.7 mmol) was added. The reaction solution was stirred at room temperature for 2.5 h. After the reaction was complete, the reaction solution was transferred to a 1000 mL separatory funnel, and saturated sodium chloride (100 ml) was added. Reaction bottle was washed by ethyl acetate. The mixed phases in the separatory funnel were shaken strongly. The organic phase was isolated and extracted by ethyl acetate three times (200 ml*3). The organic phases were combined, and washed by saturated sodium chloride (100 ml) three times. The reaction product attached to the bottle wall was dissolved in methanol and dichloromethane. The products in the organic phase were combined and suction filtered. The filtrate was concentrated, mixed with silica gel powder, loaded on a chromatographic column, and eluted with 8% methanol/2% aqueous ammonia/dichloromethane. Eluate was collected and concentrated to afford 0.5664 g of J-9, with a yield of 74.9%.

Example 10

Synthesis of Polyethylene Glycol-Coupled Anticancer Drug or Derivative Thereof as Shown by Formula C-9:

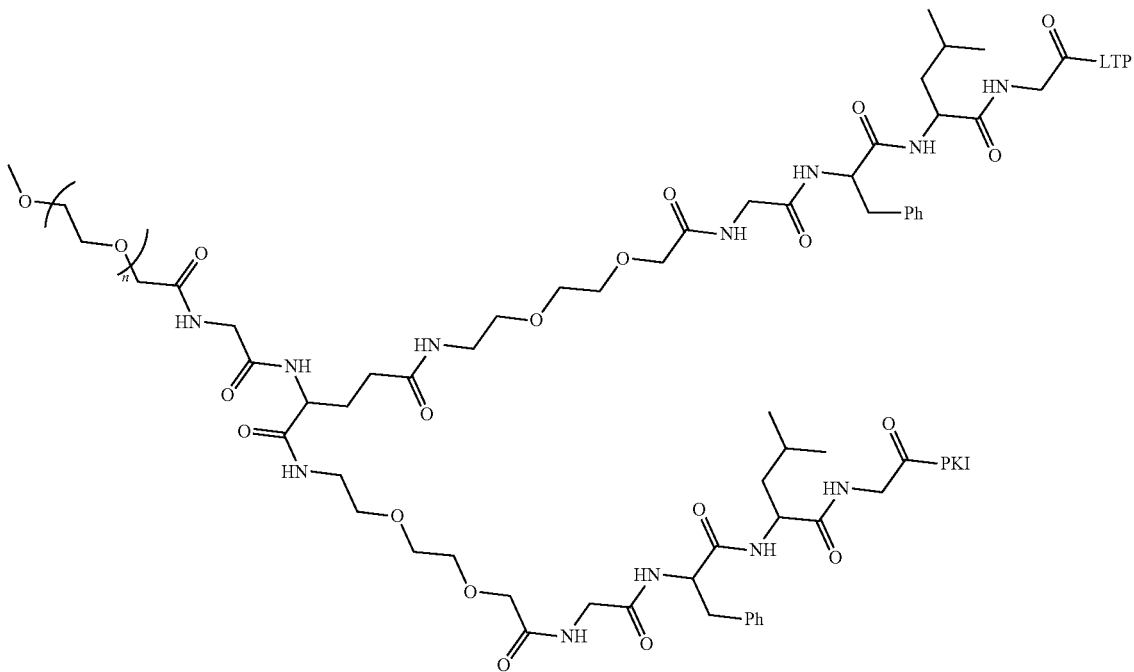

(II-e)

Compound J-9 (0.55 g, 0.239 mmol), Boc-Gly (0.05 g, 0.286 mmol), HBTU (0.14 g, 0.359 mmol) and HOBT (0.048 g, 0.359 mmol) were placed into a 100 mL round bottom flask and then dissolved in DMF (12 ml). The solution was stirred for 30 min at −5° C., and then DIEA (0.18 ml, 1.08 mmol) was slowly added dropwise. After the addition of DIEA was complete, the reaction continued for 2 h at low temperature, and then the reaction apparatus was placed at room temperature and the reaction solution was stirred overnight. After the reaction was complete, the reaction solution was transferred to a 1 L separatory funnel, and the reaction bottle was washed with ethyl acetate. Deionized water (200 ml) was added and shaken. Organic phase was isolated, extracted by ethyl acetate for three times (200 ml*3), combined, and then water therein was removed with saturated sodium chloride solution (100 ml), followed by suction filtration. The filtrate was concentrated, mixed with silica gel powder, loaded on a chromatographic column, and eluted with 6% methanol/2% aqueous ammonia/dichloromethane. Eluate was collected and concentrated to afford 0.5723 g of compound

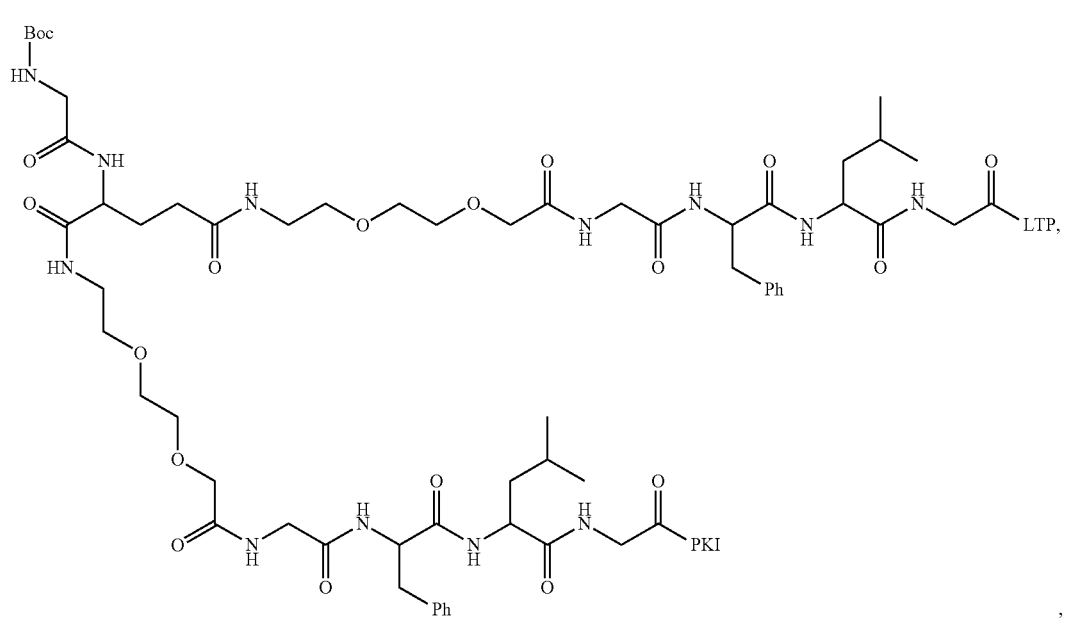

(A-9)

with a yield of 97.3%.

Compound A-9 (0.55 g, 0.223 mmol) was added to a 100 mL round bottom flask and dissolved in dichloromethane (11 mL), and then TFA (1.85 ml, 24.91 mmol) was added. The reaction solution was stirred at room temperature for 1 day. After the reaction was complete, the reaction solution was concentrated under reduced pressure to remove the solvent. The residue was dissolved in appropriate amount of ethyl acetate, transferred to a 500 mL separatory funnel, and added with saturated sodium bicarbonate (100 mL) to neutralize the remaining of TFA. After the neutralization was complete, the organic phase was isolated, and the product in the aqueous phase was extracted by ethyl acetate for 5 times (100 mL×5). The organic phases were combined, dried over anhydrous sodium sulfate and suction filtered. The filtrate was concentrated, mixed with silica gel powder, loaded on a chromatographic column, and eluted with 6% methanol/ 2% aqueous ammonia/dichloromethane. Eluate was collected and concentrated by evaporation to remove the solvent, to afford 0.474 g of Compound

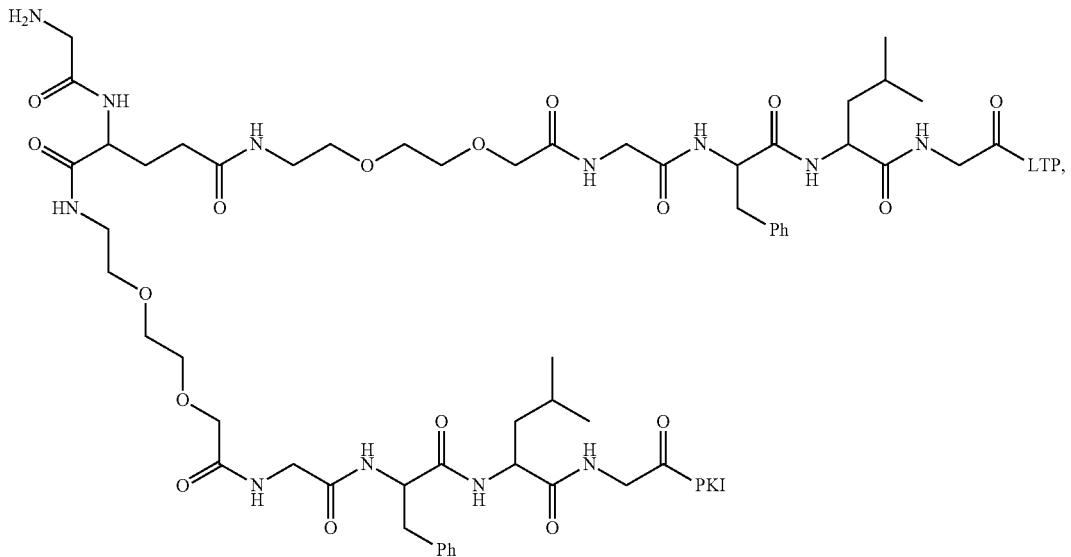

(B-9)

with a yield of 90.0%. ¹H NMR (400 MHz, DMSO-d₆) δ=9.89-9.87 (m, 1H), 9.13 (s, 1H), 9.04 (s, 1H), 8.75-8.74 (m, 1H), 8.56 (s, 1H), 8.50 (d, J=8.0 Hz, 1H), 8.29 (d, J=12.0 Hz, 2H), 8.22-8.12 (m, 5H), 8.01-8.00 (m, 2H), 7.91-7.87 (m, 2H), 7.82-7.71 (m, 4H), 7.55 (t, J=20.0 Hz, 4H), 7.48 (dd, J=16.0, 12.0 Hz, 2H), 7.40-7.28 (m, 6H), 7.23-7.06 (m, 12H), 6.20 (d, J=4.0 Hz, 1H), 5.27 (s, 2H), 4.75-4.70 (m, 2H), 4.58-4.54 (m, 2H), 4.36-4.11 (m, 7H), 3.98-3.74 (m, 21H), 3.66-3.41 (m, 29H), 3.22-3.16 (m, 5H), 3.07-3.02 (m, 5H), 2.76-2.67 (m, 3H), 2.08 (t, J=8.0 Hz, 2H), 1.84-1.74 (m, 2H), 1.62-1.61 (m, 2H), 1.52-1.49 (m, 3H), 1.25-1.03 (m, 1H), 0.90-0.79 (m, 12H).

Compound B-9 (0.400 g, 0.169 mmol) was placed into a 100 mL round bottom flask, and then dissolved in dichloromethane (about 20 mL) and DMF (6 mL), and finally M-SCM-10K (1.495 g, 0.141 mmol) was added. The reaction mixture was stirred at room temperature in dark for 3 days. After the reaction was complete, the reaction mixture was concentrated, precipitated with anhydrous ethyl ether, and filtered. The filter cake was dissolved in dichloromethane, loaded on a chromatographic column and eluted sequentially with dichloromethane, 5% methanol/dichloromethane, and 3% aqueous ammonia/8% methanol/dichloromethane, to afford 1.70 g of Compound C-9. ¹H NMR (400 MHz, DMSO-d₆) δ=9.88-9.86 (m, 1H), 9.10 (s, 1H), 9.00 (s, 1H), 8.75-8.73 (m, 1H), 8.56 (s, 1H), 8.29 (d, J=8.0 Hz, 2H), 8.24-7.95 (m, 10H), 7.87-7.71 (m, 6H), 7.55 (t, J=16.0 Hz, 4H), 7.48 (dd, J=16.0, 8.0 Hz, 2H), 7.40-7.06 (m, 16H), 5.26 (s, 2H), 4.75-4.70 (m, 2H), 4.58-4.53 (m, 2H), 4.35-4.34 (m, 3H), 4.23-4.20 (m, 4H), 3.98-3.41 (m, 992H), 3.24-3.16 (m, 6H), 3.06-3.02 (m, 5H), 2.89-2.67 (m, 5H), 2.07-1.93 (m, 2H), 1.62-1.49 (m, 5H), 1.24-1.07 (m, 1H), 0.89-0.79 (m, 12H). MALDI-TOF MS range: 12100-13500.

Example 11

Synthesis of the Anticancer Drug of Compound as Shown by Formula M-10:

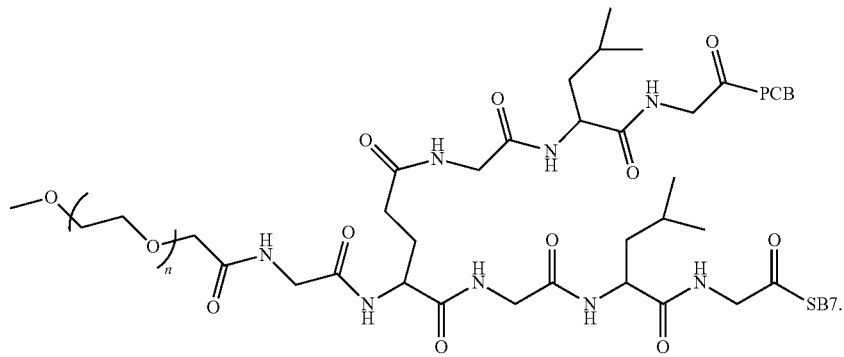

(M-10)

Step S1, Treating the Compound of Formula A-10 for Use

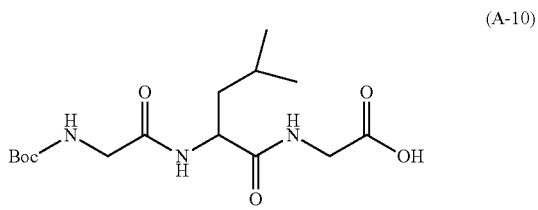 [SMILES: CC(C)CC(NC(=O)CNC(=O)OC(C)(C)C)C(=O)NCC(=O)O]
(A-10)

Boc-NH-GLG-OBn (6.0045 g, 13.7873 mmol, Nanjing PharmaBlock) was added to a hydrogenation reaction tank, 10% Pd/C (0.1005 g) was added, and DMF (30 mL) was added to dissolve. Hydrogen gas was introduced with 14 psi of hydrogen pressure, and the reaction mixture was stirred overnight at room temperature. After the reaction was complete, the reaction solution was filtered through a compacted diatomite layer, and filter cake was washed with DMF (20 mL×3). Filtrate was moved to a 250 mL round bottom flask.

Step S2, Preparing the Compound of Formula B-10

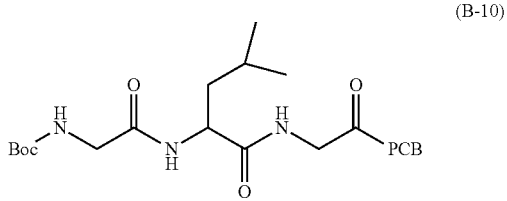
(B-10)

Palbociclib (7.1547 g, 15.9870 mmol, briefly referred to as "PCB", Beijing Isomersyn), HBTU (9.0944 g, 23.9805 mmol) and HOBT (3.2405 g, 23.9805 mmol) were added to a 250 mL flask which held a DMF solution containing compound of formula A-10 (6.3500 g, 18.3851 mmol). The mixture was stirred at −5° C. for about 20 min, and then DIEA (11.8906 mL, 71.9415 mmol) was slowly added dropwise. After the addition of DIEA was complete, the reaction mixture was stirred at −5° C. for 1 hour, and then was stirred overnight at room temperature. After the reaction was complete, the reaction solution was transferred to a 2 L beaker, added with 800 ml of saturated sodium bicarbonate solution, and solid was precipitated, and suction filtered. Filter cake was treated with toluene (100 mL×5) to remove water, dried, resulting in 12.1 g of compound of formula B-10, with a yield of 93.91%. $^1$H-NMR (400 MHz, DMSO-$d_6$) δ 10.17 (s, 1H), 8.96 (s, 1H), 8.10 (dd, J=12.0, 4.2 Hz, 2H), 7.88 (t, J=7.8 Hz, 2H), 7.52 (dd, J=9.1, 3.0 Hz, 1H), 6.97 (s, 1H), 5.94-5.61 (m, 1H), 4.39 (s, 1H), 4.00 (d, J=5.4 Hz, 2H), 3.58 (dd, J=16.1, 5.4 Hz, 4H), 3.16 (d, J=19.0 Hz, 4H), 2.43 (s, 3H), 2.31 (s, 3H), 2.25 (s, 2H), 1.89 (s, 2H), 1.82-1.70 (m, 2H), 1.66-1.56 (m, 3H), 1.52-1.43 (m, 2H), 1.38 (s, 9H), 1.24 (d, J=6.4 Hz, 2H), 0.86 (dd, J=15.4, 6.5 Hz, 6H);

MALDI-TOF MS: [M+H$^+$] 775.25, [M+] 774.45

Step S3, Preparing the Compound of Formula C-10

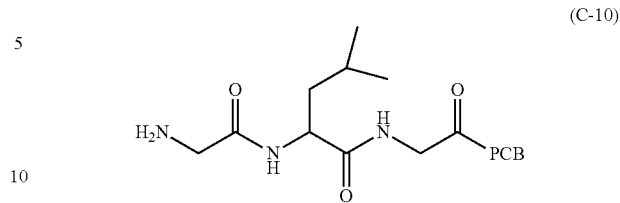
(C-10)

Compound of formula B-10 (7.0271 g, 9.0681 mmol) was added to a 250 mL flask and dissolved in dichloromethane (20 mL), and then TFA (5.3873 mL, 72.5492 mmol) was added. The reaction solution was stirred overnight at room temperature. After the reaction was complete, the reaction solution was evaporated to remove the solvent. The residue was dissolved in appropriate amount of methanol, added with a small amount of sodium bicarbonate solid powder to neutralize TFA, and suction filtered. The filtrate was evaporated to remove the solvent. The residue was mixed with silica gel powder, loaded on a chromatographic column, and eluted with eluent of 5% methanol:1% aqueous ammonia:94% dichloromethane. Eluate was collected and concentrated, to afford 5.2531 g of compound of formula C-10, with a yield of 85.60%. $^1$H-NMR (400 MHz, DMSO-$d_6$) δ 10.17 (s, 1H), 8.96 (s, 1H), 8.16 (t, J=5.5 Hz, 1H), 8.08 (d, J=2.9 Hz, 1H), 7.98 (d, J=8.9 Hz, 1H), 7.89 (d, J=9.0 Hz, 1H), 7.52 (dd, J=9.1, 3.0 Hz, 1H), 5.83 (p, J=8.6 Hz, 1H), 4.43 (d, J=5.9 Hz, 1H), 4.00 (d, J=5.5 Hz, 2H), 3.60 (s, 4H), 3.23-3.07 (m, 6H), 2.42 (s, 3H), 2.31 (s, 3H), 2.24 (s, 2H), 2.05 (s, 1H), 1.89 (s, 2H), 1.81-1.71 (m, 2H), 1.60 (dd, J=12.3, 6.2 Hz, 3H), 1.47 (ddd, J=19.4, 13.3, 6.1 Hz, 2H), 1.23 (s, 1H), 0.88 (dd, J=11.5, 6.5 Hz, 6H); MALDI-TOF MS: [M+H$^+$]675.30

Step S4, Preparing the Compound of Formula D-10

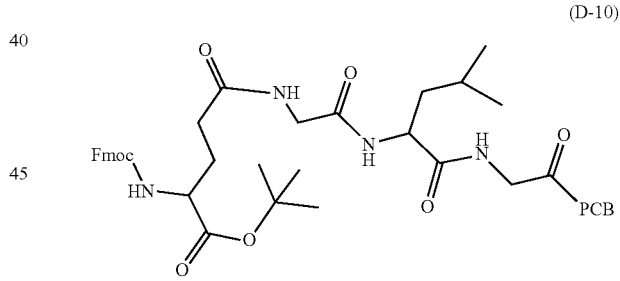
(D-10)

Fmoc-Glu-OtBu (2.6402 g, 6.2055 mmol) was added to a 250 mL flask, dissolved in about 70 mL of DMF, and placed into a constant temperature reaction bath of 0° C. Compound of formula C-10 (3.0176 g, 4.4325 mmol) and PyAoP (3.2354 g, 6.2055 mmol) were added under stirring, and after about 30 min, TMP (0.589 mL, 4.4325 mmol) was slowly added dropwise. The reaction solution was stirred overnight at 0° C. After the reaction was complete, the reaction solution was transferred to 2 L separatory funnel, and deionized water (300 mL) and ethyl acetate (300 mL) were added for extraction. The organic phase was isolated, and the aqueous phase was washed by ethyl acetate (200 mL×4). The organic phases were combined, dried over anhydrous sodium sulfate, and filtered, and the filtrate was concentrated by evaporation to remove the solvent. The residue was mixed with silica gel powder, loaded on a chromatographic column, and eluted with eluent of 5% methanol:95% dichloromethane. Eluate was collected and concentrated by evaporation to remove the solvent, resulting in 4.8342 g of compound of formula D-10, with a yield of 100%. $^1$H-NMR (400 MHz, DMSO-d$_6$) δ 10.17 (s, 1H), 8.96 (s, 1H), 8.14-7.99 (m, 4H), 7.89 (d, J=7.7 Hz, 3H), 7.73 (d, J=7.5 Hz, 3H), 7.51 (dd, J=9.1, 2.8 Hz, 1H), 7.42 (t, J=7.4 Hz, 2H), 7.33 (t, J=7.4 Hz, 2H), 5.84 (dd, J=17.8, 8.9 Hz, 1H), 4.49-4.19 (m, 4H), 4.05-3.83 (m, 3H), 3.79-3.54 (m, 6H), 3.16 (d, J=19.6 Hz, 5H), 2.42 (s, 3H), 2.31 (s, 3H), 2.27-2.20 (m, 3H), 1.93 (dd, J=20.8, 7.7 Hz, 4H), 1.77 (s, 2H), 1.66-1.47 (m, 5H), 1.39 (s, 9H), 0.86 (dd, J=16.0, 6.5 Hz, 6H); MALDI-TOF MS: [M−H$^+$] 1080.60

Step S5, Preparing the Compound of Formula E-10

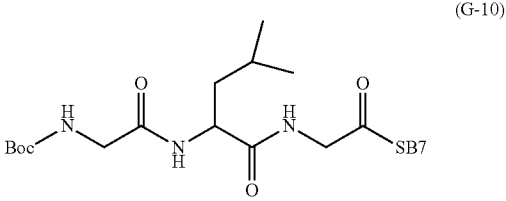

(E-10)

Compound of formula D-10 (4.8342 g, 4.4584 mmol) was added to a 100 mL flask, and dissolved in about 35 ml of dichloromethane. TFA (4.1779 mL, 56.259 mmol) was added under stirring, and the reaction solution was stirred overnight at room temperature. After the reaction was complete, the reaction solution was evaporated to remove the solvent. The residue was dissolved in small amount of dichloromethane, and added with n-hexane (100 mL×3) to precipitate. The precipitate was dried, resulting in 5.78 g of compound of formula E-10, with a yield of 100%. $^1$H-NMR (400 MHz, DMSO-d$_6$) δ 10.91 (s, 1H), 8.99 (s, 1H), 8.15-8.00 (m, 4H), 7.87 (t, J=11.9 Hz, 3H), 7.72 (t, J=7.2 Hz, 3H), 7.55 (dt, J=8.4, 7.8 Hz, 1H), 7.42 (d, J=7.1 Hz, 2H), 7.33 (t, J=7.4 Hz, 2H), 5.93-5.80 (m, 1H), 4.27 (dd, J=6.9, 2.8 Hz, 4H), 3.99 (d, J=5.2 Hz, 3H), 3.75 (dd, J=16.8, 5.9 Hz, 2H), 3.61 (s, 4H), 3.19 (d, J=21.3 Hz, 4H), 3.02 (td, J=6.6, 3.9 Hz, 1H), 2.44 (s, 3H), 2.34 (s, 3H), 2.25 (d, J=7.6 Hz, 3H), 1.93 (s, 2H), 1.83 (dd, J=15.5, 8.3 Hz, 4H), 1.61 (dd, J=12.7, 6.4 Hz, 3H), 1.50 (d, J=6.9 Hz, 2H), 0.86 (dd, J=16.3, 6.5 Hz, 6H); MALDI-TOF MS: [M−H]1024.35

Step S6, Treating the Compound of Formula F-10

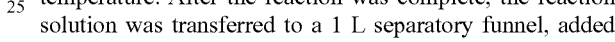

(F-10)

Boc-NH-GLG-OBn (3 g, 6.6149 mmol, Nanjing PharmaBlock) was added to a hydrogenation reaction tank, and 10% Pd/C (0.0500 g) and DMF (30 mL) were added. Hydrogen gas was introduced with 14 psi of hydrogen pressure, and the reaction solution was stirred overnight at room temperature. After the reaction was complete, the reaction solution was suction filtered, and the filter cake was washed with DMF (20 mL×3) for 3 times, and the filtrate was held into a 250 mL round bottom flask to afford F-10.

Step S7, Preparing the Compound of Formula G-10

(G-10)

SB-743921 (2.8503 g, 5.5124 mmol, briefly referred to as "SB7", Nanjing PharmaBlock), HBTU (2.7223 g, 8.2686 mmol) and HOBT (1.1172 g, 8.2686 mmol) were added to a 250 mL flask held with a DMF solution containing F-10 (2.2834 g, 6.6149 mmol). The solution was stirred at −5° C. for about 20 min, and then DIEA (4.0999 mL, 24.8058 mmol) was slowly added dropwise. After the addition of DIEA was complete, the reaction continued at −5° C. for 1 hour, and then continued under stirring overnight at room temperature. After the reaction was complete, the reaction solution was transferred to a 1 L separatory funnel, added with saturated sodium bicarbonate solution (200 mL) and ethyl acetate (300 mL) for extraction. The organic phase was isolated, and the aqueous phase was washed with ethyl acetate (200 mL×3). The organic phases were combined, washed with saturated saline (100 mL×3), dried over anhydrous sodium sulfate, and filtered, resulting in filtrate. The filtrate was concentrated by evaporation to remove the solvent. The residue was mixed with silica gel powder, loaded on a chromatographic column, and eluted with eluent of 1% aqueous ammonia:3.5% methanol:95.5% dichloromethane. Eluate was collected, concentrated by evaporation to remove the solvent, to afford the compound of formula G-10 3.6983 g, with a yield of 79.45%. $^1$H-NMR (400 MHz, DMSO-d$_6$) δ 8.09 (dd, J=9.3, 5.2 Hz, 3H), 7.89 (d, J=7.5 Hz, 1H), 7.65-7.42 (m, 2H), 7.42-7.06 (m, 8H), 6.98 (s, 1H), 5.75 (d, J=6.8 Hz, 1H), 4.39-4.11 (m, 2H), 3.90 (d, J=14.5 Hz, 1H), 3.58 (dd, J=25.3, 6.0 Hz, 4H), 3.15 (dd, J=11.9, 7.5 Hz, 1H), 2.89 (s, 1H), 2.64 (s, 2H), 2.33 (s, 3H), 1.57 (d, J=6.6 Hz, 1H), 1.47 (d, J=7.0 Hz, 2H), 1.36 (s, 9H), 1.23 (dd, J=21.9, 9.2 Hz, 5H), 0.96 (d, J=6.3 Hz, 3H), 0.84 (dd, J=14.8, 6.4 Hz, 6H), 0.53 (d, J=4.8 Hz, 2H); MALDI-TOF MS: [M+H$^+$] 844.25, [M−H$^+$] 842.30, [M+Na$^+$] 866.25

Step S8, Preparing the Compound of Formula H-10

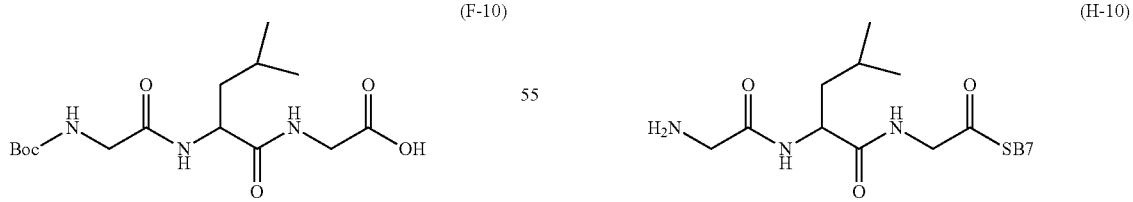

(H-10)

Compound of formula G-10 (3.6483 g, 3.6791 mmol) was added to a 100 mL flask and dissolved in dichloromethane (25 mL), and then TFA (2.1857 mL, 29.4328 mmol) was added. The reaction was stirred overnight at room temperature. After the reaction was complete, the reaction solution was evaporated to remove the solvent. The residue was dissolved in methanol, added with sodium bicarbonate solid powder (20 g) to neutralize the remaining of TFA, and filtered. The filtrate was concentrated by evaporation to remove the solvent. The residue was mixed with silica gel powder, loaded on a chromatographic column, and eluted with eluent of 0.5% aqueous ammonia:5% methanol:94.5% dichloromethane. Eluate was collected and concentrated by evaporation to remove the solvent, to afford 2.4881 g of compound of formula H-10, with a yield of 90.86%. $^1$H-NMR (400 MHz, DMSO-$d_6$) δ 8.17 (dt, J=11.4, 8.0 Hz, 4H), 7.57 (dd, J=8.6, 2.0 Hz, 2H), 7.43-6.96 (m, 9H), 6.24 (s, 2H), 5.76 (s, 1H), 4.34 (d, J=6.7 Hz, 11H), 4.17 (d, J=14.4 Hz, 1H), 3.90 (d, J=14.8 Hz, 1H), 3.53 (d, J=11.5 Hz, 2H), 2.85-2.53 (m, 3H), 2.33 (s, 3H), 1.52 (dd, J=38.0, 6.6 Hz, 3H), 1.32 (s, 1H), 1.15 (dd, J=38.5, 6.6 Hz, 5H), 0.96 (d, J=6.4 Hz, 3H), 0.86 (dd, J=11.2, 6.5 Hz, 6H), 0.53 (d, J=5.2 Hz, 3H); MALDI-TOF MS: [M+H$^+$] 744.25, [M−H$^+$] 742.25, [M+Na$^+$]766.25

Step S9, Preparing the Compound of Formula I-10

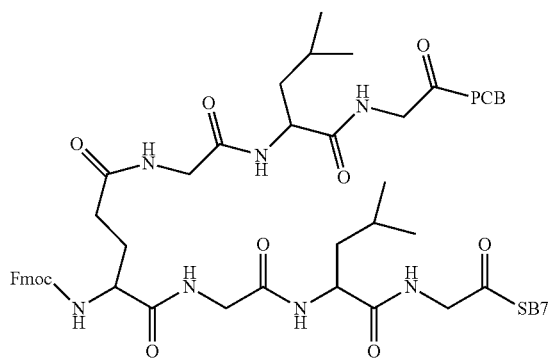

(I-10)

Compound of formula E-10 (2.8900 g, 2.8108 mmol) was added to a 250 mL cylinder reaction bottle and dissolved in DMF (40 mL). The reaction bottle was placed at 0° C. Compound of formula H-10 (2.0921 g, 2.8108 mmol) and PyAOP (1.7585 g, 3.3729 mmol) were added. After about 30 min, 2,4,6-trimethylpyridine (0.3700 ml, 2.8108 mmol) was slowly added dropwise, and the reaction continued under stirring overnight at 0° C. After the reaction was complete, the reaction solution was transferred to a 2 L separatory funnel, and deionized water (300 mL) and ethyl acetate (250 mL) were added for extraction. The organic phase was isolated, and the aqueous phase was washed with EA (150 mL×4). The organic phases were combined, washed with saturated saline (200 m×3), dried over anhydrous sodium sulfate, and suction filtered, resulting in filtrate. The filtrate was concentrated by evaporation to remove the solvent. The residue was mixed with silica gel powder, loaded on a chromatographic column, and eluted with eluent of 7% methanol+93% dichloromethane. Eluate was collected and concentrated to afford 2.8780 g of compound of formula I-10, with a yield of 58.36%. $^1$H-NMR (400 MHz, DMSO-$d_6$) δ 10.16 (s, 1H), 8.96 (s, 1H), 8.24 (d, J=5.7 Hz, 1H), 8.17-7.98 (m, 7H), 7.89 (d, J=9.5 Hz, 4H), 7.79-7.64 (m, 3H), 7.61-7.10 (m, 16H), 5.94-5.68 (m, 2H), 4.46-4.12 (m, 6H), 3.98 (dd, J=12.4, 7.2 Hz, 3H), 3.77-3.56 (m, 9H), 3.24-3.13 (m, 4H), 3.01 (td, J=6.6, 3.9 Hz, 7H), 2.42 (s, 3H), 2.36-2.21 (m, 10H), 1.90 (d, J=11.0 Hz, 3H), 1.83-1.72 (m, 7H), 1.67-1.43 (m, 8H), 1.19 (dd, J=18.9, 11.8 Hz, 1H), 0.88 (ddt, J=13.5, 9.7, 7.8 Hz, 13H), 0.52 (s, 2H); MALDI-TOF MS: [M+H$^+$] 1751.90, [M+] 1750.75

Step S11, Preparing the Compound of Formula J-10

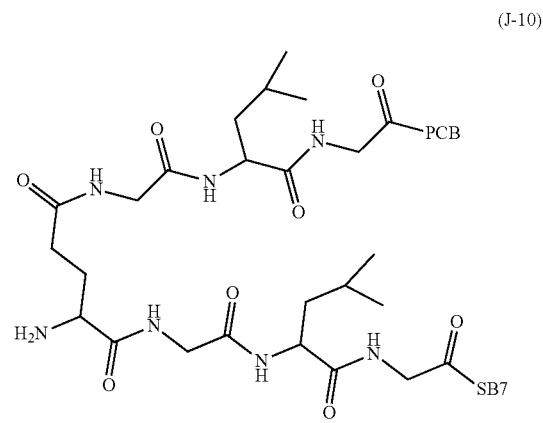

(J-10)

Compound of formula I-10 (2.8725 g, 1.6373 mmol) was added to a 250 mL flask and dissolved in DMF (20 mL), and morpholine (4.2792 mL, 49.1190 mmol) was added. The reaction solution was stirred at room temperature. After about 1 hour, the reaction was complete, and ethyl ether (150 mL) was added under stirring for precipitation. After about 30 min, the supernatant was poured, and the solid in the lower layer was precipitated with n-hexane (150 mL×3) to afford a solid. The solid was dried, mixed with silica gel powder, loaded on a chromatographic column, and eluted with eluent of 1% aqueous ammonia:6% methanol+93% dichloromethane. Eluate was collected and concentrated by evaporation to remove the solvent, to afford 1.5427 g of compound of formula J-10, with a yield of 61.49%. $^1$H-NMR (400 MHz, DMSO-$d_6$) δ 10.16 (s, 1H), 8.96 (s, 1H), 8.36-8.02 (m, 10H), 7.89 (d, J=9.0 Hz, 1H), 7.53 (ddd, J=12.1, 8.8, 2.4 Hz, 3H), 7.20 (dd, J=28.1, 13.3 Hz, 10H), 5.82 (dt, J=24.3, 12.1 Hz, 2H), 4.48-4.22 (m, 2H), 4.13 (dd, =22.6, 10.2 Hz, 1H), 4.08-3.89 (m, 3H), 3.81-3.50 (m, 11H), 3.23-3.09 (m, 6H), 2.81-2.67 (m, 3H), 2.42 (s, 3H), 2.39-2.18 (m, 10H), 1.91-1.75 (m, 5H), 1.67-1.43 (m, 10H), 1.19 (dd, J=18.9, 11.8 Hz, 1H), 0.88 (ddd, J=19.8, 16.3, 4.3 Hz, 16H), 0.52 (s, 2H); MALDI-TOF MS: [M+] 1528.85

Step S12, Preparing the Compound of Formula K-10

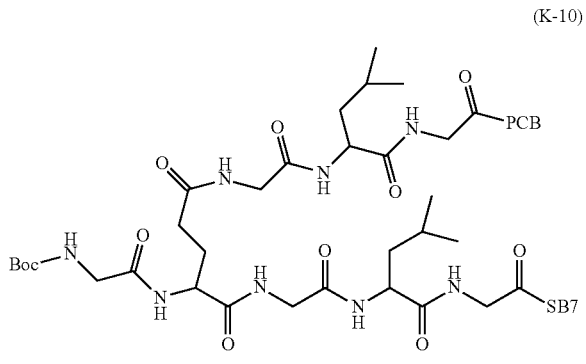

(K-10)

Compound of formula J-10 (1.5427 g, 1.0068 mmol), Boc-Gly-OH (0.2117 g, 1.2082 mmol), HBTU (0.5727 g, 5102 mmol) and HOBT (0.2041 g, 1.5102 mmol) were added to a 250 mL flask and dissolved in DMF (25 mL). The reaction solution was stirred at −5° C. for about 30 min, and then DIEA (0.7488 mL, 4.5306 mmol) was slowly added dropwise. After the addition of DIEA was complete, the reaction continued at −5° C. for 1 hour, and then continued under stirring overnight at room temperature. After the reaction was complete, the reaction solution was transferred to a 1 L separatory funnel, added with saturated sodium bicarbonate solution (250 mL) and ethyl acetate (200 mL) for extraction. The organic phase was isolated, and the aqueous phase was washed by ethyl acetate (150 mL×3). The organic phases were combined, washed by saturated saline (150 mL×3), dried over anhydrous sodium sulfate, and suction filtered, resulting in filtrate. The filtrate was concentrated by evaporation to remove the solvent. The residue was mixed with silica gel powder, loaded on a chromatographic column, and eluted with eluent of 1% aqueous ammonia+6% methanol+95.5% dichloromethane. Eluate was collected, and concentrated by evaporation to remove the solvent, to afford 1.4322 g of compound of formula K-10, with a yield of 84.20%. $^1$H-NMR (400 MHz, DMSO-$d_6$) δ 10.16 (s, 1H), 8.96 (s, 1H), 8.27 (s, 1H), 8.15-7.86 (m, 10H), 7.53 (ddd, J=12.0, 8.9, 2.4 Hz, 3H), 7.36-7.09 (m, 9H), 6.92 (t, J=5.7 Hz, 1H), 5.90-5.74 (m, 2H), 4.46-4.16 (m, 4H), 3.96 (dd, J=23.4, 9.8 Hz, 3H), 3.81-3.50 (m, 12H), 3.24-3.06 (m, 6H), 2.86-2.61 (m, 3H), 2.42 (s, 3H), 2.35-2.15 (m, 10H), 1.83 (d, J=44.8 Hz, 5H), 1.69-1.40 (m, 10H), 1.36 (s, 9H), 1.18 (d, J=18.9 Hz, 1H), 1.01-0.79 (m, 16H), 0.52 (d, J=4.8 Hz, 2H); MALDI-TOF MS: [M+H] 1686.95, [M$^+$] 1685.95, [M+Na$^+$] 1708.95 perature. After the reaction was complete, the reaction solution was evaporated by evaporation to remove the solvent. The residue was dissolved in ethyl acetate, transferred to a 1 L separatory funnel, and extracted with saturated sodium bicarbonate solution (250 mL) and ethyl acetate (200 mL). The organic phase was isolated, and the aqueous phase was washed by ethyl acetate (150 mL×4). The organic phases were combined, dried over anhydrous sodium sulfate, and suction filtered. The filtrate was concentrated by evaporation to remove the solvent. The residue was mixed with silica gel powder, loaded on a chromatographic column, and eluted with eluent of 1% aqueous ammonia+6% methanol+93% dichloromethane and eluent of 1% aqueous ammonia+7% methanol+93% dichloromethane. Eluate was collected and concentrated by evaporation to remove the solvent, to afford 1.2235 g of compound of formula L, with a yield of 92.33%. $^1$H-NMR (400 MHz, DMSO-$d_6$) δ 10.16 (s, 1H), 8.96 (s, 1H), 8.33 (t, J=5.5 Hz, 1H), 8.21-7.78 (m, I0H), 7.65-7.41 (m, 3H), 7.41-7.06 (m, 9H), 5.92-5.71 (m, 2H), 4.48-4.12 (m, 4H), 4.01-3.83 (m, 3H), 3.80-3.56 (m, 11H), 3.15 (dd, J=18.0, 5.7 Hz, 7H), 2.81-2.60 (m, 3H), 2.42 (s, 3H), 2.37-2.16 (m, 10H), 1.95-1.45 (m, 15H), 1.36-1.09 (m, 3H), 0.87 (ddd, J=21.2, 16.1, 6.4 Hz, 16H), 0.53 (d, J=5.1 Hz, 2H); MALDI-TOF MS: [M+] 1585.70, [M+Na$^+$] 1608.70

Step S14, Preparing the Compound of Formula M-10

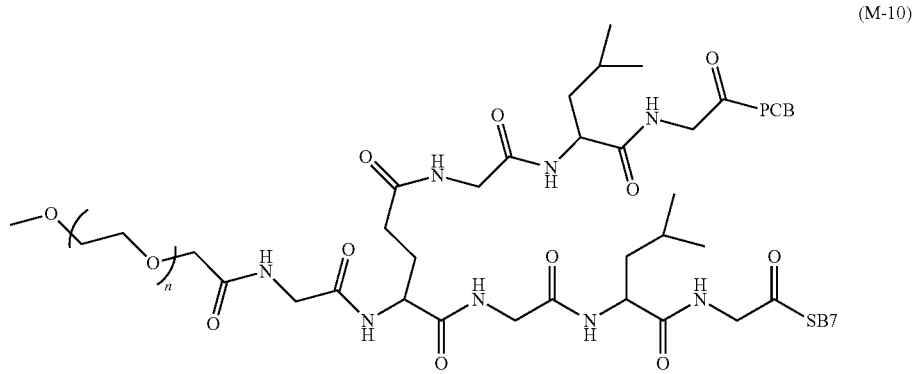

(M-10)

Step S13, Preparing the Compound of Formula L-10

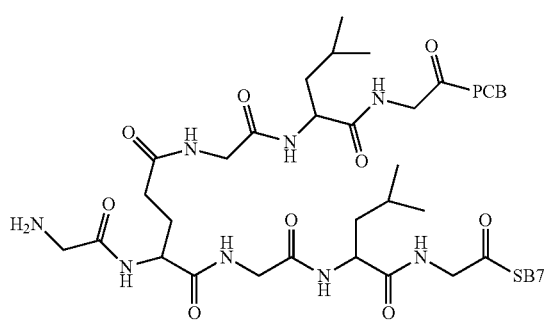

(L-10)

Compound of formula K-10 (1.4108 g, 0.8351 mmol) was added to a 250 mL flask and dissolved in dichloromethane (10 mL), and TFA (0.6175 mL, 8.3510 mmol) was added. The reaction solution was stirred overnight at room tem- Compound of formula L-10 (0.8398 g, 0.5293 mmol) was added to a 250 mL flask, and dissolved in dichloromethane (25 mL) and DMF (4 mL), and then M-SCM-10K (4.6715 g, 0.4410 mmol, Beijing Jiankai) was added. The reaction solution was stirred at room temperature in dark. After the reaction was complete, the reaction solution was concentrated to about 20 mL, and added with dichloromethane (10 mL) to dissolve. Ethyl ether (150 mL) was added for precipitation, followed by filtration. Filter cake was washed with ethyl ether (150 mL×4), resulting in crude product. The solid product was dissolved in dichloromethane, and the solution was concentrated. The residue was mixed with silica gel powder, loaded on a chromatographic column, and eluted with eluent of 1% aqueous ammonia+6% methanol+93% dichloromethane. Eluate was collected, and concentrated by evaporation to remove the solvent, to afford a solid. The solid was dissolved in small amount of anhydrous ethanol, precipitated with ethyl ether (150 mL×2), and suction filtered. Filter cake was washed with ethyl ether (150 mL×4). The obtained solid was dried by evaporation to afford 4.9270 g of compound of formula M-10, with a yield of 92.59%. $^1$H-NMR (400 MHz, DMSO-$d_6$) δ 10.15 (d, J=6.3 Hz, 1H), 8.96 (s, 1H), 8.24 (d, J=24.7 Hz, 2H), 8.17-7.81 (m, 10H), 7.53 (ddd, J=12.0, 8.8, 2.3 Hz, 3H), 7.20 (d, J=41.3 Hz, 9H), 5.90-5.70 (m, 2H), 4.47-4.16 (m, 7H), 4.08-3.44 (m, 920H), 3.14 (dd, J=22.7, 9.9 Hz, 7H), 2.66 (d, J=7.7 Hz, 3H), 2.42 (s, 3H), 2.35-2.15 (m, 10H), 1.80 (dd, J=47.2, 23.2 Hz, 5H), 1.52 (d, J=50.5 Hz, 10H), 1.22 (d, J=13.7 Hz, 1H), 0.98-0.74 (m, 16H), 0.51 (s, 2H)

Experimental Example

I. Experimental Scheme

1. Experimental Subject and Material

Experimental animals: Balb/c nude mice, SPF grade; Shanghai Lingchang Biotechnology Co., Ltd.; license number: SCXK (Shanghai) 2013-0018, certificate number: 2013001828988; 16-18 weeks old, female Test drug for experimental group: compound of formula M-10, prepared in Example 11, molecular weight: 12066, yellow powder, storage condition: 4° C.; compound of formula M-10 was weighed, dissolved with physiological saline under the condition of ultrasound, and then administered; two doses of drug was prepared each time, and the remaining drug was stored at 4° C.

Agent for blank control group: normal saline, purchased from Shandong Kangning Pharmaceutical, batch No.: A16071105

1460 Culture medium: Shanghai Yuanpei Biological, item number: L210KJ

FCS: Sciencell, item number: 0500

100*Penicillin Streptomycin Double Antibody: Gibco, item number: 10378-016

2. Experimental Protocol 2.1 Model Establishment a) resuscitation and expansion of Colo-205 cells;

b) cells were expanded and collected, and a cell suspension having a concentration of $2 \times 10^7$ cell/ml was prepared with serum-free 1640 medium;

c) the nude mice were inoculated subcutaneously on the right side, 0.1 ml/each, that is, the number of cells per nude mouse was $2 \times 10^6$; and 20 mice were inoculated.

2.2 Grouping and Administration

The size of Colo-205 subcutaneous tumor was measured, and 16 tumor-bearing mice were chosen, and randomly divided into 2 groups according to the tumor volume, 8 in each group. The day of grouping was recorded as Day 1, and the administration started on the same day. The grouping and administration protocol are shown in Table 1:

2.3 Observation and Monitoring

Tumor size and body weight were measured every three days, and animal status was observed and recorded.

2.4 Experimental End Point

On the next day after the last measurement, the animals were euthanized with carbon dioxide. The tumor-bearing mice were photographed, and the tumor was stripped, photographed and weighed, and then the experiment was terminated.

3. Detection Index and Method of Calculation and Statistical Analysis 3.1 Tumor Volume (TV)

TV=½×a×b², wherein $a$ and $b$ represent length and width, respectively.

3.2 Relative Tumor Volume (RTV)

RTV=$TV_1/TV_t \times 100$, wherein $TV_1$ is the tumor volume on the day of administration (i.e. Day 1) and $TV_t$ is the tumor volume at each measurement.

3.3 Relative Tumor Proliferation Rate T/C (%)

T/C (%)=$(T_{RTC}/C_{RTV}) \times 100$ $T_{RTC}$: treatment group RTC; $C_{RTV}$: blank control group RTV 3.4 Tumor Weight Inhibition Rate IR (%)

IR (%)=$(C_{TW}-T_{TW})/C_{TW} \times 100$ $T_{TW}$: tumor weight of the treatment group; $C_{TW}$: tumor weight of the blank control group; TW: tumor weight.

3.5 Statistical Analysis

Test data were expressed as mean f standard deviation (mean±SD), and body weight and tumor volume were examined using Student's t-test. P<0.05 indicates a significant difference, and P<0.01 indicates a very significant difference.

II. Experimental Results

1. Body Weight

The day of grouping of mice was recorded as Day 1, and the body weight of animals of each group when grouping was about 20 g, and the body weight of the animals were measured every three days from the day of grouping (Day 1) to the end point of the experiment (Day 11). The results are shown in Table 2. The body weight of the control group after the grouping grew normally, and the body weight of the M-10 group showed a gradual decline. At the end of the experiment, there was a significant difference between the weight of the drug-administered group and the control group. On Day 10, it was found that the weight of the 4# animal in the drug-administered group was severely decreased, only 12.45 g, and on Day 11, the animal died.

TABLE 1

| | | | | | | |
|---|---|---|---|---|---|---|
| Animal grouping and administration |||||||
| Group | N | Name | Administration doses | Administration volume | Administration routine | Administration frequency/period |
| 1 | 8 | Control | 0 | 0.1 ml/10 g | i.p. | Once every three days (q3d), 4 times in total |
| 2 | 8 | M-10 | 10 mg/kg | 0.1 ml/10 g | i.p. | Once every three days (q3d), 4 times in total |

TABLE 2

Effect of test compound on the body weight of Colo-205 tumor-bearing mice (data expressed as mean ± SD)

| Group | Dose (mg/kg) | Number of Animals | | Body weight (g) | |
|---|---|---|---|---|---|
| | | Day 1 | Day 10 | Day 1 | Day 10 |
| Control | 0 | 8 | 8 | 20.07 ± 1.41 | 20.32 ± 1.54 |
| M-10 (ip) | 10 | 8 | 7 | 19.96 ± 1.1 | 17.07 ± 2.5** | vs Control, **p < 0.01

2. Tumor Volume

After inoculation, the mice were randomly grouped according to tumor volume when subcutaneous tumor volume increased to 100-200 mm$^3$. The tumor volume of each group when grouping was about 210 mm$^3$, and the tumor volume was measured every three days from the day of grouping (Day 1) to the end of the experiment (Day 11). The results (Table 3) showed that at the end of the experiment, the tumor volume of the control group was 1411.47 mm 3 and RTV was 680.32%. The tumor model worked normally.

It can be seen from the tumor growth curve that the tumor volume of the control group was 1411.47 mm$^3$ at the end of the experiment. As for M-10 administration group, the tumor volume grew slowly after the first administration, and then gradually decreased; and at the end of the experiment, the tumor volume was 41.95 mm$^3$, and tumor volume (TV) and relative tumor volume (RTV) have significant differences compared with the control group.

4. Result Analysis

1) In this experiment, in order to examine the efficacy of the compound, Colo205 tumor-bearing mice were administered. When the volume of subcutaneous tumors grew to 200 mm$^3$, the mice were randomly grouped according to the tumor volume, and administration was started on the same day. The tumor volume of each group when grouping was about 210 mm$^3$. At the end of the experiment, the tumor volume of the control group was 1411.47 mm$^3$ and RTV was 680.32%. The tumor model worked normally.

2) It can be seen from the tumor growth curve that the tumor volume of the control group was 1411.47 mm$^3$ at the end of the experiment. As for the M-10 administration group, the tumor volume of increased first and then decreased, the tumor volume at the end of the experiment was 41.95 mm$^3$, and the tumor volume (TV) and relative tumor volume (RTV) were significantly different from those of the control group.

TABLE 3

Inhibition effect of test compound on Colo205 subcutaneous xenografts in nude mice (data expressed as Mean ± SD)

| Group | Dose (mg/kg) | TV (mm$^3$) | | RTV (%) | T/C (%) |
|---|---|---|---|---|---|
| | | Day 1 | Day 10 | Day 10 | Day 10 |
| Control | 0 | 213.64 ± 45.31 | 1411.47 ± 226.77 | 680.32 ± 155.37 | — |
| M-10 | 10 | 210.39 ± 44.1 | 41.95 ± 10.72 | 20.04 ± 4.52 | 97.1 | vs Control, **p < 0.01

3. Tumor Weight at Experimental End Point

After the drug efficacy experiment was completed, the tumor-bearing mice were euthanized with carbon dioxide, and the tumor was stripped, photographed and weighed. The results (Table 4) showed that the tumor weight of the control group was 0.90 g, and the tumor weight of the M-10 administration group was 0.013 g; the tumor inhibition rate was 98.5%. The tumor weight and tumor inhibition rate of the administration group were significantly different from those of the control group. The effect of the compound on tumor in Colo205 tumor-bearing mice was visually observed from FIG. 4.

TABLE 4

Tumor weight of each group at the end of the experiment (data expressed as Mean ± SD, n = 8)

| Group | Tumor weight TW (g) | Inhibition rate IR (%) |
|---|---|---|
| Control | 0.90 ± 0.31 | — |
| M-10 | 0.013 ± 0.004** | 98.5 | vs Control, **p < 0.01

3) At the end of the experiment, the tumor weight of the control group was 0.90 g; and as for the M-10 administration group, the tumor weight was 0.013 g, and the tumor inhibition rate was 98.5%. The tumor weight and tumor inhibition rate of the administration group were significantly different from those of the control group.

4) It can be seen from the weight curve that, the body weight of the control group decreased first and then increased after the grouping, and the body weight of the M-10 group gradually decreased. At the end of the experiment, there was a significant difference between the weight of the administration group and the control group. On Day 10, it was found that the weight loss of the 4# animal in the administration group was severe, only 12.45 g, and on Day 11, the animal died.

5) During the experiment, it was found that after administration of the M-10, the mice showed weight loss, dry and chapped skin, low body surface temperature and slight loose feces, etc. In this experiment, a nude mouse Colo205 subcutaneous xenografts model was successfully established, and the effect of the test compound on the growth of the tumor was examined. In the experimental system and with the dose set, compound M-10 has a strong inhibitory effect on tumor growth of the animal model.

While the invention has been illustrated and described with reference to the particular examples, it will be understood that many changes and modifications can be made without departing from the spirit and scope of the invention. Accordingly, this means that all of these changes and modifications within the scope of the invention are included in the attached claims.

INDUSTRIAL APPLICABILITY

The intermediate drug, or derivative or pharmaceutically acceptable salt thereof provided by the present invention can be used for preparing an anticancer medicament, for example, for achieving multi-target payload in a single nano-drug, and can be used for treating cancer. By the method of preparation provided by the invention, a polyethylene glycol-coupled anticancer dual-drug or even a polyethylene glycol-coupled anticancer multi-drug can be easily synthesized, thereby realizing multi-target and multi-therapy simultaneous administration and greatly reducing toxicity. The invention is advantages to overcome the multi-drug resistance of cancer, has a synergistic effect, and can be used for preparing anticancer medicaments and treating cancer, and has great clinical value and broad market prospect.

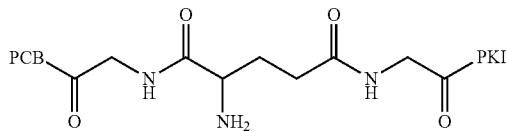

wherein, PCB is palbociclib, PKI is allosteric PKI-587;

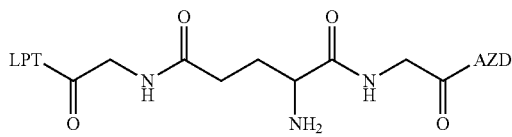

wherein, LPT is lapatinib, AZD is AZD5363;

The invention claimed is:
1. A compound or pharmaceutical acceptable salt thereof as shown by formula I;

wherein, i=2; Z is selected from any one of glutamic acid, aspartic acid, and glutaric acid having amino group; N is selected from glycine, glycine-glycine GG, glycine-leucine-glycine GLG, glycine-phenylalanine-alanine GFA, glycine-leucine-alanine GLA or glycine-phenylalanine-leucine-glycine GFLG (SEQ ID NO: 1);
AC is a combination of at least two anticancer drugs selected from: palbociclib, Veliparib, de-terminal-dimethyl PKI-587, allosteric PKI-587, AZD-5363, lapatinib,
wherein the compound is selected from;

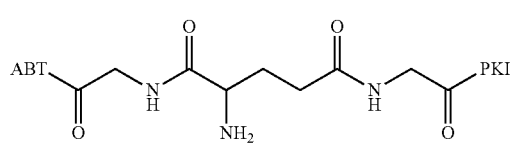

wherein, ABT is Veliparib, PKI is allosteric PKI-587;

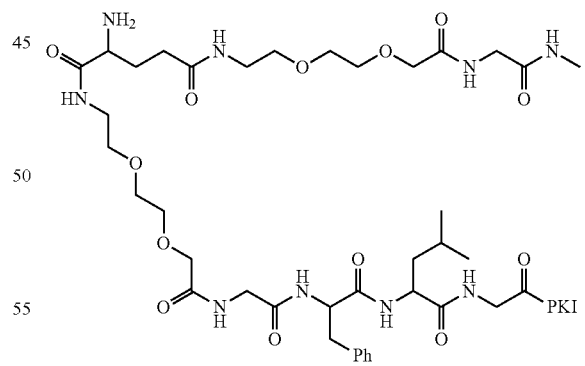

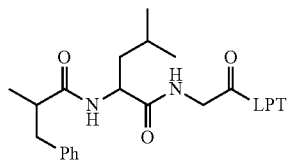

wherein LPT is lapatinib, PKI is allosteric PKI-587; and

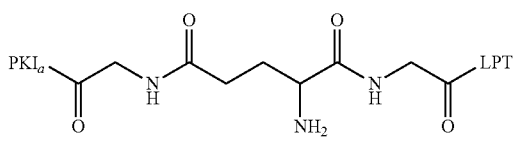

wherein, LPT is lapatinib, $PKI_a$ is de-terminal-dimethyl PKI-587.

2. A polyethylene glycol-coupled anticancer drug, or a pharmaceutical acceptable salt thereof as shown by formula II;

$$PEG + X-(Y)_m-Z + N-AC]_i\}_j \quad (II)$$

wherein, PEG is selected from single-arm or multi-arm polyethylene glycol; X is selected from

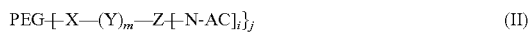

Y is selected from carboxylic acid having amino group or corresponding acyl substituent thereof, $Z+N-AC]_i$ is the compound or pharmaceutical acceptable salt thereof as shown by formula I of claim 1;

m=0, 1 or 2; n=1-5; j=arm number of PEG.

3. The polyethylene glycol-coupled anticancer drug, or a pharmaceutical acceptable salt thereof according to claim 2, wherein PEG is single-arm, two-arm, four-arm or eight-arm polyethylene glycol.

4. The polyethylene glycol-coupled anticancer drug or a pharmaceutical acceptable salt thereof according to claim 2, wherein
Y is selected from

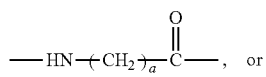

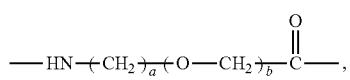

wherein, a=0~8; b=0~8; a and b are not 0 simultaneously.

5. The polyethylene glycol-coupled anticancer drug or a pharmaceutical acceptable salt thereof according to claim 2, wherein Y is selected from

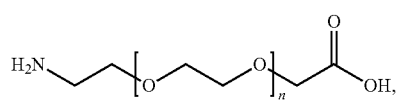

wherein n = 1~1000

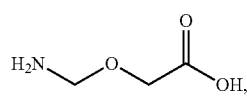

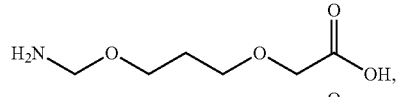

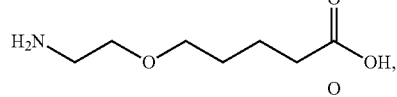

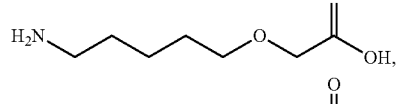

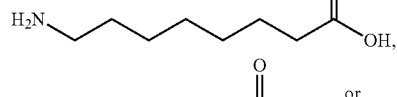

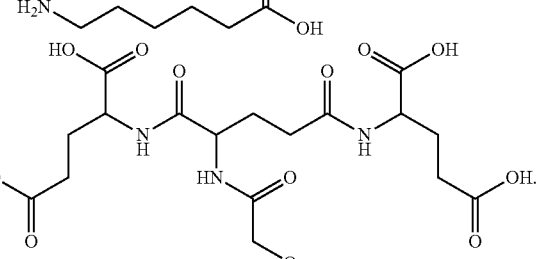

6. The polyethylene glycol-coupled anticancer drug, or a pharmaceutical acceptable salt thereof according to claim 2, which is selected from the following compounds:

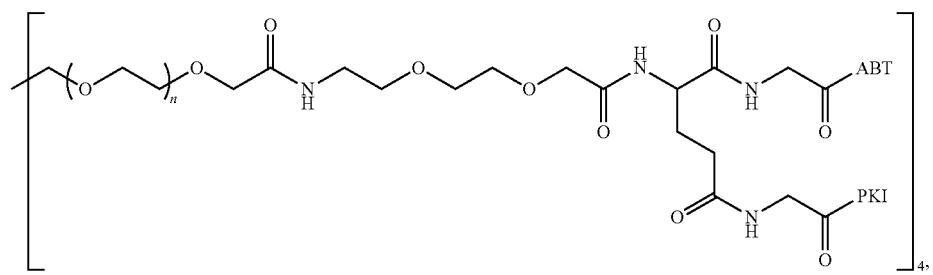

wherein, ABT is Veliparib, PKI is allosteric PKI-587;

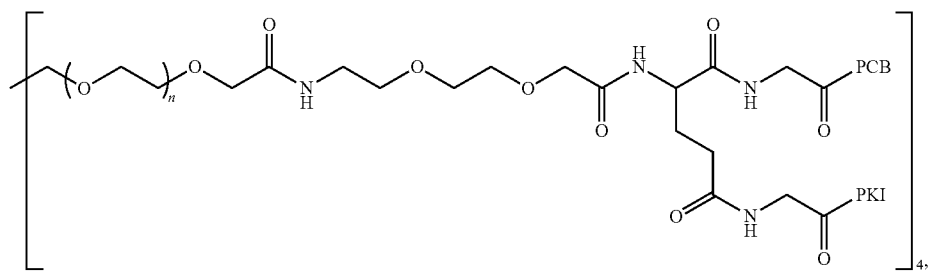
wherein, PCB is palbociclib, PKI is allosteric PKI-587;
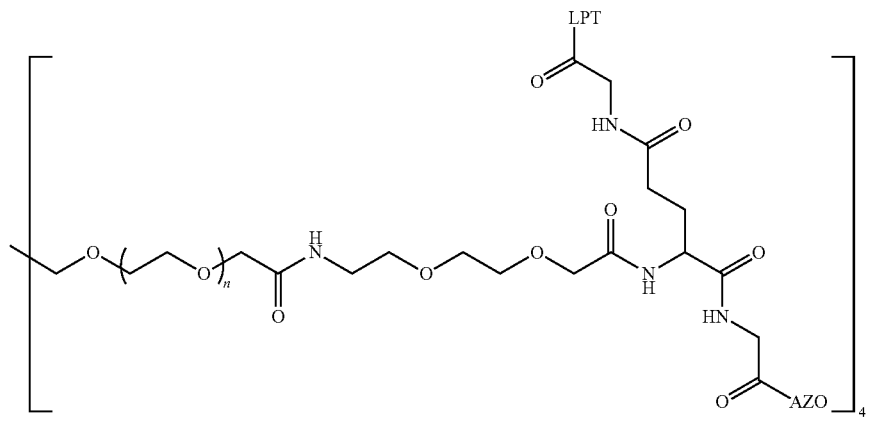
wherein, LPT is lapatinib, AZD is AZD5363;
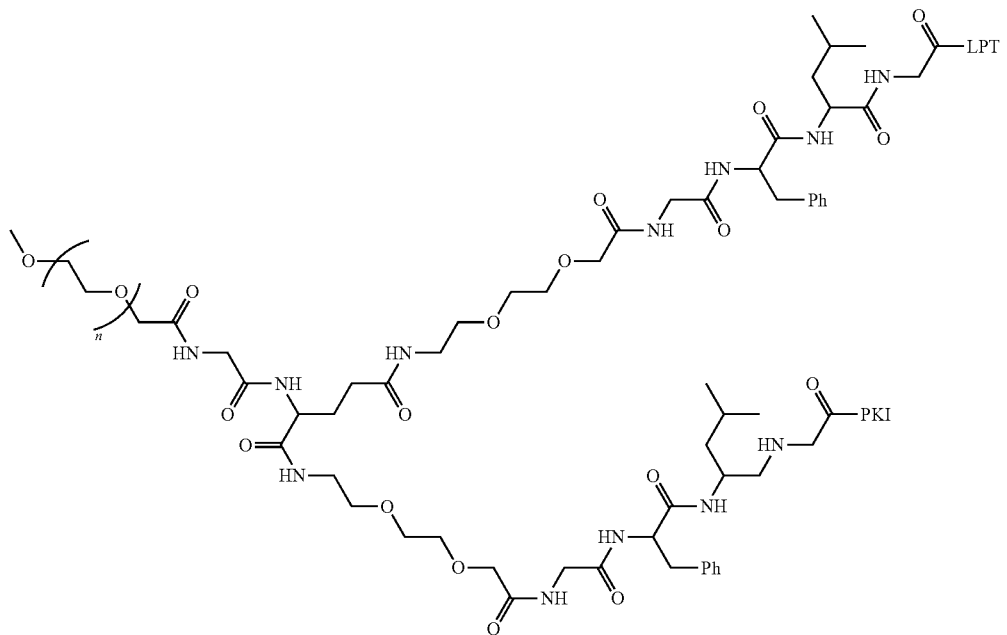
wherein, LPT is lapatinib, PKI is allosteric PKI-587; and

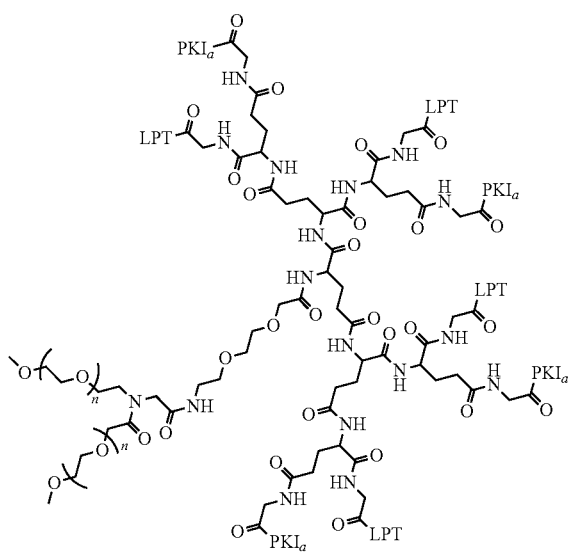

wherein, LPT is lapatinib, PKI$_a$ is de-terminal-dimethyl PKI-587.

7. A method for preparing the compound or pharmaceutical acceptable salt thereof as shown by formula I of claim 1, wherein the method includes the following steps:
performing amidation reactions of two anticancer drugs with amino acid or peptide, resulting in the first intermediates having a structure unit of N-AC in the formula I;
performing an amidation reaction of any one of the first intermediates with dicarboxylic acid, polycarboxylic acid having amino group or a corresponding acyl substituent thereof, resulting in the second intermediate having a structure unit of Z—N-AC in the formula I; and
performing an amidation reaction of the second intermediate with the remaining first intermediate, resulting in the intermediate drug Z—[—N-AC]$_i$ as shown by formula I.

8. The method according to claim 7, wherein the first intermediate is prepared by a method including the following steps: connecting an amino acid, or polypeptide having amino protecting group with an anticancer drug by amidation reaction in the presence of a polypeptide condensation agent, and then removing the amino protecting group.

9. The method according to claim 7, wherein the second intermediate is prepared by a method including the following steps: connecting the first intermediate with a dicarboxylic acid, polycarboxylic acid or a corresponding acyl substituent thereof having amino group, amino protecting group and carboxyl protecting group by amidation reaction in the presence of PyAOP, and then removing the carboxyl protecting group.

10. The method according to claim 7, wherein the method for preparing the intermediate drug as shown by formula I also includes the following steps: performing amidation reaction of the second intermediate with at least one of the first intermediates in the presence of PyAOP and 2, 4, 6-trimethylpyridine at −10° C.~10° C., and then removing the amino protecting group.

11. The method according to claim 7, including the following steps: at first connecting at least two anticancer drugs together to produce an organics, and then performing amidation reaction of the organics combined with two anticancer drugs with an amino acid or peptide, wherein the drug intermediate as shown by formula I has at least one binding site linked with the two anticancer drugs.

12. A method for preparing the polyethylene glycol-coupled anticancer drug, or a pharmaceutical acceptable salt thereof as shown by formula II of claim 2, wherein, the method includes the following steps:
performing amidation reaction of the intermediate drug as shown by formula I with carboxylic acid having amino group or a corresponding acyl substituent thereof, resulting in the fourth intermediate having structure unit (Y)$_m$—Z—[—N-AC]$_i$ in formula II; and
coupling the fourth intermediate with polyethylene glycol by amide bond, resulting in a product having a structure as shown by formula II.

13. The method according to claim 12, wherein the fourth intermediate is prepared by a method including the following steps: connecting a carboxylic acid having amino group and amino protecting group or a corresponding acyl substituent thereof with the third intermediate by amidation in the presence of a polypeptide condensation agent, and then removing the amino protecting group.

14. An anticancer medicament, including the compound or pharmaceutical acceptable salt thereof as shown by formula I of claim 1.

15. An anticancer medicament, including the polyethylene glycol-coupled anticancer drug, or a pharmaceutical acceptable salt thereof as shown by formula II of claim 2.

16. A method for treating cancer, including administrating an anticancer medicament according to claim 14.

17. A method for treating cancer, including administrating an anticancer medicament according to claim 15.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: synthetic

<400> SEQUENCE: 1

Gly Phe Leu Gly
1